(12) United States Patent
Lim et al.

(10) Patent No.: US 11,696,863 B2
(45) Date of Patent: *Jul. 11, 2023

(54) SURGICAL FRAME HAVING TRANSLATING LOWER BEAM AND MOVEABLE LINKAGE OR SURGICAL EQUIPMENT ATTACHED THERETO AND METHOD FOR USE THEREOF

(71) Applicant: Warsaw Orthopedic, Inc., Warsaw, IN (US)

(72) Inventors: Roy K. Lim, Germantown, TN (US); Richard A. Hynes, Melbourne Beach, FL (US); Lindsey G. Waugh, Memphis, TN (US); Matthew M. Morrison, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 468 days.

This patent is subject to a terminal disclaimer.

(21) Appl. No.: 16/880,374

(22) Filed: May 21, 2020

(65) Prior Publication Data
US 2020/0281788 A1    Sep. 10, 2020

Related U.S. Application Data

(63) Continuation of application No. 16/107,788, filed on Aug. 21, 2018, now Pat. No. 10,835,439.

(51) Int. Cl.
*A61G 13/08* (2006.01)
*A61G 13/04* (2006.01)
(Continued)

(52) U.S. Cl.
CPC .............. *A61G 13/08* (2013.01); *A61B 34/30* (2016.02); *A61G 13/04* (2013.01);
(Continued)

(58) Field of Classification Search
CPC .... A61G 13/08; A61G 13/04; A61G 13/0054; A61G 13/104; A61G 13/121;
(Continued)

(56) References Cited

U.S. PATENT DOCUMENTS 2,691,979 A    10/1954 Watson
3,060,925 A    10/1962 Honsaker
(Continued)

FOREIGN PATENT DOCUMENTS

JP    2018069048    5/2018
WO    WO0062731    10/2000
(Continued)

*Primary Examiner* — Myles A Throop

(57) ABSTRACT

A surgical frame and method for use thereof is provided. The surgical frame is capable of reconfiguration before, during, or after surgery using a moveable main beam supporting a patient thereon. The surgical frame includes a translating lower beam that is moveable between at least a first lateral position and a second lateral position, and a linkage and/or surgical equipment supportively and moveably attached to the translating lower beam or interconnected with the translating lower beam via the linkage. The linkage and/or the surgical equipment are moveable between a first position at or adjacent a first end of the translating lower beam and a second position at or adjacent a second end of the translating lower beam. The translating lower beam is used to join a first support portion and a second support portion of the surgical frame to one another, and movement of the translating lower beam affords access to a patient receiving area. A linear movement mechanism can be used to facilitate movement of the linkage and/or the surgical equipment along the translating lower beam to avoid interference with the main beam or the translating lower beam.

20 Claims, 43 Drawing Sheets

(51) Int. Cl.
*A61B 34/30* (2016.01)
*A61G 13/00* (2006.01)
*A61G 13/12* (2006.01)
*A61G 13/10* (2006.01)

(52) U.S. Cl.
CPC .... *A61B 2034/304* (2016.02); *A61G 13/0054* (2016.11); *A61G 13/104* (2013.01); *A61G 13/121* (2013.01); *A61G 13/122* (2013.01); *A61G 13/123* (2013.01)

(58) Field of Classification Search
CPC ............... A61G 13/122; A61G 13/123; A61G 13/1245; A61B 34/30; A61B 2034/304
See application file for complete search history.

(56) References Cited

U.S. PATENT DOCUMENTS

| | | |
|---|---|---|
| 3,227,440 A | 1/1966 | Scott |
| 3,293,667 A | 12/1966 | Ohrberg |
| 3,306,287 A | 2/1967 | Arp |
| 3,745,996 A | 7/1973 | Rush |
| 3,828,377 A | 8/1974 | Fary, Sr. |
| 4,029,089 A | 6/1977 | Mulhlland |
| 4,655,200 A | 4/1987 | Knight |
| 4,705,026 A | 11/1987 | Chaussy |
| 4,866,796 A | 9/1989 | Robinson |
| 4,872,656 A | 10/1989 | Brendgord |
| 4,901,384 A | 2/1990 | Eary |
| 4,915,101 A | 4/1990 | Cuccia |
| 5,009,407 A | 4/1991 | Watanabe |
| 5,088,706 A | 2/1992 | Jackson |
| 5,103,511 A | 4/1992 | Sequin |
| 5,131,106 A | 7/1992 | Jackson |
| 5,390,383 A | 2/1995 | Carn |
| 5,410,769 A | 5/1995 | Waterman |
| 5,444,882 A | 8/1995 | Andrews |
| 5,613,254 A * | 3/1997 | Clayman ............ A61G 13/0054 5/613 |
| 5,642,302 A | 6/1997 | Dumont |
| 5,860,899 A | 1/1999 | Rassman |
| 5,991,651 A | 11/1999 | LaBarbera |
| 6,003,176 A | 12/1999 | Wasley |
| 6,076,525 A | 6/2000 | Hoffman |
| 6,112,349 A | 9/2000 | Connolly |
| 6,154,901 A | 12/2000 | Carr |
| 6,260,220 B1 | 7/2001 | Lamb |
| 6,295,671 B1 | 10/2001 | Reesby et al. |
| 6,311,349 B1 | 11/2001 | Kazakia |
| 6,367,104 B1 | 4/2002 | Fallbo, Sr. et al. |
| 6,378,149 B1 | 4/2002 | Sanders et al. |
| 6,516,483 B1 | 2/2003 | VanSteenburg |
| 6,566,833 B2 | 5/2003 | Barlett |
| 6,615,430 B2 | 9/2003 | Heimbrock |
| 6,671,905 B2 | 1/2004 | Bartlett et al. |
| 6,681,423 B2 | 1/2004 | Zachrisson |
| 6,701,553 B1 | 3/2004 | Hand et al. |
| 6,701,554 B2 | 3/2004 | Heimbrock |
| 6,701,558 B2 | 3/2004 | VanSteenburg |
| 6,715,169 B2 | 4/2004 | Niederkrom |
| 6,728,983 B2 | 5/2004 | Bartlett et al. |
| 6,732,390 B2 | 5/2004 | Krywiczanin |
| 6,739,006 B2 | 5/2004 | Borders et al. |
| 6,874,181 B1 | 4/2005 | Connolly et al. |
| 6,934,986 B2 | 8/2005 | Krywiczanin et al. |
| 6,941,951 B2 | 9/2005 | Hubert et al. |
| 6,966,081 B1 | 11/2005 | Sharps |
| 7,100,225 B1 | 9/2006 | Bailey |
| 7,189,214 B1 | 3/2007 | Saunders |
| 7,219,379 B2 | 5/2007 | Krywiczanin et al. |
| 7,234,180 B2 | 6/2007 | Horton et al. |
| 7,290,302 B2 | 11/2007 | Sharps |
| 7,426,930 B1 | 9/2008 | Bailey |
| 7,472,440 B2 | 1/2009 | Bartlett et al. |
| 7,484,253 B1 | 2/2009 | Coppens |
| 7,496,980 B2 | 3/2009 | Sharps |
| 7,600,281 B2 | 10/2009 | Skripps |
| 7,603,790 B2 | 10/2009 | Jordan et al. |
| 7,669,262 B2 | 3/2010 | Skripps |
| 7,739,762 B2 | 6/2010 | Lamb et al. |
| 7,882,583 B2 | 2/2011 | Skripps |
| 8,118,029 B2 | 2/2012 | Gneiting et al. |
| 8,234,730 B2 | 10/2012 | Copeland et al. |
| 8,286,283 B2 | 10/2012 | Copeland et al. |
| 8,286,637 B2 | 10/2012 | Kaska |
| 8,381,331 B2 | 2/2013 | Sharps et al. |
| 8,413,660 B2 | 4/2013 | Weinstein et al. |
| 8,439,948 B1 | 5/2013 | King |
| 8,443,473 B2 | 5/2013 | Maxwell |
| 8,584,281 B2 | 11/2013 | Diel et al. |
| 8,635,725 B2 | 1/2014 | Tannoury et al. |
| 9,072,646 B2 | 7/2015 | Skripps et al. |
| 9,265,680 B2 | 2/2016 | Sharps |
| 9,339,430 B2 | 5/2016 | Jackson et al. |
| 9,358,170 B2 | 6/2016 | Jackson |
| 9,414,982 B2 | 8/2016 | Jackson |
| 9,498,397 B2 | 11/2016 | Hight et al. |
| 9,522,078 B2 | 12/2016 | Pizzini |
| 9,554,959 B2 | 1/2017 | Carn |
| 9,655,793 B2 | 5/2017 | Hertz |
| 9,700,476 B2 | 7/2017 | Hoel et al. |
| 9,713,562 B2 | 7/2017 | Perlman et al. |
| 9,744,089 B2 | 8/2017 | Jackson |
| 9,937,006 B2 | 4/2018 | Skripps et al. |
| 9,993,380 B2 | 6/2018 | Jackson |
| 10,314,758 B2 | 6/2019 | Dolliver et al. |
| 10,342,722 B2 | 7/2019 | Garrido |
| 10,406,054 B1 | 9/2019 | Scholl et al. |
| 10,576,006 B2 * | 3/2020 | Lim ................. A61G 13/1235 |
| 10,835,439 B2 * | 11/2020 | Lim ................. A61G 13/08 |
| 10,874,570 B2 | 12/2020 | Lim et al. |
| 10,888,484 B2 * | 1/2021 | Lim ................. A61G 13/0036 |
| 10,893,996 B2 * | 1/2021 | Lim ................. A61B 34/30 |
| 10,898,401 B2 * | 1/2021 | Lim ................. A61G 13/08 |
| 10,900,448 B2 * | 1/2021 | Lim ................. A61G 13/04 |
| 2002/0138905 A1 | 10/2002 | Barltett et al. |
| 2002/0138906 A1 | 10/2002 | Barltett et al. |
| 2003/0140419 A1 | 7/2003 | Barltett et al. |
| 2003/0140420 A1 | 7/2003 | Niederkrom |
| 2003/0145382 A1 | 8/2003 | Krywiczanin |
| 2004/0010849 A1 | 1/2004 | Krywiczanin et al. |
| 2004/0133983 A1 | 7/2004 | Newkirk |
| 2005/0181917 A1 | 8/2005 | Dayal |
| 2006/0037141 A1 | 2/2006 | Krywiczanin et al. |
| 2006/0123546 A1 | 6/2006 | Horton |
| 2006/0162076 A1 | 7/2006 | Bartlett et al. |
| 2006/0162084 A1 | 7/2006 | Mezue |
| 2008/0134434 A1 | 6/2008 | Celauro |
| 2009/0070936 A1 | 3/2009 | Henderson |
| 2009/0139030 A1 | 6/2009 | Yang |
| 2009/0248041 A1 * | 10/2009 | Williams ............. A61B 8/12 606/130 |
| 2010/0037397 A1 | 2/2010 | Wood |
| 2010/0192300 A1 | 8/2010 | Tannoury |
| 2010/0293713 A1 | 11/2010 | Sharps |
| 2011/0030702 A1 | 2/2011 | Czajka, Jr. |
| 2011/0099716 A1 | 5/2011 | Jackson |
| 2012/0144589 A1 | 6/2012 | Skripps et al. |
| 2013/0111666 A1 | 5/2013 | Jackson |
| 2013/0247921 A1 | 9/2013 | Dye |
| 2013/0283526 A1 | 10/2013 | Gagliardi |
| 2013/0307298 A1 | 11/2013 | Meiki |
| 2014/0068861 A1 | 3/2014 | Jackson |
| 2014/0109316 A1 * | 4/2014 | Jackson ............. A61G 13/104 5/607 |
| 2014/0130258 A1 | 5/2014 | Kobuss |
| 2014/0137327 A1 | 5/2014 | Tannoury et al. |
| 2015/0044956 A1 | 2/2015 | Hacker |
| 2015/0272681 A1 | 10/2015 | Skripps et al. |
| 2016/0047394 A1 | 2/2016 | Lee et al. |
| 2016/0081582 A1 | 3/2016 | Rapoport |
| 2016/0089287 A1 | 3/2016 | Buerstner |
| 2016/0193099 A1 | 7/2016 | Drake |
| 2017/0027797 A1 | 2/2017 | Dolliver et al. |

(56) References Cited

U.S. PATENT DOCUMENTS

| | | |
|---|---|---|
| 2017/0049651 A1 | 2/2017 | Lim |
| 2017/0049653 A1 | 2/2017 | Lim |
| 2017/0079864 A1 | 3/2017 | Riley |
| 2017/0135891 A1 | 5/2017 | Kettner |
| 2017/0151115 A1* | 6/2017 | Jackson ................ A61G 7/008 |
| 2017/0341232 A1 | 11/2017 | Perplies |
| 2018/0116891 A1 | 5/2018 | Beale et al. |
| 2018/0185106 A1 | 7/2018 | Itkowitz |
| 2018/0185228 A1 | 7/2018 | Catacchio |
| 2018/0193104 A1 | 7/2018 | Beale et al. |
| 2018/0207044 A1 | 7/2018 | Sabet |
| 2018/0363596 A1 | 12/2018 | Lim et al. |
| 2019/0000702 A1 | 1/2019 | Lim et al. |
| 2019/0000707 A1* | 1/2019 | Lim .................... A61G 13/122 |
| 2019/0046381 A1 | 2/2019 | Lim et al. |
| 2019/0046383 A1 | 2/2019 | Lim et al. |
| 2019/0209409 A1 | 7/2019 | Jackson et al. |
| 2019/0374420 A1 | 12/2019 | Lehman |
| 2020/0000668 A1 | 1/2020 | Lim et al. |
| 2020/0060914 A1 | 2/2020 | Lim |
| 2020/0060915 A1 | 2/2020 | Lim |

FOREIGN PATENT DOCUMENTS

| | | |
|---|---|---|
| WO | 2007058673 | 5/2007 |
| WO | 2017031225 | 2/2017 |

\* cited by examiner

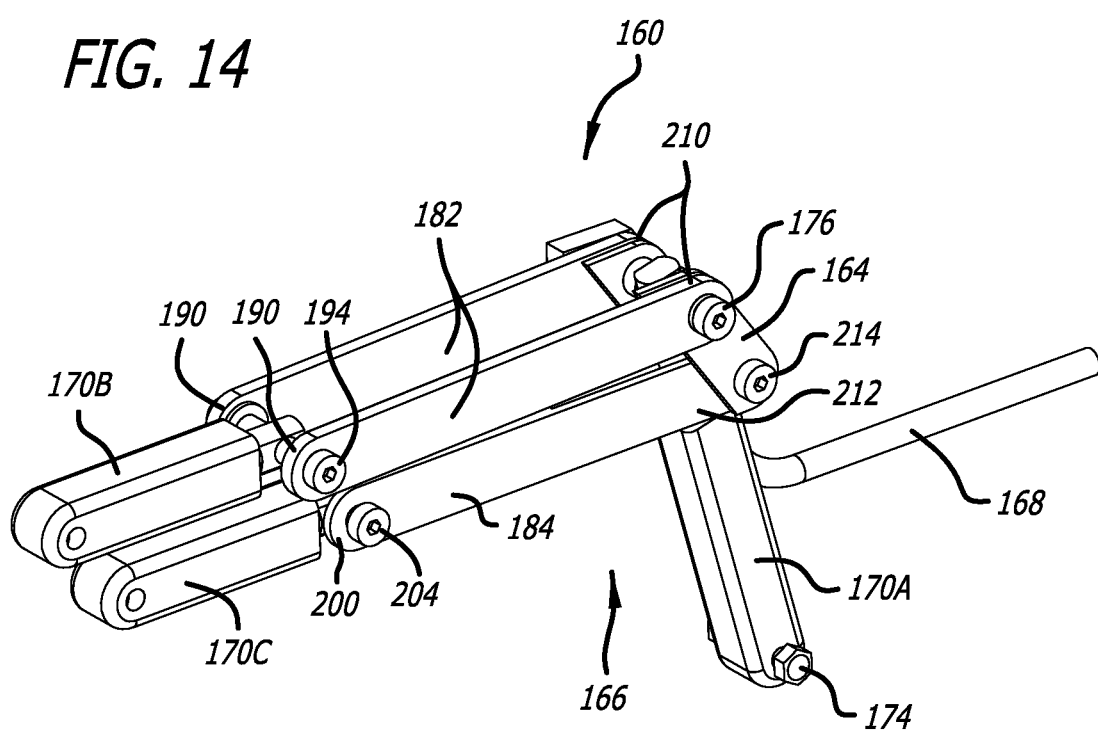

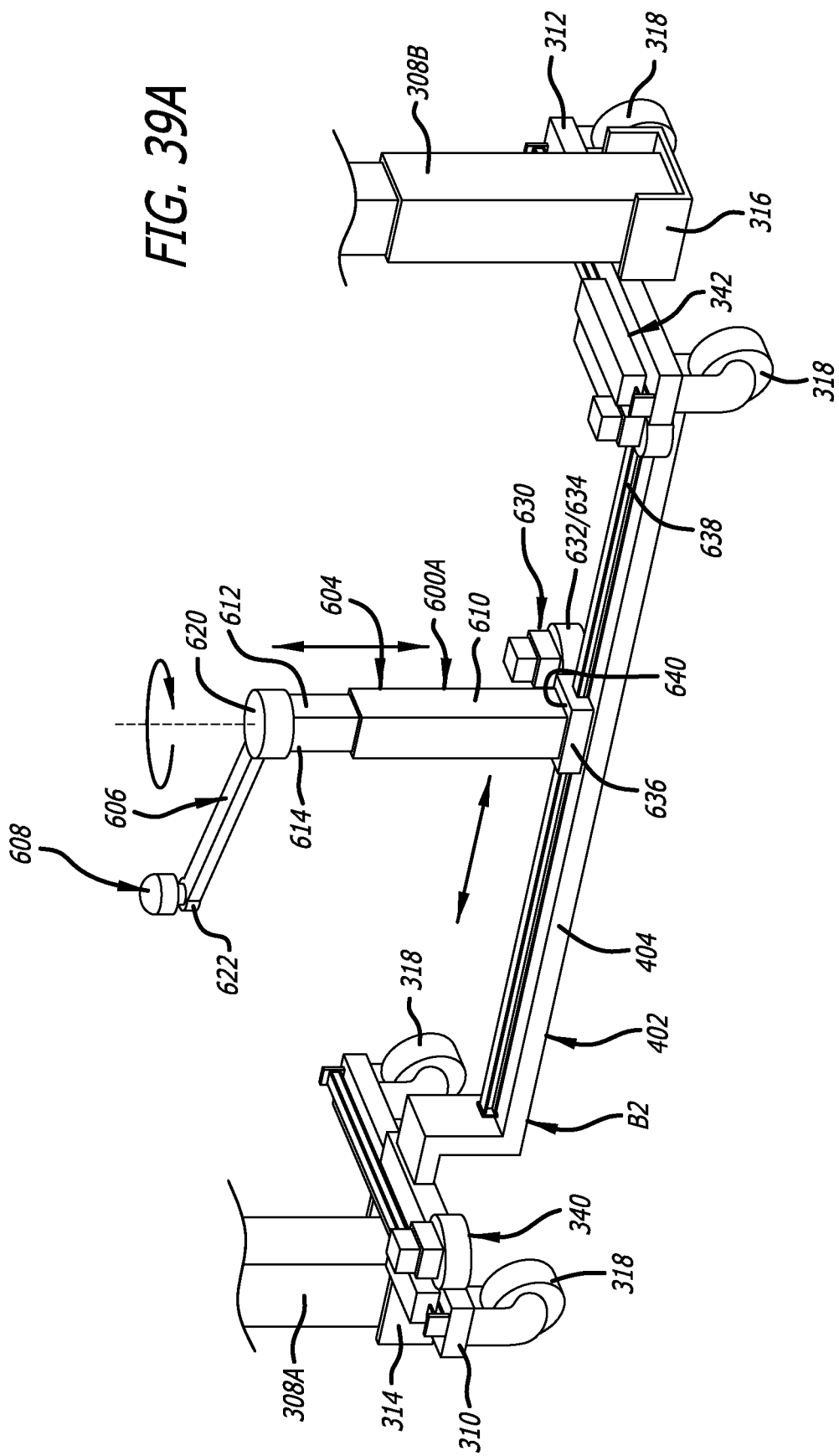

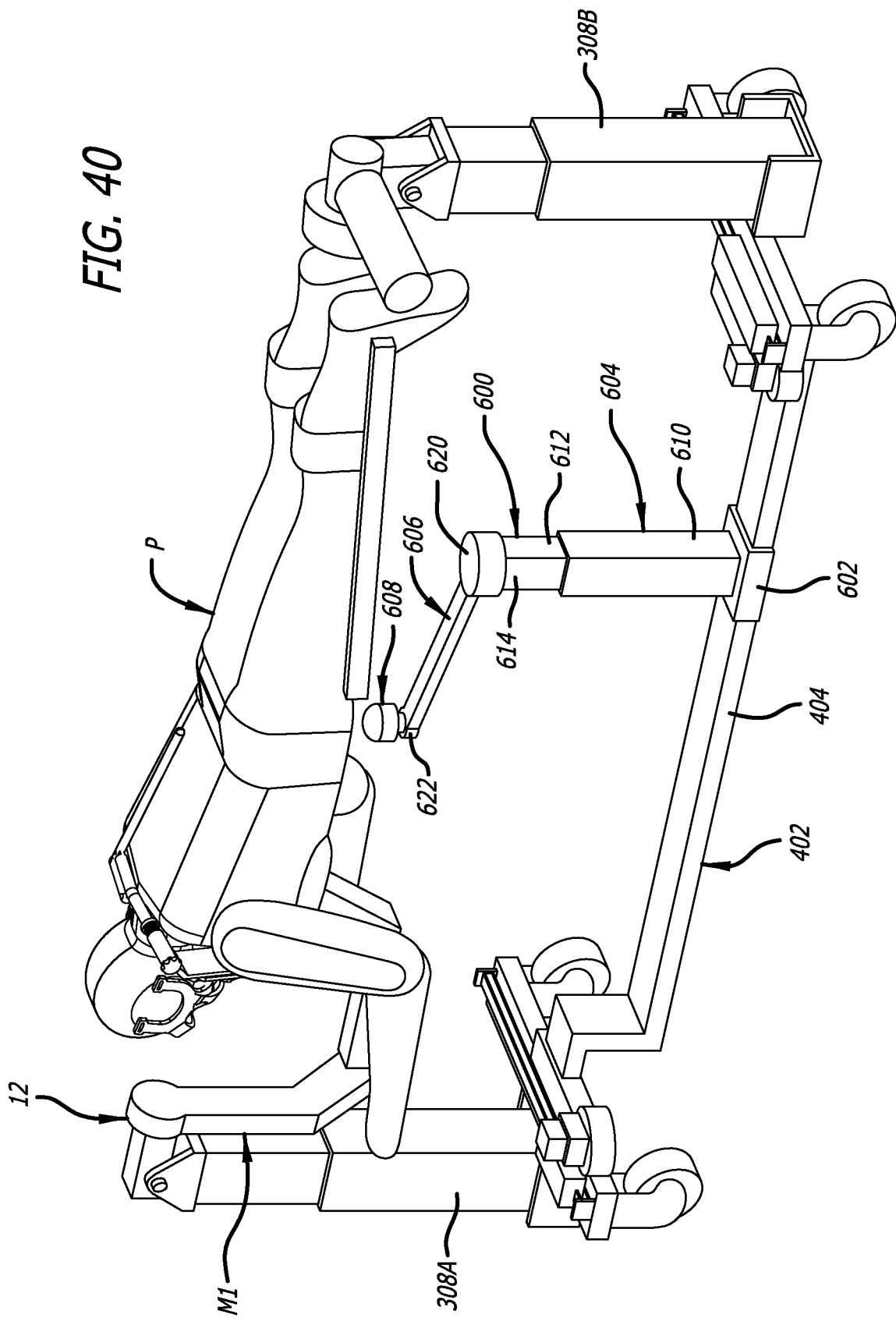

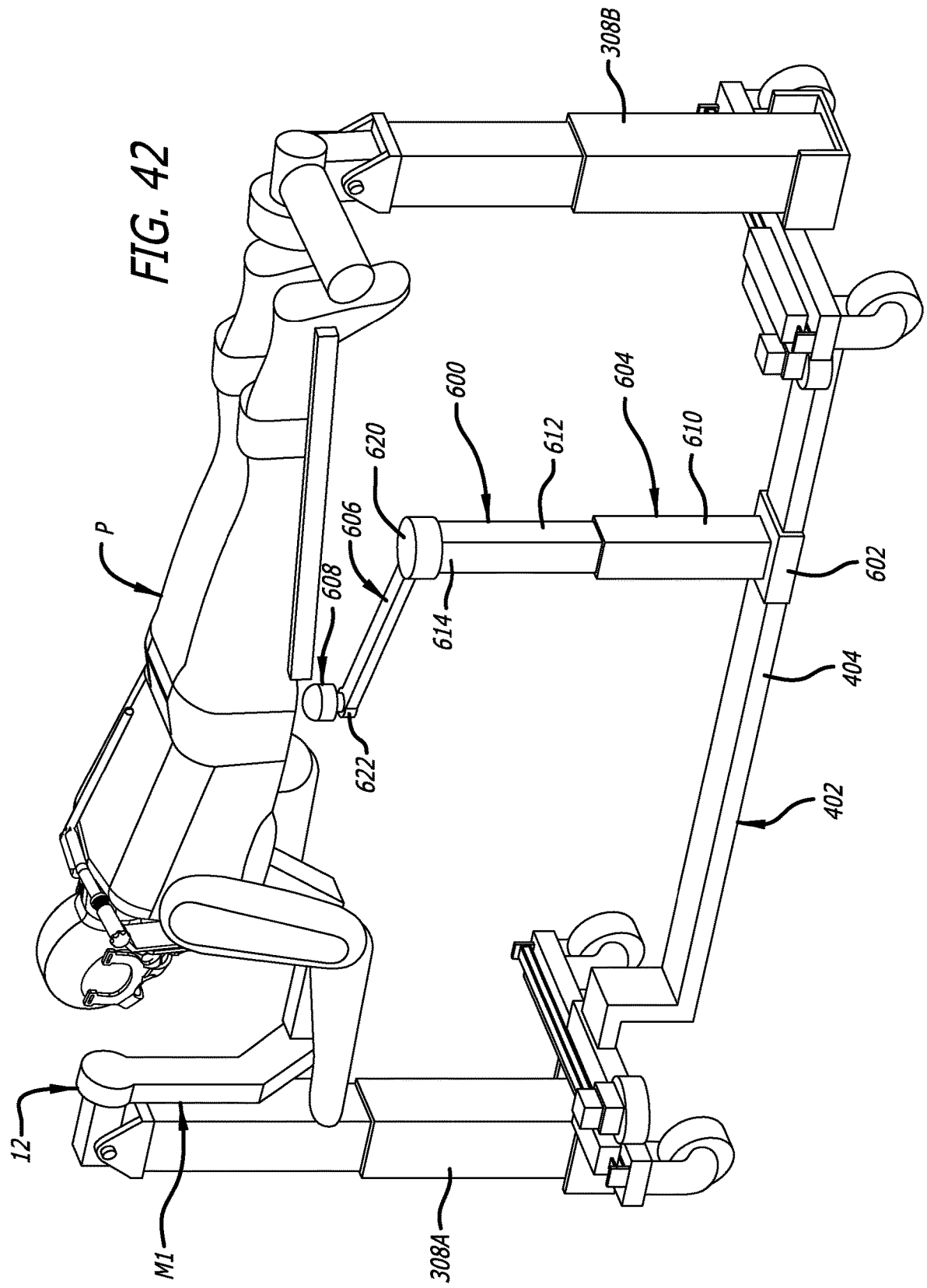

SURGICAL FRAME HAVING TRANSLATING LOWER BEAM AND MOVEABLE LINKAGE OR SURGICAL EQUIPMENT ATTACHED THERETO AND METHOD FOR USE THEREOF

The present application is a continuation of U.S. application Ser. No. 16/107,788, filed Aug. 21, 2018; all of which is incorporated by reference herein.

BACKGROUND OF THE INVENTION

Field of the Invention

The present invention relates to a surgical frame and a method for use thereof incorporating a translating lower beam and a linkage and/or surgical equipment supportively and moveably attached thereto. More particularly, the present invention relates to a surgical frame and a method for use thereof, where the surgical frame includes a translating lower beam that is moveable with respect to the remainder of the surgical frame, and a linkage and/or surgical equipment that are moveable relative to the translating lower beam. More specifically, the present invention relates to a surgical frame and a method for use thereof, where the surgical frame includes a translating lower beam that can be positioned and repositioned relative to the surgical frame, and the surgical frame further includes a linear movement mechanism for positioning and repositioning a linkage and/or surgical equipment supportively and moveably attached to the translating lower beam or interconnected with the translating lower beam via the linkage relative to the translating lower beam.

DESCRIPTION OF THE PRIOR ART

Surgical frames used to support patients thereon can include translating lower beams that can move relative to the remainder of the surgical frames. Such translating lower beams afford greater access to a patient receiving area to facilitate transfer to and from the surgical frame, and afford greater access to a patient by a surgeon and/or surgical assistant during surgery. Surgical equipment requiring support by moveable carts is oftentimes used during spinal surgery. Surgical equipment is oftentimes also attached directly to the surgical frames. However, moveable carts and surgical equipment attached directly to the surgical frames could potentially interfere with movement of a main beam or a translating lower beam during surgery. Therefore, there is need for a surgical frame moveably incorporating a linkage and/or surgical equipment supportively and moveably attached to the translating lower beam or interconnected with the translating lower beam via the linkage. For example, the interconnection of a cart with the translating lower beam via the linkage could allow the cart and any surgical equipment supported thereby to move so as to avoid interference with the main beam or the translating lower beam. The surgical frame could also include a linear movement mechanism facilitating movement of the linkage and/or the surgical equipment along the translating lower beam to afford movement thereof relative to the translating lower beam.

SUMMARY OF THE INVENTION

The present invention in one preferred embodiment contemplates a method of reconfiguring a surgical frame and positioning a cart interconnected with the surgical frame before, during, or after surgery including providing the surgical frame, the surgical frame including a support platform, a first support portion, a second support portion, and a main beam spaced from the ground by the support platform, the first support portion, and the second support portion, the support platform including a translating beam moveable relative to portions of the support platform between a first position at or adjacent a first lateral side of the surgical frame and a second position at or adjacent a second lateral side of the surgical frame, the support platform including a linkage for interconnecting the cart with the surgical frame, the linkage being moveable with respect to the translating beam between a first position at or adjacent a first end of the translating beam and a second position at or adjacent a second end of the translating beam, the main beam being configured to receive a patient thereon, the main beam and the patient received thereon being rotatable relative to the support platform, the first support portion, and the second support portion; providing the cart, the cart being interconnected with the surgical frame via the linkage, the cart being moveable via movement of the translating beam and the linkage, the cart supporting surgical equipment thereon; supporting the patient in a prone position by the main beam of the surgical frame; rotating the main beam from at least a first position supporting the patient in the prone position to a second position supporting the patient in one of an angled position and a lateral position; and moving the translating beam relative to the portions of the support platform and moving the linkage relative to the translating beam to prevent the cart from interfering with the rotation of the main beam.

The present invention in another preferred embodiment contemplates a method of reconfiguring a surgical frame and positioning a cart interconnected with the surgical frame before, during, or after surgery including providing the surgical frame, the surgical frame including at least a support platform and a moveable main beam, the support platform having a translating beam moveable relative to portions of the support platform between a first position at or adjacent a first lateral side of the surgical frame and a second position at or adjacent a second lateral side of the surgical frame, the support platform including a linkage for interconnecting the cart with the surgical frame, the linkage being moveable with respect to the translating beam between a first position at or adjacent a first end of the translating beam and a second position at or adjacent a second end of the translating beam, the main beam being configured to receive a patient thereon, the main beam and the patient received thereon being rotatable relative to the support platform; providing the cart, the cart being interconnected with the surgical frame via the linkage, the cart being moveable via movement of the translating beam and the linkage, the cart supporting surgical equipment thereon; supporting the patient in a prone position by the main beam of the surgical frame; rotating the main beam from at least a first position supporting the patient in the prone position to a second position supporting the patient in one of an angled position and a lateral position; and moving the translating beam relative to the portions of the support platform and moving the linkage relative to the translating beam to prevent the cart from interfering with the rotation of the main beam.

The present invention in yet another preferred embodiment contemplates a reconfigurable surgical frame and a surgical cart interconnected with the reconfigurable surgical frame, where the reconfigurable surgical frame includes a support platform, a first support portion, a second support portion, and a main beam spaced from the ground by the support platform, the first support portion, and the second support portion, the support platform including a translating beam moveable relative to portions of the support platform between a first position at or adjacent a first lateral side of the surgical frame and a second position at or adjacent a second lateral side of the surgical frame, and the support platform including a linkage and a linear movement mechanism, the linkage being moveable via actuation of the linear movement mechanism between a first position at or adjacent a first end of the translating beam and a second position at or adjacent a second end of the translating beam, the main beam being configured to receive a patient thereon, the main beam and the patient received thereon being rotatable relative to the support platform, the first support portion, and the second support portion from at least a first position supporting the patient in the prone position to a second position supporting the patient in one of an angled position and a lateral position; where the surgical cart is interconnected to the translating beam via the linkage, and the surgical cart including one or more casters affording movement thereof, and surgical robot supported thereon; and where, during rotation of the main beam between the first position and the second position thereof, the translating beam is moveable relative to the portions of the support platform and the linkage is moveable relative to the translating beam to prevent the cart from interfering with the rotation of the main beam.

These and other objects of the present invention will be apparent from review of the following specification and the accompanying drawings.

BRIEF DESCRIPTION OF THE DRAWINGS

FIG. 14 is a perspective view of a chest support lift mechanism of the torso-lift support of FIGS. 13A-13C with actuators thereof retracted;

FIG. 39A is a top side perspective view of a portion of the first side of the surgical frame of FIG. 32 depicting a second embodiment of a patient support arm supportively and moveably attached to the translating beam thereof;

FIG. 40 is a top side perspective view from the first side of the surgical frame of FIG. 32 with the patient positioned thereon in the prone position, a main beam being located in a first horizontal position at a first height, and the patient support arm being used to support the pelvis of the patient;

FIG. 42 is a top side perspective view from the first side of the surgical frame of FIG. 32 with the patient positioned thereon in the prone position, the main beam being located in a second horizontal position at a second height, and the patient support arm being used to support the pelvis of the patient.

DETAILED DESCRIPTION OF THE PREFERRED EMBODIMENT

Figure 1:
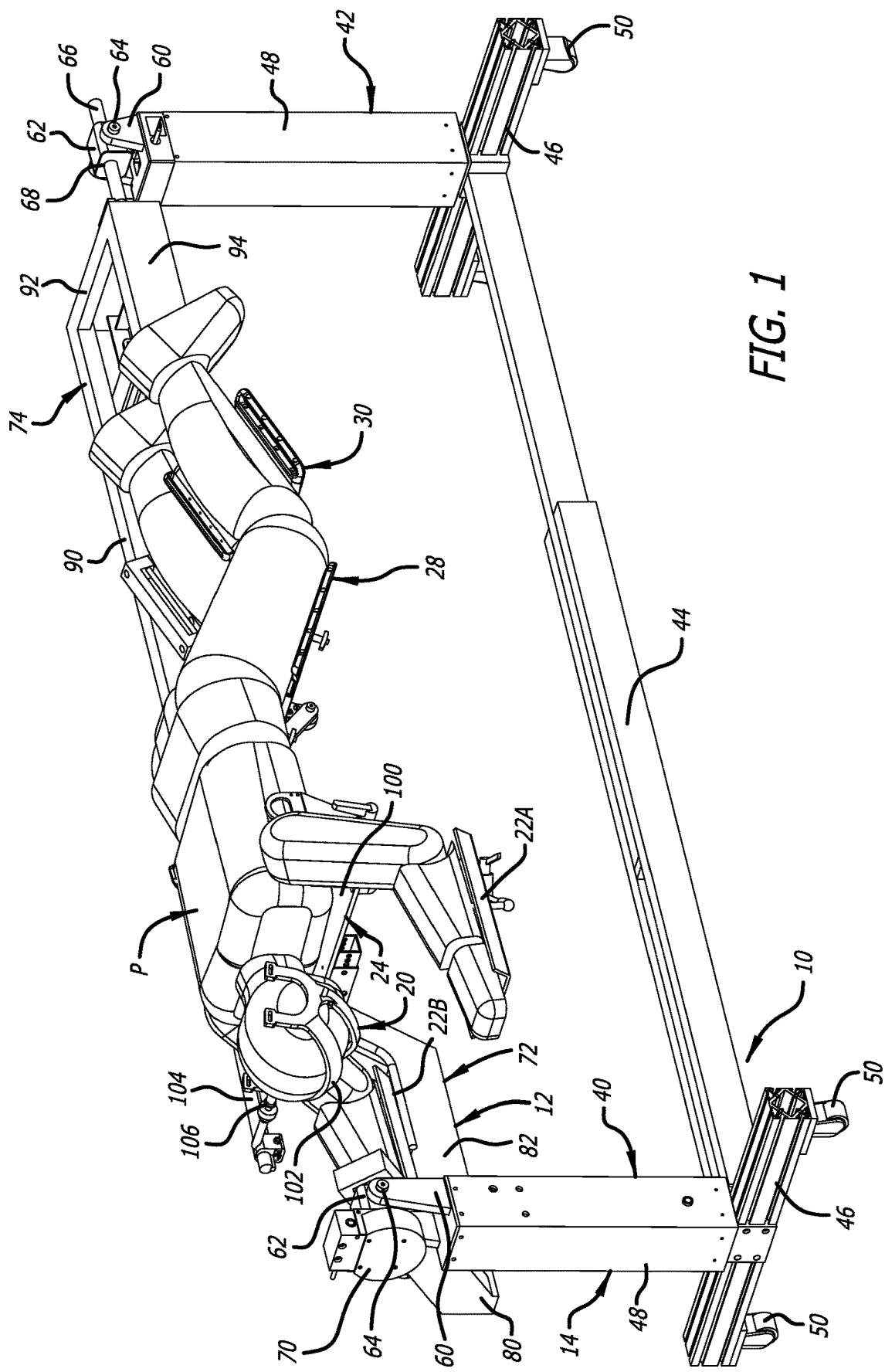
FIG. 1 is a top perspective view of a prior art surgical frame with a patient positioned thereon in a prone position.
Figure 2:
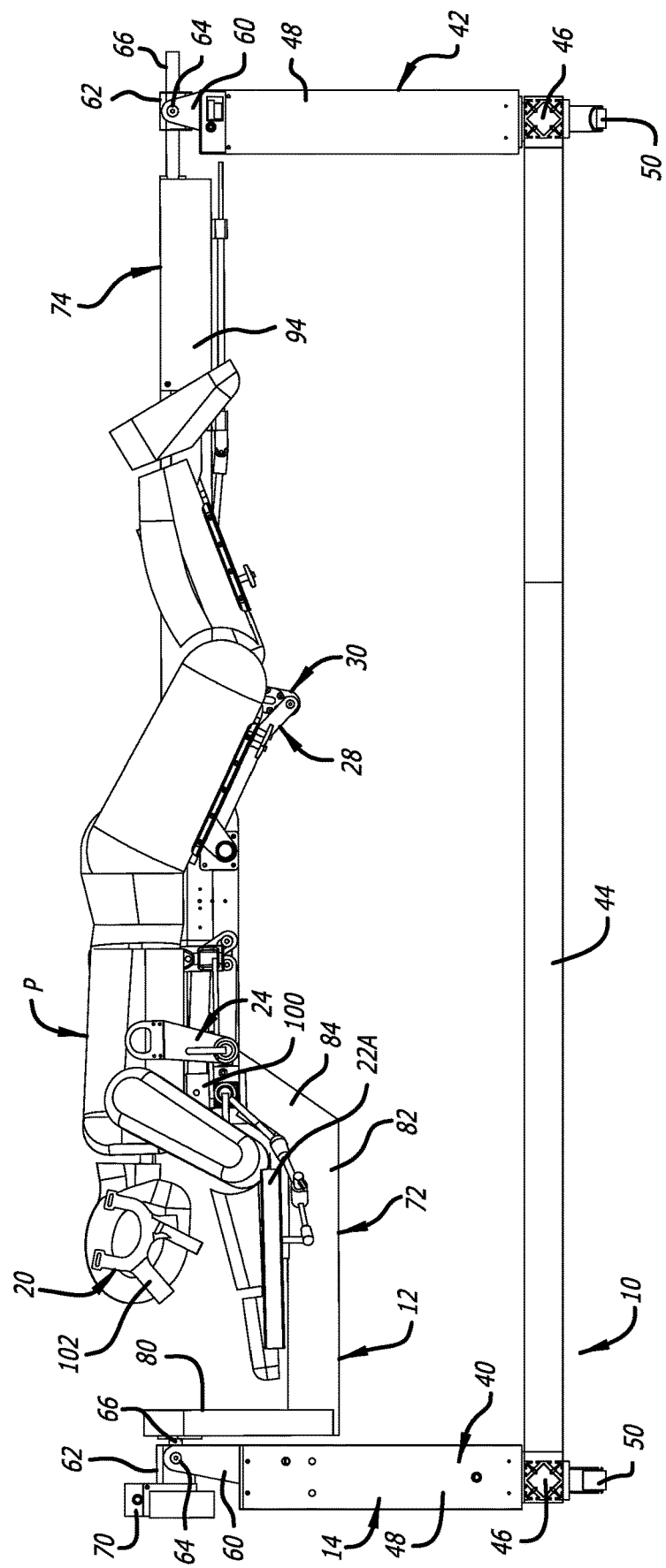
FIG. 2 is a side elevational view of the surgical frame of FIG. 1 with the patient positioned thereon in a prone position.
Figure 3:
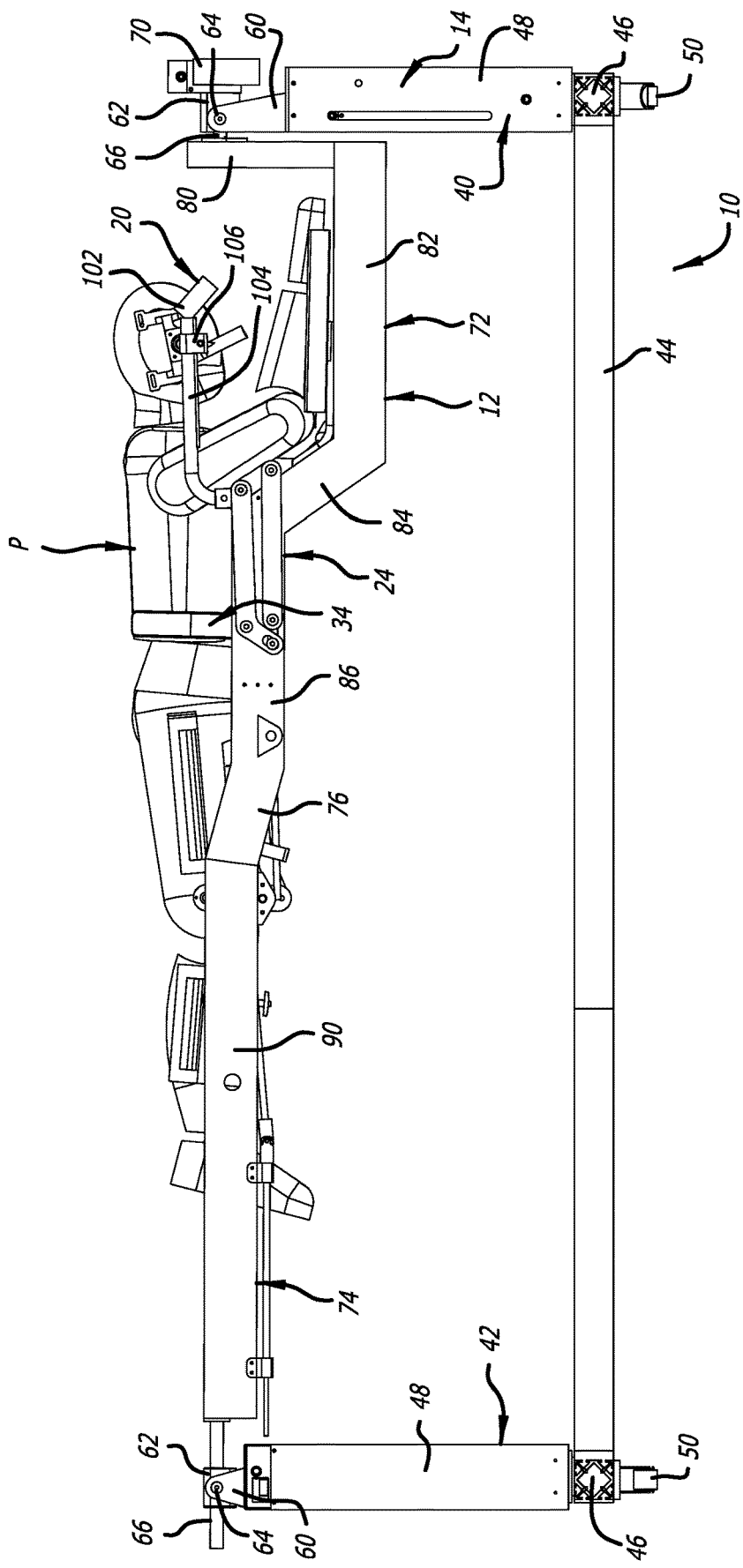
FIG. 3 is another side elevational view of the surgical frame of FIG. 1 with the patient positioned thereon in a prone position.

FIGS. 1-26 depict a prior art embodiment and components of a surgical support frame generally indicated by the numeral 10. FIGS. 1-26 were previously described in U.S. Ser. No. 15/239,256, which is hereby incorporated by reference herein in its entirety. Furthermore, FIGS. 27-30 were previously described in U.S. Ser. No. 15/639,080, which is hereby incorporated by reference herein in its entirety.

As discussed below, the surgical frame 10 serves as an exoskeleton to support the body of the patient P as the patient's body is manipulated thereby, and, in doing so, serves to support the patient P such that the patient's spine does not experience unnecessary torsion.

The surgical frame 10 is configured to provide a relatively minimal amount of structure adjacent the patient's spine to facilitate access thereto and to improve the quality of imaging available before and during surgery. Thus, the surgeon's workspace and imaging access are thereby increased. Furthermore, radio-lucent or low magnetic susceptibility materials can be used in constructing the structural components adjacent the patient's spine in order to further enhance imaging quality.

The surgical frame 10 has a longitudinal axis and a length therealong. As depicted in FIGS. 1-5, for example, the surgical frame 10 includes an offset structural main beam 12 and a support structure 14. The offset main beam 12 is spaced from the ground by the support structure 14. As discussed below, the offset main beam 12 is used in supporting the patient P on the surgical frame 10 and various support components of the surgical frame 10 that directly contact the patient P (such as a head support 20, arm supports 22A and 22B, torso-lift supports 24 and 160, a sagittal adjustment assembly 28 including a pelvic-tilt mechanism 30 and a leg adjustment mechanism 32, and a coronal adjustment assembly 34). As discussed below, an operator such as a surgeon can control actuation of the various support components to manipulate the position of the patient's body. Soft straps (not shown) are used with these various support components to secure the patient P to the frame and to enable either manipulation or fixation of the patient P. Reusable soft pads can be used on the load-bearing areas of the various support components.

Figure 4:
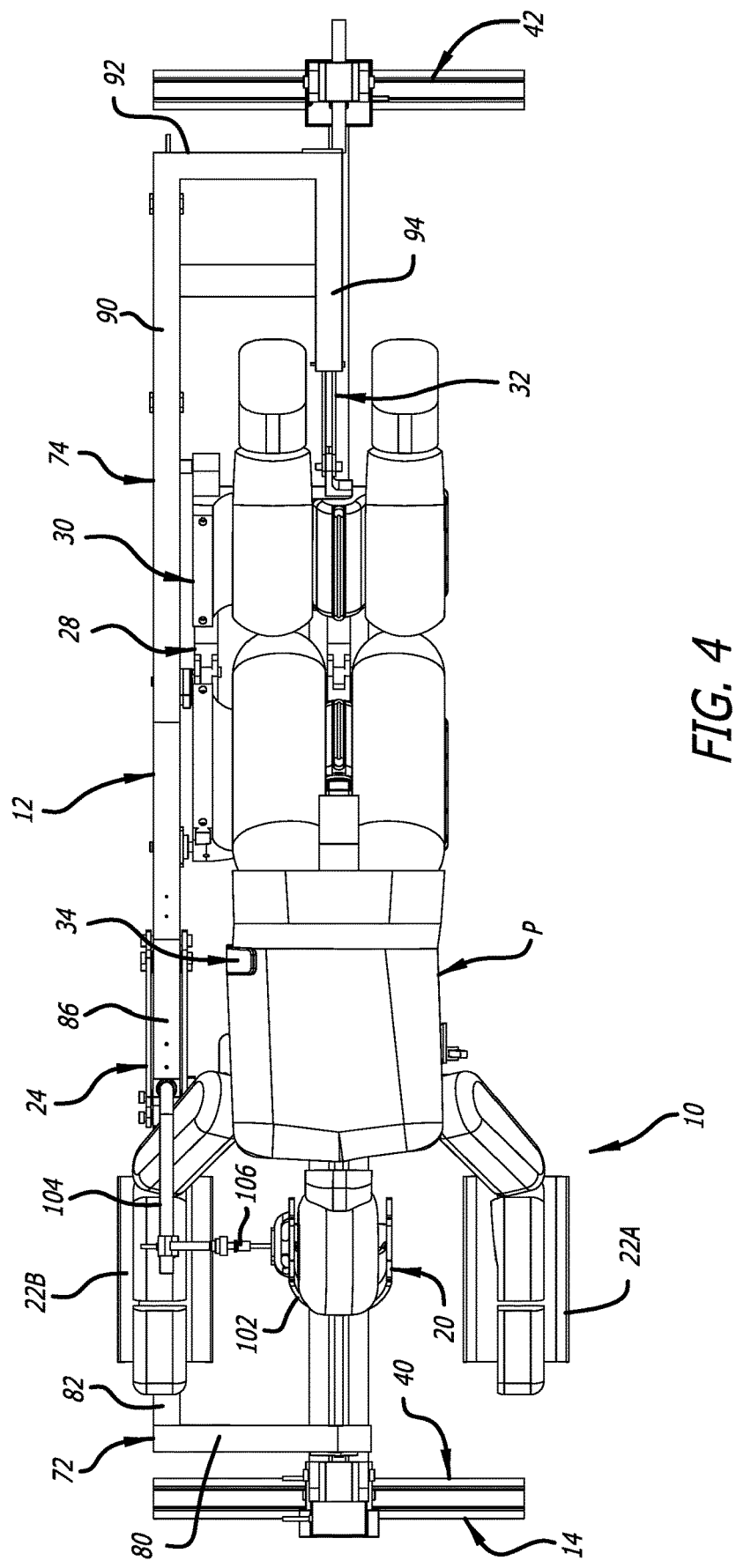
FIG. 4 is a top plan view of the surgical frame of FIG. 1 with the patient positioned thereon in a prone position.
Figure 5:
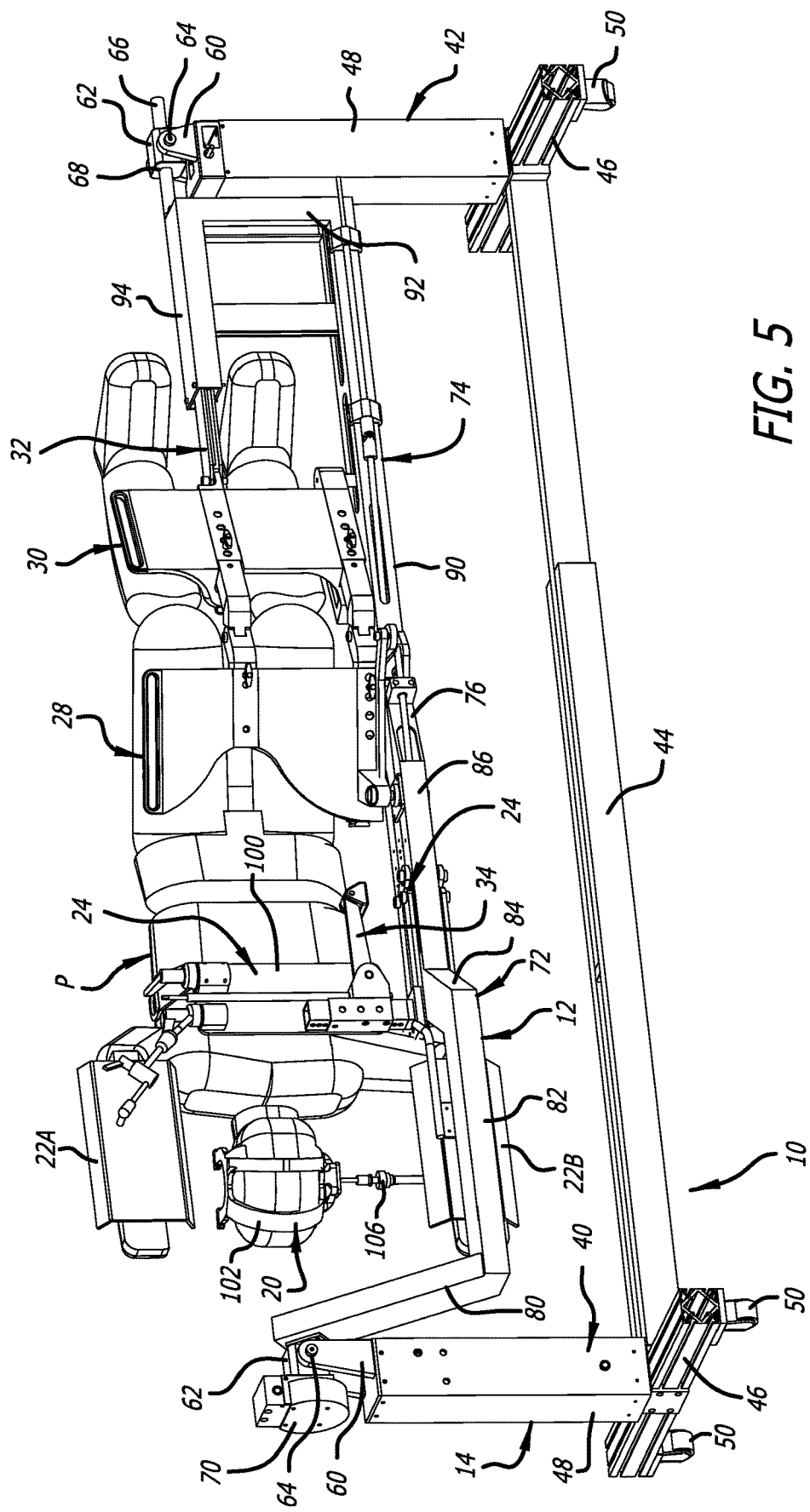
FIG. 5 is a top perspective view of the surgical frame of FIG. 1 with the patient positioned thereon in a lateral position.

The offset main beam 12 is used to facilitate rotation of the patient P. The offset main beam 12 can be rotated a full 360° before and during surgery to facilitate various positions of the patient P to afford various surgical pathways to the patient's spine depending on the surgery to be performed. For example, the offset main beam 12 can be positioned to place the patient P in a prone position (e.g., FIGS. 1-4), a lateral position (e.g., FIG. 5), and in a position 45° between the prone and lateral positions. Furthermore, the offset main beam 12 can be rotated to afford anterior, posterior, lateral, anterolateral, and posterolateral pathways to the spine. As such, the patient's body can be flipped numerous times before and during surgery without compromising sterility or safety. The various support components of the surgical frame 10 are strategically placed to further manipulate the patient's body into position before and during surgery. Such intraoperative manipulation and positioning of the patient P affords a surgeon significant access to the patient's body. To illustrate, when the offset main beam 12 is rotated to position the patient P in a lateral position, as depicted in FIG. 5, the head support 20, the arm supports 22A and 22B, the torso-lift support 24, the sagittal adjustment assembly 28, and/or the coronal adjustment assembly 34 can be articulated such that the surgical frame 10 is OLIF-capable or DLIF-capable.

As depicted in FIG. 1, for example, the support structure 14 includes a first support portion 40 and a second support portion 42 interconnected by a cross member 44. Each of the first and second support portions 40 and 42 include a horizontal portion 46 and a vertical support post 48. The horizontal portions 46 are connected to the cross member 44, and casters 50 can be attached to the horizontal portions 46 to facilitate movement of the surgical frame 10.

The vertical support posts 48 can be adjustable to facilitate expansion and contraction of the heights thereof. Expansion and contraction of the vertical support posts 48 facilitates raising and lowering, respectively, of the offset main beam 12. As such, the vertical support posts 48 can be adjusted to have equal or different heights. For example, the vertical support posts 48 can be adjusted such that the vertical support post 48 of the second support portion 42 is raised 12 inches higher than the vertical support post 48 of the first support portion 40 to place the patient P in a reverse Trendelenburg position.

Furthermore, cross member 44 can be adjustable to facilitate expansion and contraction of the length thereof. Expansion and contraction of the cross member 44 facilitates lengthening and shortening, respectively, of the distance between the first and second support portions 40 and 42.

The vertical support post 48 of the first and second support portions 40 and 42 have heights at least affording rotation of the offset main beam 12 and the patient P positioned thereon. Each of the vertical support posts 48 include a clevis 60, a support block 62 positioned in the clevis 60, and a pin 64 pinning the clevis 60 to the support block 62. The support blocks 62 are capable of pivotal movement relative to the clevises 60 to accommodate different heights of the vertical support posts 48. Furthermore, axles 66 extending outwardly from the offset main beam 12 are received in apertures 68 formed the support blocks 62. The axles 66 define an axis of rotation of the offset main beam 12, and the interaction of the axles 66 with the support blocks 62 facilitate rotation of the offset main beam 12.

Furthermore, a servomotor 70 can be interconnected with the axle 66 received in the support block 62 of the first support portion 40. The servomotor 70 can be computer controlled and/or operated by the operator of the surgical frame 10 to facilitate controlled rotation of the offset main beam 12. Thus, by controlling actuation of the servomotor 70, the offset main beam 12 and the patient P supported thereon can be rotated to afford the various surgical pathways to the patient's spine.

As depicted in FIGS. 1-5, for example, the offset main beam 12 includes a forward portion 72 and a rear portion 74. The forward portion 72 supports the head support 20, the arm supports 22A and 22B, the torso-lift support 24, and the coronal adjustment assembly 34, and the rear portion 74 supports the sagittal adjustment assembly 28. The forward and rear portions 72 and 74 are connected to one another by connection member 76 shared therebetween. The forward portion 72 includes a first portion 80, a second portion 82, a third portion 84, and a fourth portion 86. The first portion 80 extends transversely to the axis of rotation of the offset main beam 12, and the second and fourth portions 82 and 86 are aligned with the axis of rotation of the offset main beam 12. The rear portion 74 includes a first portion 90, a second portion 92, and a third portion 94. The first and third portions 90 and 94 are aligned with the axis of rotation of the offset main beam 12, and the second portion 92 extends transversely to the axis of rotation of the offset main beam 12.

The axles 66 are attached to the first portion 80 of the forward portion 72 and to the third portion 94 of the rear portion 74. The lengths of the first portion 80 of the forward portion 72 and the second portion 92 of the rear portion 74 serve in offsetting portions of the forward and rear portions 72 and 74 from the axis of rotation of the offset main beam 12. This offset affords positioning of the cranial-caudal axis of patient P approximately aligned with the axis of rotation of the offset main beam 12.

Programmable settings controlled by a computer controller (not shown) can be used to maintain an ideal patient height for a working position of the surgical frame 10 at a near-constant position through rotation cycles, for example, between the patient positions depicted in FIGS. 1 and 5. This allows for a variable axis of rotation between the first portion 40 and the second portion 42.

Figure 6:
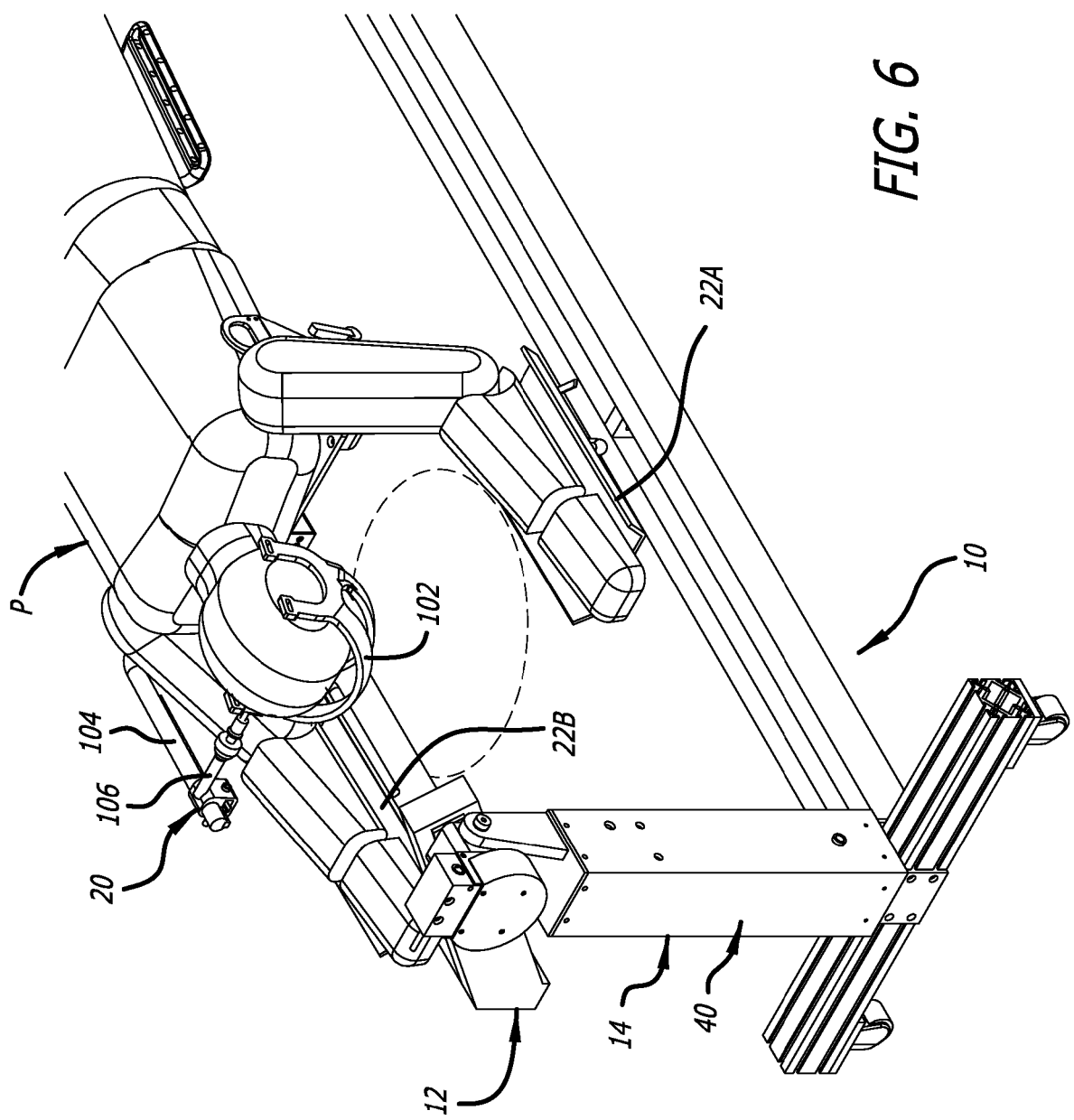
FIG. 6 is a top perspective view of portions of the surgical frame of FIG. 1 showing an area of access to the head of the patient positioned thereon in a prone position.

As depicted in FIG. 5, for example, the head support 20 is attached to a chest support plate 100 of the torso-lift support 24 to support the head of the patient P. If the torso-lift support 24 is not used, the head support 20 can be directly attached to the forward portion 72 of the offset main beam 12. As depicted in FIGS. 4 and 6, for example, the head support 20 further includes a facial support cradle 102, an axially adjustable head support beam 104, and a temple support portion 106. Soft straps (not shown) can be used to secure the patient P to the head support 20. The facial support cradle 102 includes padding across the forehead and cheeks, and provides open access to the mouth of the patient P. The head support 20 also allows for imaging access to the cervical spine. Adjustment of the head support 20 is possible via adjusting the angle and the length of the head support beam 104 and the temple support portion 106.

As depicted in FIG. 5, for example, the arm supports 22A and 22B contact the forearms and support the remainder of the arms of the patient P, with the first arm support 22A and the second arm support 22B attached to the chest support plate 100 of the torso-lift support 24. If the torso-lift support 24 is not used, the arm supports 22A and 22B can both be directly attached to the offset main beam 12. The arm supports 22A and 22B are positioned such that the arms of the patient P are spaced away from the remainder of the patient's body to provide access (FIG. 6) to at least portions of the face and neck of the patient P, thereby providing greater access to the patient.

Figure 7:
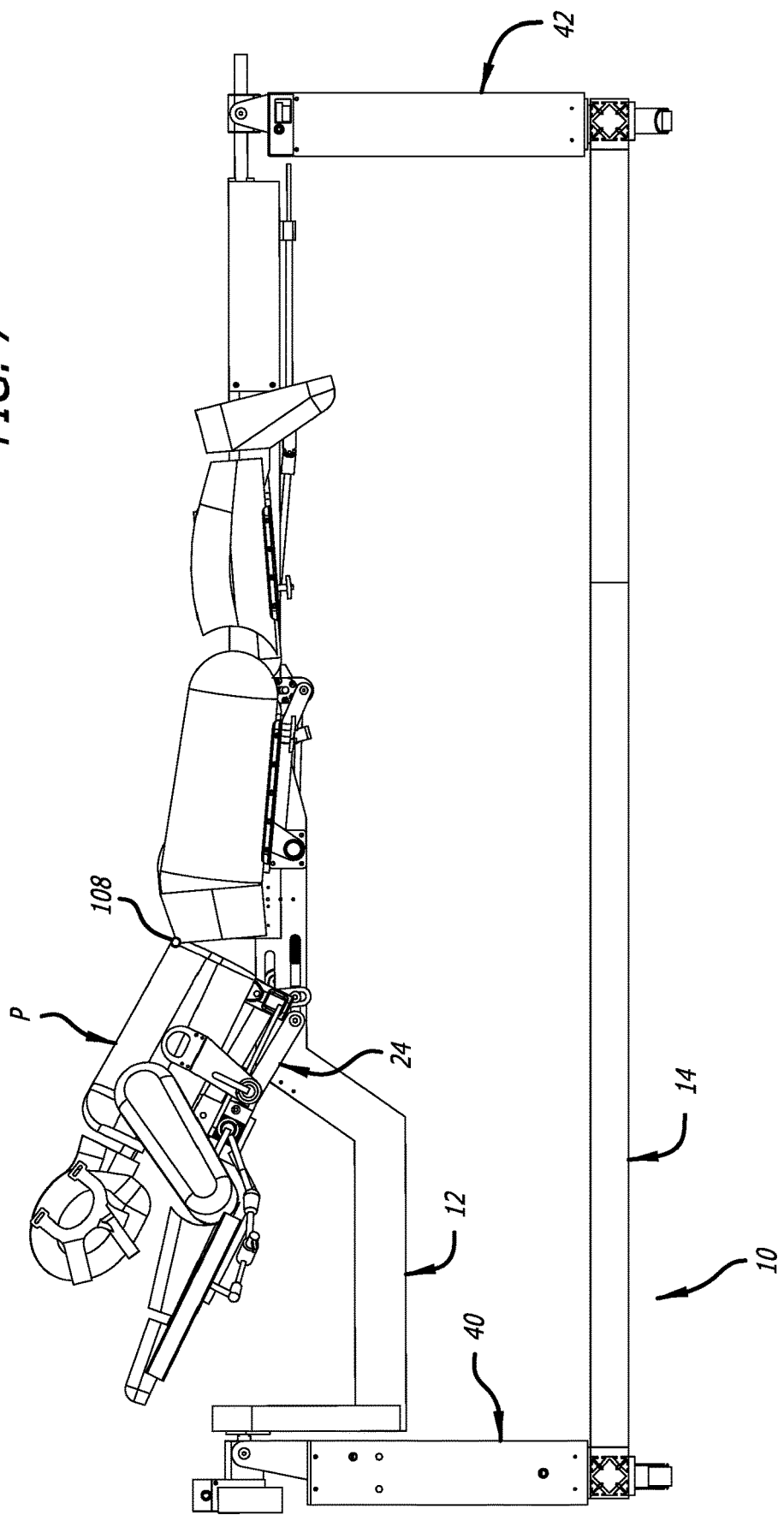
FIG. 7 is a side elevational view of the surgical frame of FIG. 1 showing a torso-lift support supporting the patient in a lifted position.
Figure 8:
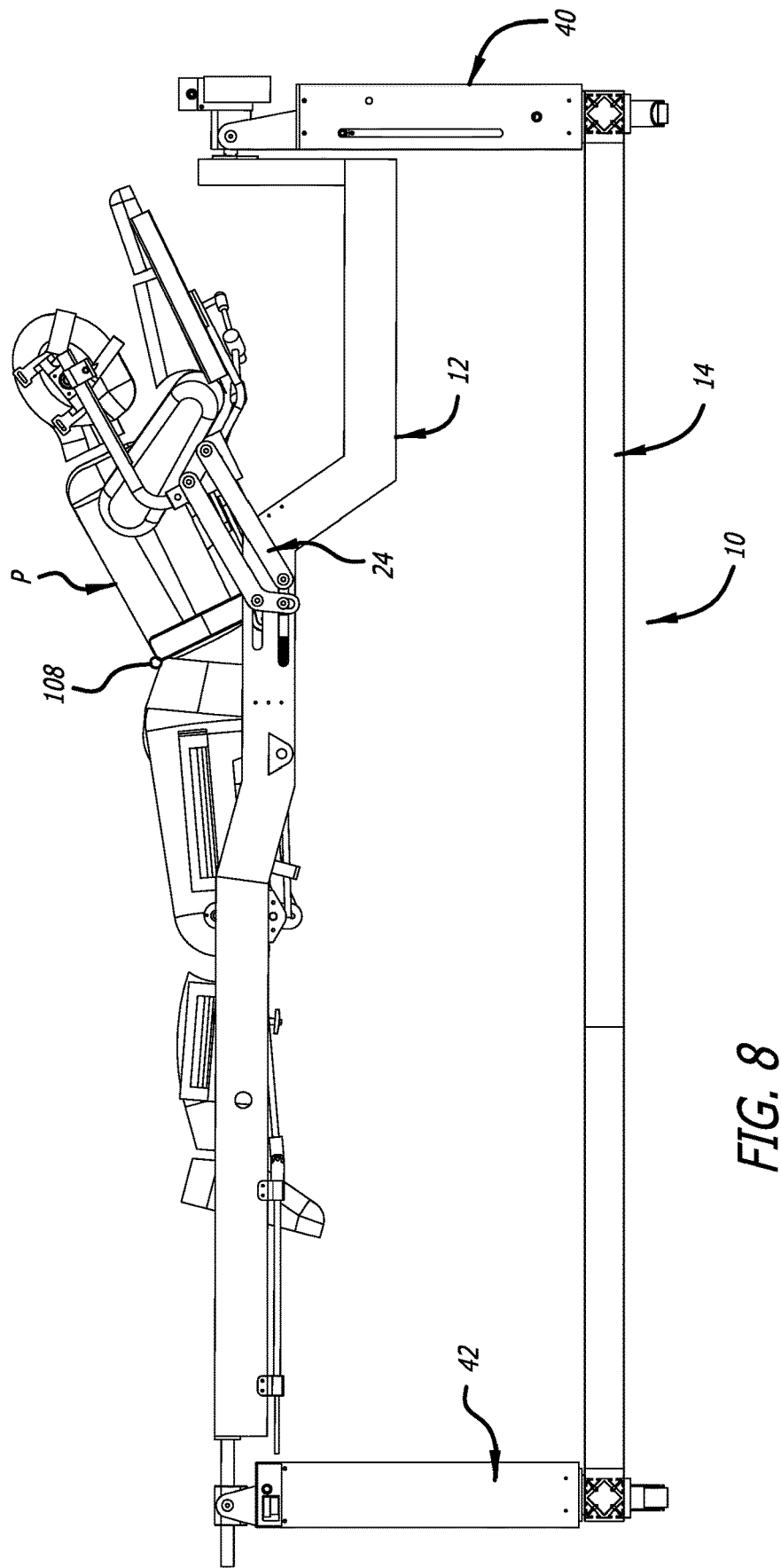
FIG. 8 is another side elevational view of the surgical frame of FIG. 1 showing the torso-lift support supporting the patient in the lifted position.
Figure 9:
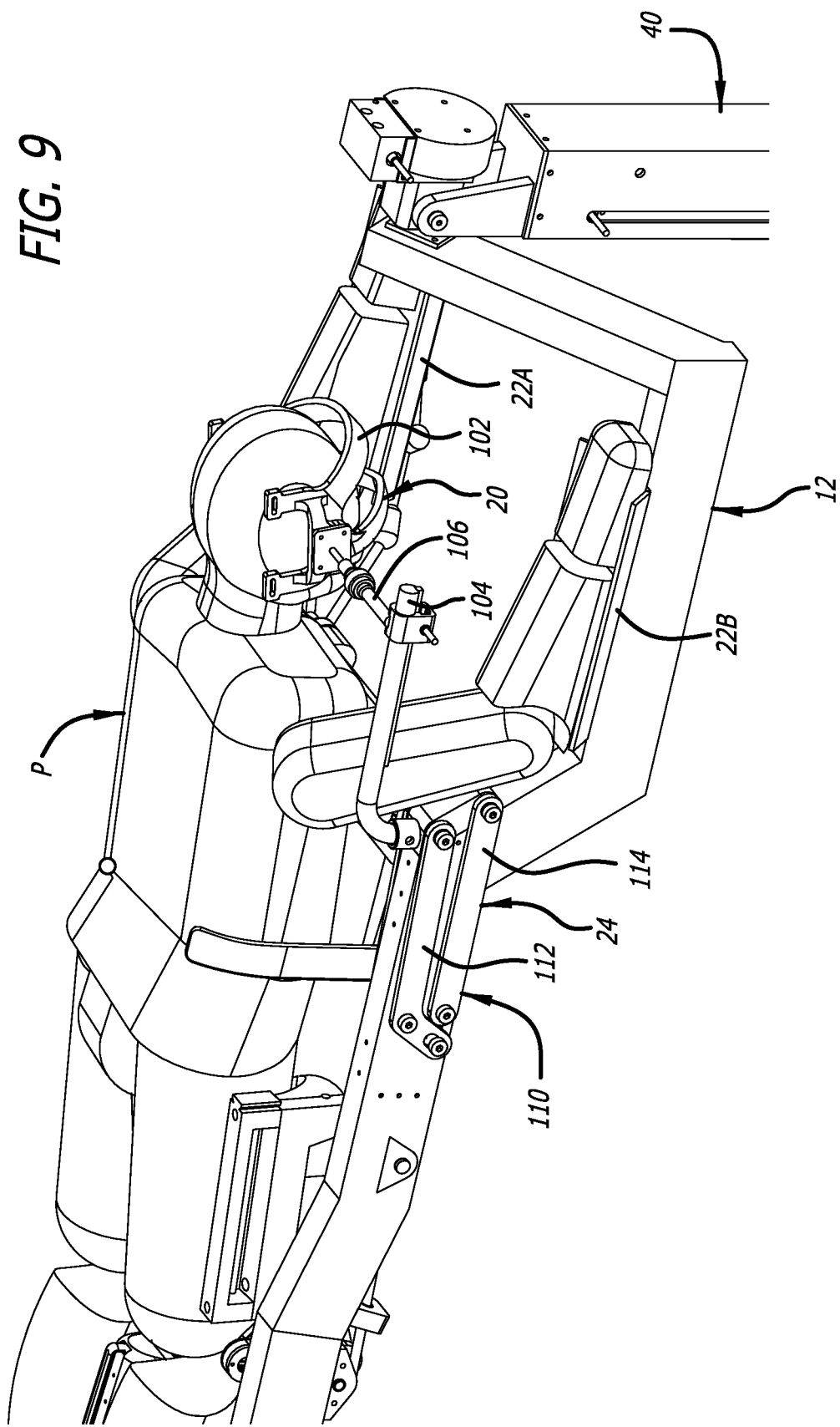
FIG. 9 is an enlarged top perspective view of portions of the surgical frame of FIG. 1 showing the torso-lift support supporting the patient in an unlifted position.

As depicted in FIGS. 7-12, for example, the surgical frame 10 includes a torso-lift capability for lifting and lowering the torso of the patient P between an uplifted position and a lifted position, which is described in detail below with respect to the torso-lift support 24. As depicted in FIGS. 7 and 8, for example, the torso-lift capability has an approximate center of rotation ("COR") 108 that is located at a position anterior to the patient's spine about the L2 of the lumbar spine, and is capable of elevating the upper body of the patient at least an additional six inches when measured at the chest support plate 100.

As depicted in FIGS. 9-12, for example, the torso-lift support 24 includes a "crawling" four-bar mechanism 110 attached to the chest support plate 100. Soft straps (not shown) can be used to secure the patient P to the chest support plate 100. The head support 20 and the arm supports 22A and 22B are attached to the chest support plate 100, thereby moving with the chest support plate 100 as the chest support plate 100 is articulated using the torso-lift support 24. The fixed COR 108 is defined at the position depicted in FIGS. 7 and 8. Appropriate placement of the COR 108 is important so that spinal cord integrity is not compromised (i.e., overly compressed or stretched) during the lift maneuver performed by the torso-lift support 24.

Figure 10:
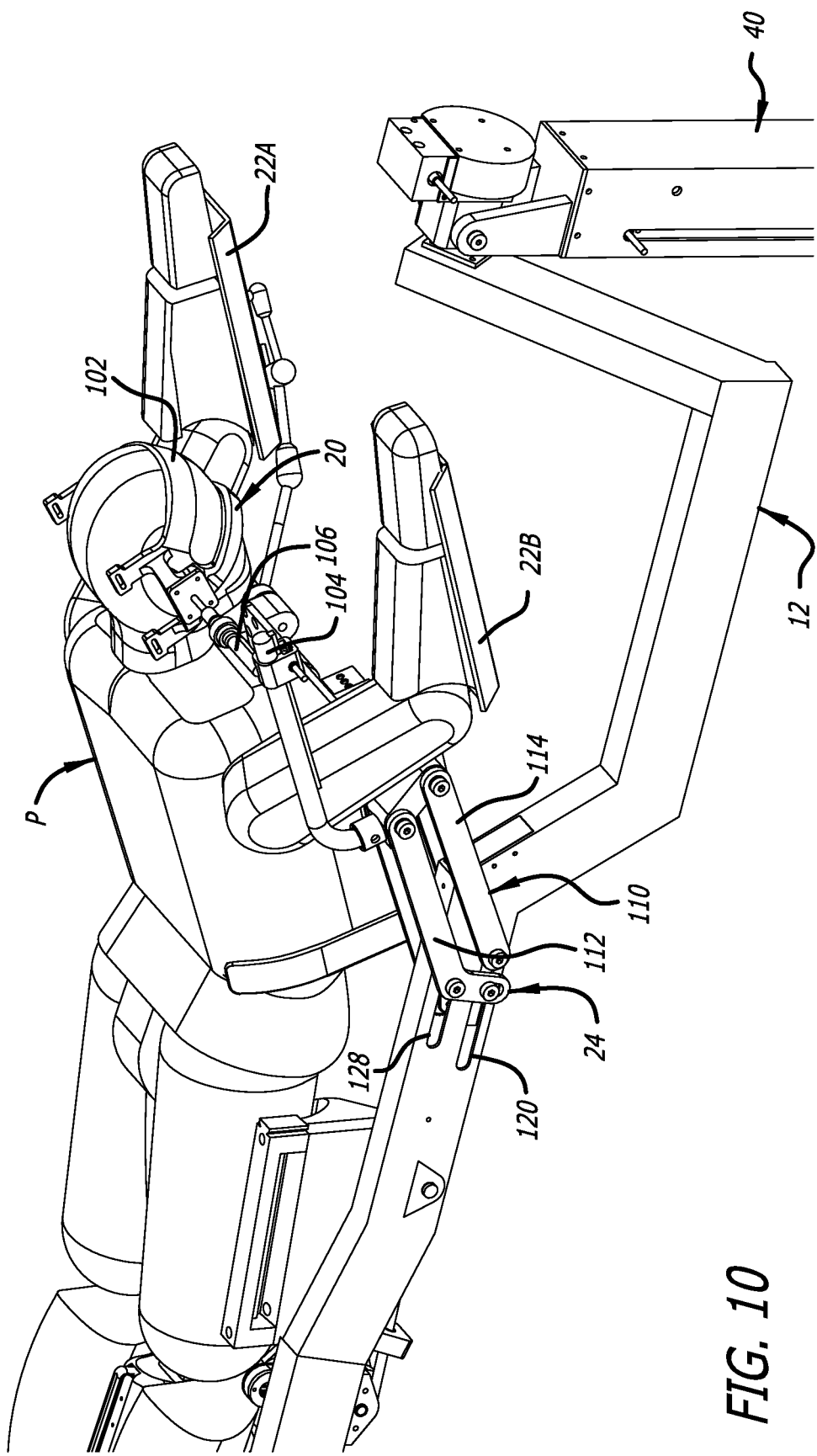
FIG. 10 is an enlarged top perspective view of portions of the surgical frame of FIG. 1 showing the torso-lift support supporting the patient in the lifted position.
Figure 11:
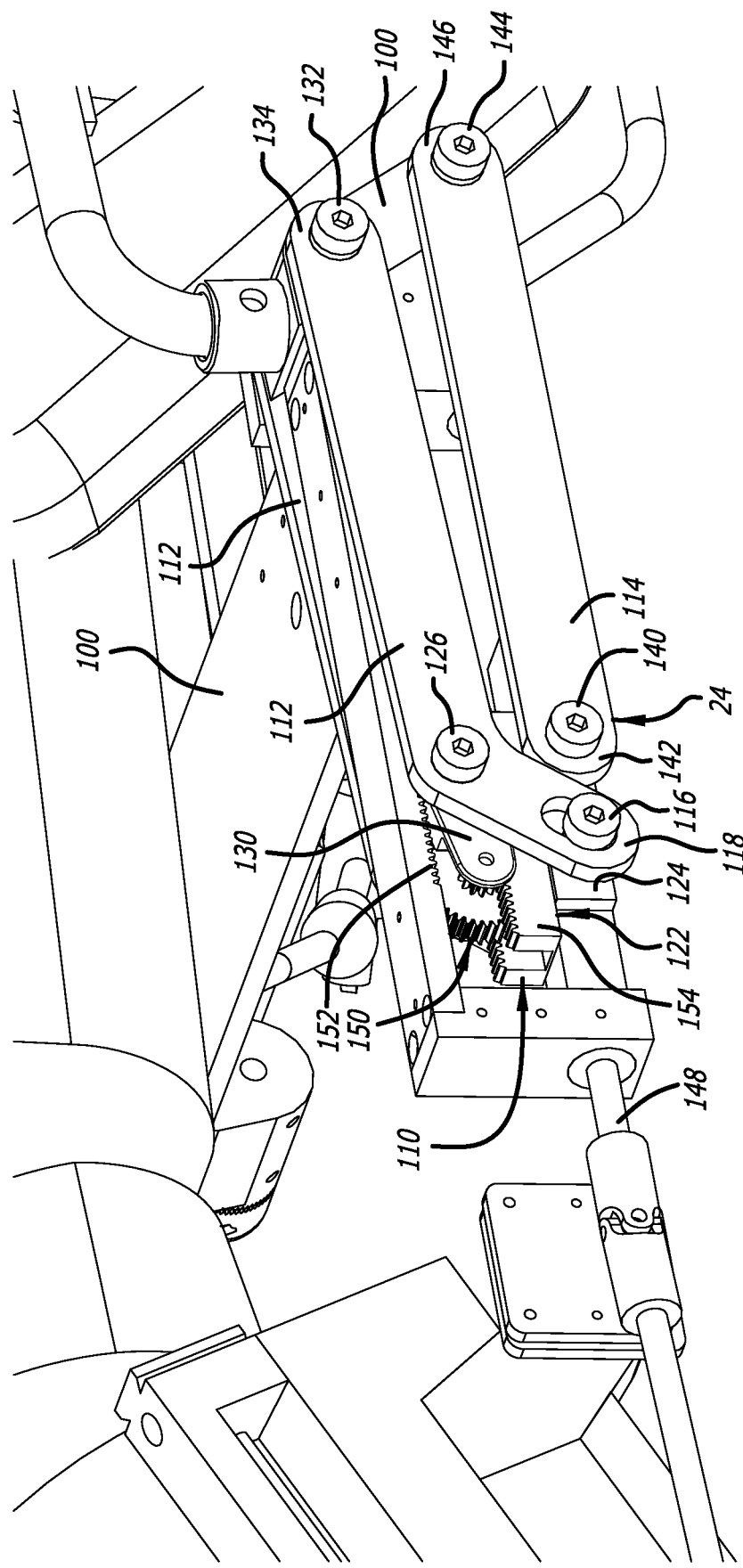
FIG. 11 is an enlarged top perspective view of componentry of the torso-lift support in the unlifted position.
Figure 12:
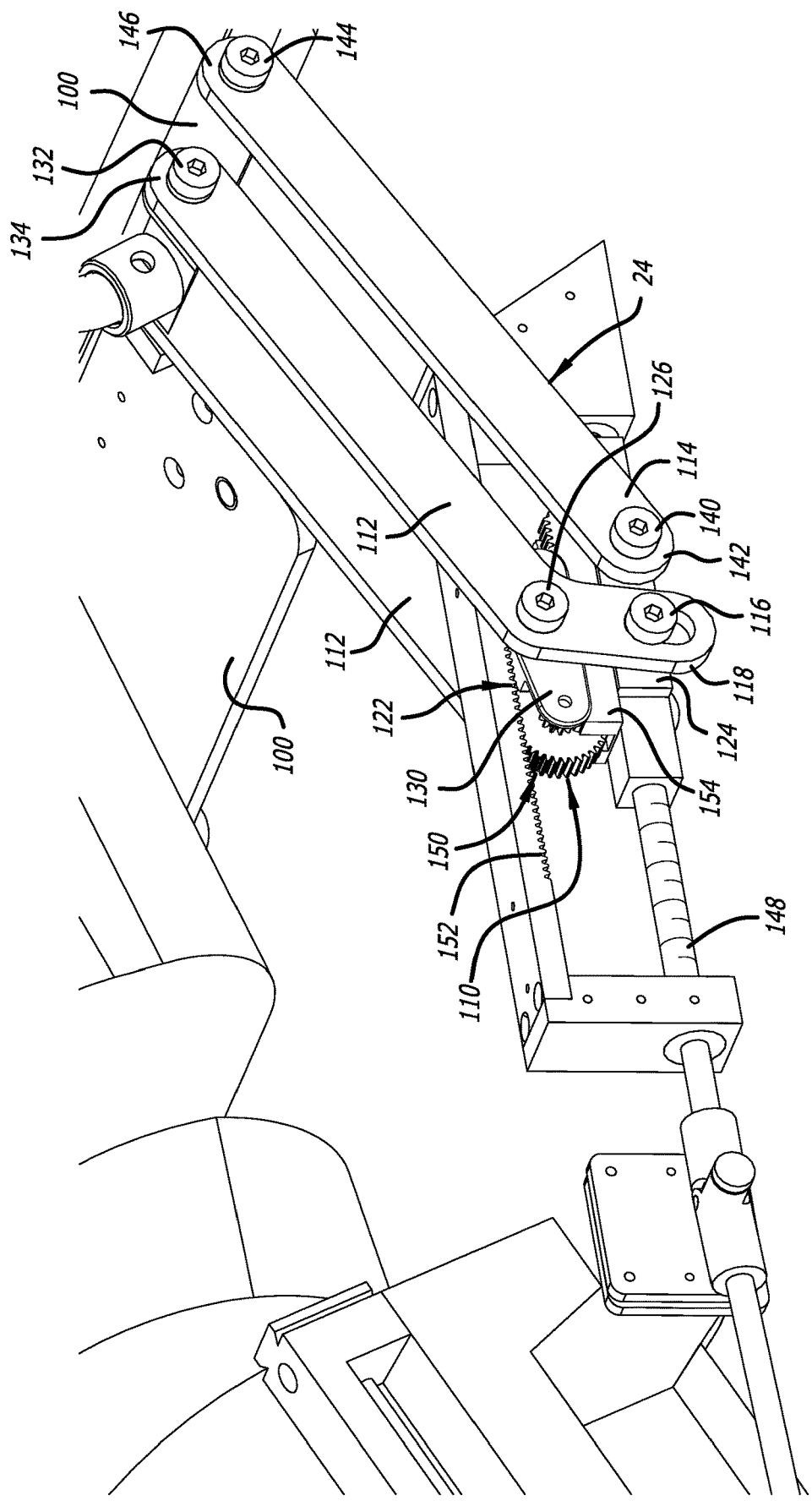
FIG. 12 is an enlarged top perspective view of the componentry of the torso-lift support in the lifted position.

As depicted in FIGS. 10-12, for example, the four-bar mechanism 110 includes first links 112 pivotally connected between offset main beam 12 and the chest support plate 100, and second links 114 pivotally connected between the offset main beam 12 and the chest support plate 100. As depicted in FIGS. 11 and 12, for example, in order to maintain the COR 108 at the desired fixed position, the first and second links 112 and 114 of the four-bar mechanism 110 crawl toward the first support portion 40 of the support structure 14, when the patient's upper body is being lifted. The first and second links 112 and 114 are arranged such that neither the surgeon's workspace nor imaging access are compromised while the patient's torso is being lifted.

As depicted in FIGS. 11 and 12, for example, each of the first links 112 define an L-shape, and includes a first pin 116 at a first end 118 thereof. The first pin 116 extends through first elongated slots 120 defined in the offset main beam 12, and the first pin 116 connects the first links 112 to a dual rack and pinion mechanism 122 via a drive nut 124 provided within the offset main beam 12, thus defining a lower pivot point thereof. Each of the first links 112 also includes a second pin 126 positioned proximate the corner of the L-shape. The second pin 126 extends through second elongated slots 128 defined in the offset main beam 12, and is linked to a carriage 130 of rack and pinion mechanism 122. Each of the first links 112 also includes a third pin 132 at a second end 134 that is pivotally attached to chest support plate 100, thus defining an upper pivot point thereof.

As depicted in FIGS. 11 and 12, for example, each of the second links 114 includes a first pin 140 at a first end 142 thereof. The first pin 140 extends through the first elongated slot 120 defined in the offset main beam 12, and the first pin 140 connects the second links 114 to the drive nut 124 of the rack and pinion mechanism 122, thus defining a lower pivot point thereof. Each of the second links 114 also includes a second pin 144 at a second end 146 that is pivotally connected to the chest support plate 100, thus defining an upper pivot point thereof.

As depicted in FIGS. 11 and 12, the rack and pinion mechanism 122 includes a drive screw 148 engaging the drive nut 124. Coupled gears 150 are attached to the carriage 130. The larger of the gears 150 engage an upper rack 152 (fixed within the offset main beam 12), and the smaller of the gears 150 engage a lower rack 154. The carriage 130 is defined as a gear assembly that floats between the two racks 152 and 154.

As depicted in FIGS. 11 and 12, the rack and pinion mechanism 122 converts rotation of the drive screw 148 into linear translation of the first and second links 112 and 114 in the first and second elongated slots 120 and 128 toward the first portion 40 of the support structure 14. As the drive nut 124 translates along drive screw 148 (via rotation of the drive screw 148), the carriage 130 translates towards the first portion 40 with less travel due to the different gear sizes of the coupled gears 150. The difference in travel, influenced by different gear ratios, causes the first links 112 pivotally attached thereto to lift the chest support plate 100. Lowering of the chest support plate 100 is accomplished by performing this operation in reverse. The second links 114 are "idler" links (attached to the drive nut 124 and the chest support plate 100) that controls the tilt of the chest support plate 100 as it is being lifted and lowered. All components associated with lifting while tilting the chest plate predetermine where COR 108 resides. Furthermore, a servomotor (not shown) interconnected with the drive screw 148 can be computer controlled and/or operated by the operator of the surgical frame 10 to facilitate controlled lifting and lowering of the chest support plate 100. A safety feature can be provided, enabling the operator to read and limit a lifting and lowering force applied by the torso-lift support 24 in order to prevent injury to the patient P. Moreover, the torso-lift support 24 can also include safety stops (not shown) to prevent over-extension or compression of the patient P, and sensors (not shown) programmed to send patient position feedback to the safety stops.

Figure 13A:
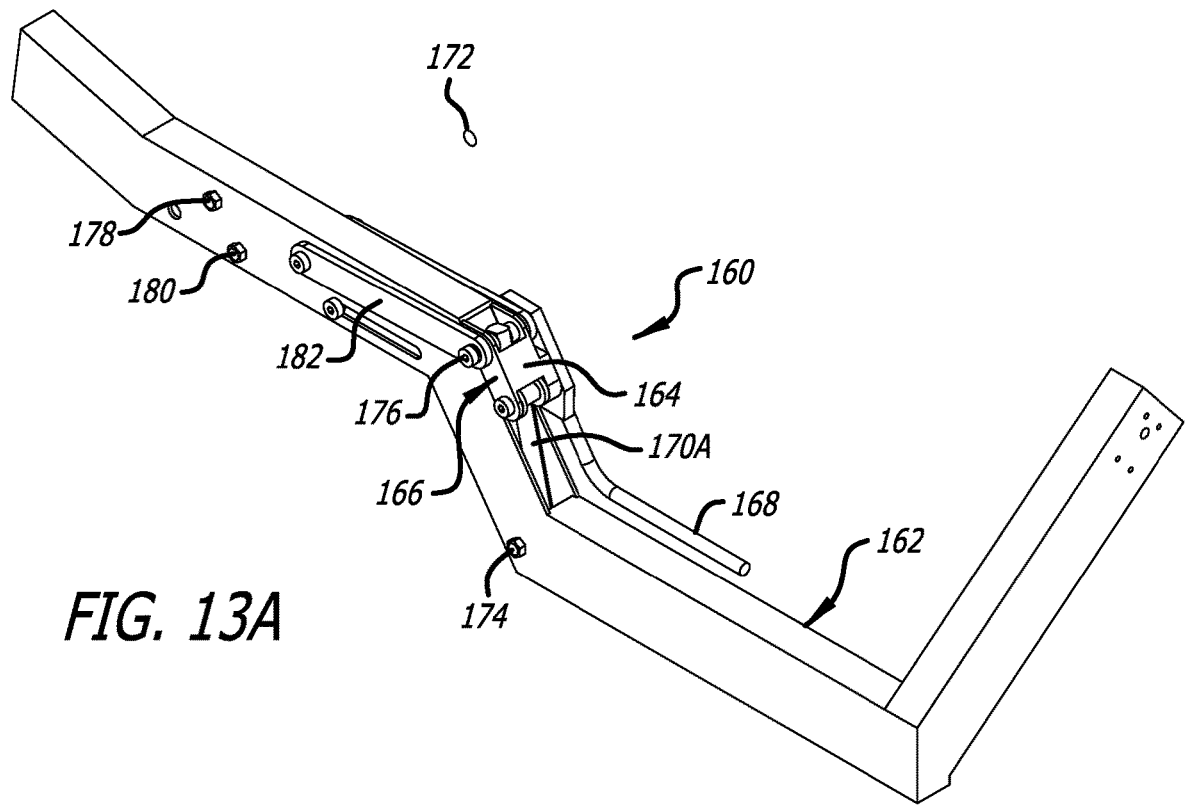
FIG. 13A is a perspective view of an embodiment of a structural offset main beam for use with another embodiment of a torso-lift support showing the torso-lift support in a retracted position.

An alternative preferred embodiment of a torso-lift support is generally indicated by the numeral 160 in FIGS. 13A-15. As depicted in FIGS. 13A-13C, an alternate offset main beam 162 is utilized with the torso-lift support 160. Furthermore, the torso-lift support 160 has a support plate 164 pivotally linked to the offset main beam 162 by a chest support lift mechanism 166. An arm support rod/plate 168 is connected to the support plate 164, and the second arm support 22B. The support plate 164 is attached to the chest support plate 100, and the chest support lift mechanism 166 includes various actuators 170A, 170B, and 170C used to facilitate positioning and repositioning of the support plate 164 (and hence, the chest support plate 100).

Figure 13B:
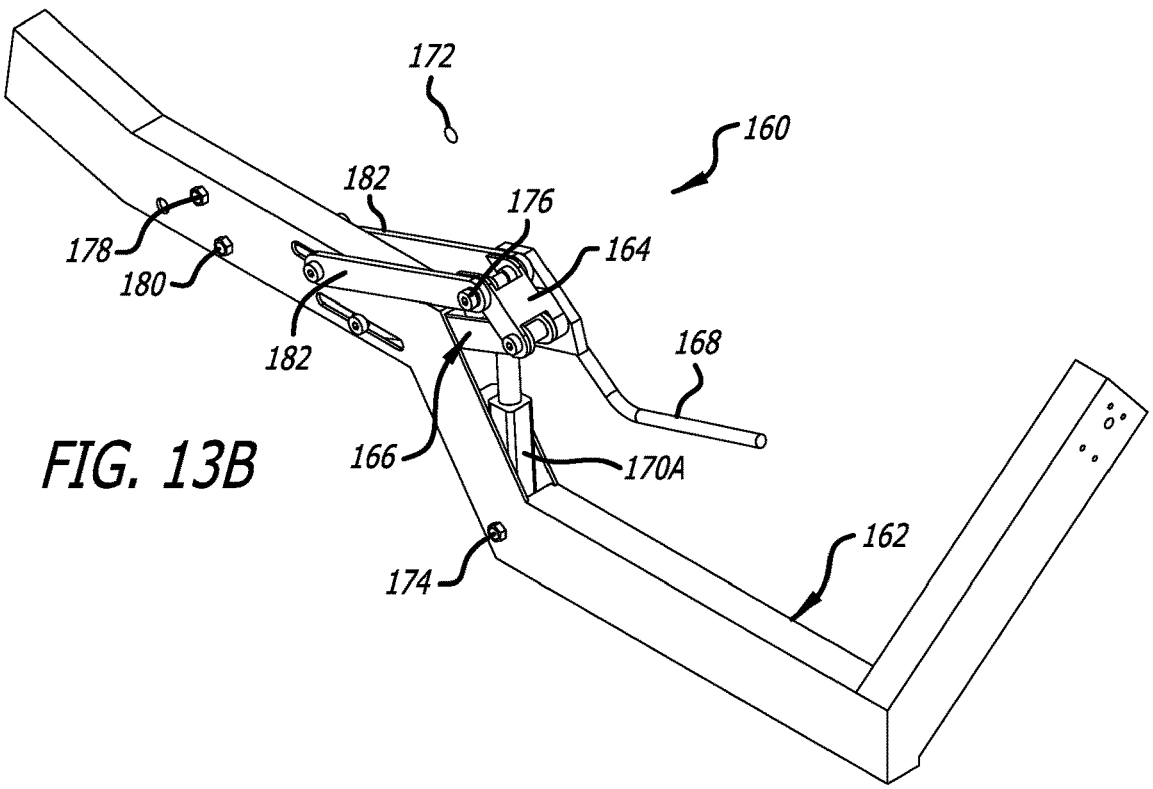
FIG. 13B is a perspective view similar to FIG. 13A showing the torso-lift support at half travel.
Figure 13C:
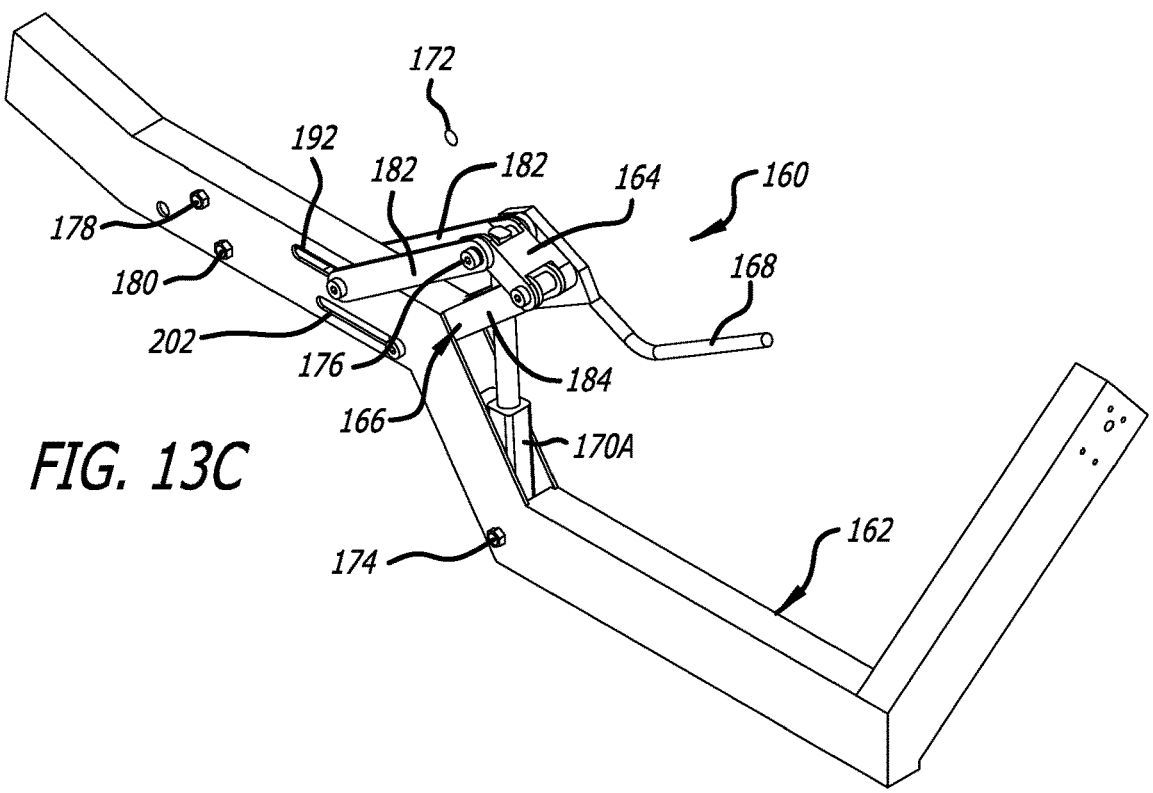
FIG. 13C is a perspective view similar to FIGS. 13A and 13B showing the torso-lift support at full travel.

As discussed below, the torso-lift support 160 depicted in FIGS. 13A-15 enables a COR 172 thereof to be programmably altered such that the COR 172 can be a fixed COR or a variable COR. As their names suggest, the fixed COR stays in the same position as the torso-lift support 160 is actuated, and the variable COR moves between a first position and a second position as the torso-lift support 160 is actuated between its initial position and final position at full travel thereof. Appropriate placement of the COR 172 is important so that spinal cord integrity is not compromised (i.e., overly compressed or stretched). Thus, the support plate 164 (and hence, the chest support plate 100) follows a path coinciding with a predetermined COR 172 (either fixed or variable). FIG. 13A depicts the torso-lift support 160 retracted, FIG. 13B depicts the torso-lift support 160 at half travel, and FIG. 13C depicts the torso-lift support 160 at full travel.

Figure 15:
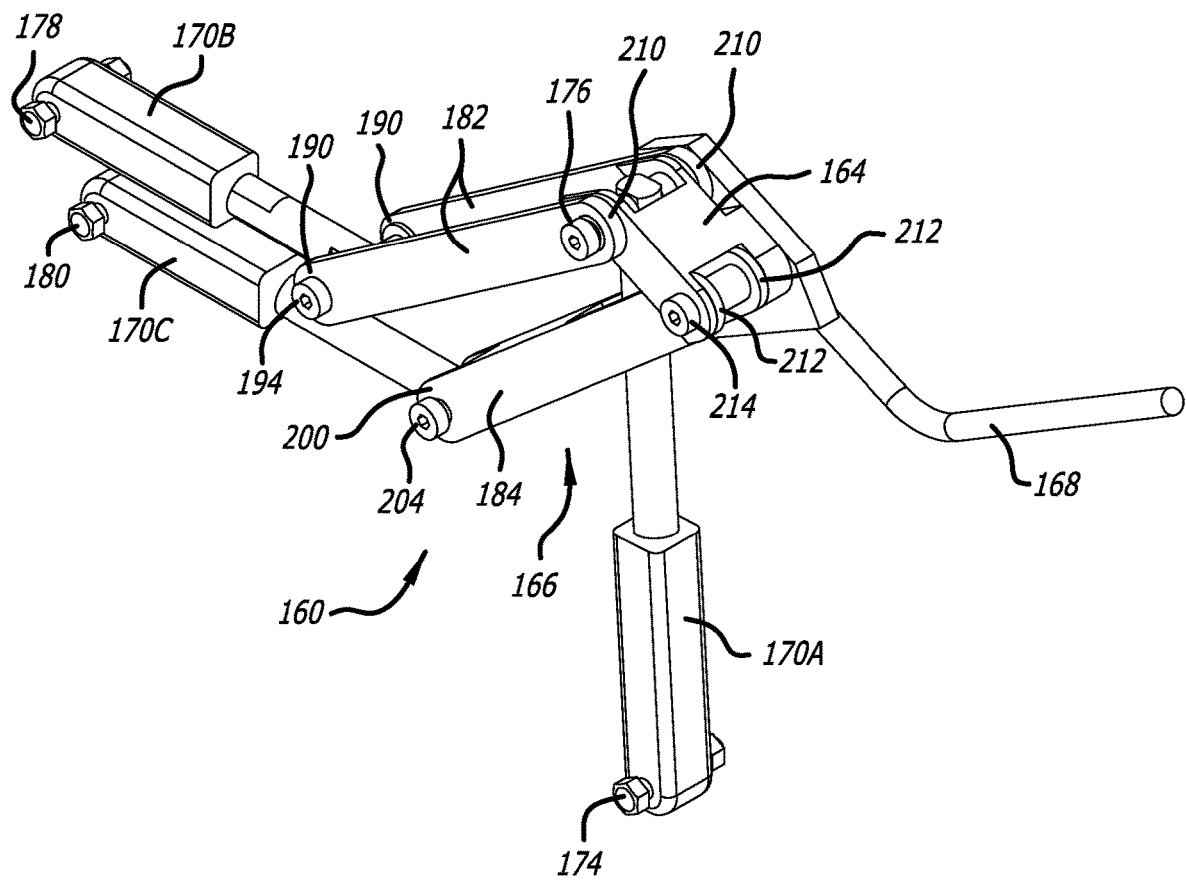
FIG. 15 is another perspective view of a chest support lift mechanism of the torso-lift support of FIGS. 13A-13C with the actuators thereof extended.

As discussed above, the chest support lift mechanism 166 includes the actuators 170A, 170B, and 170C to position and reposition the support plate 164 (and hence, the chest support plate 100). As depicted in FIGS. 14 and 15, for example, the first actuator 170A, the second actuator 170B, and the third actuator 170C are provided. Each of the actuators 170A, 170B, and 170C are interconnected with the offset main beam 12 and the support plate 164, and each of the actuators 170A, 170B, and 170C are moveable between a retracted and extended position. As depicted in FIGS. 13A-13C, the first actuator 170A is pinned to the offset main beam 162 using a pin 174 and pinned to the support plate 164 using a pin 176. Furthermore, the second and third actuators 170B and 170C are received within the offset main beam 162. The second actuator 170B is interconnected with the offset main beam 162 using a pin 178, and the third actuator 170C is interconnected with the offset main beam 162 using a pin 180.

The second actuator 170B is interconnected with the support plate 164 via first links 182, and the third actuator 170C is interconnected with the support plate 164 via second links 184. First ends 190 of the first links 182 are pinned to the second actuator 170B and elongated slots 192 formed in the offset main beam 162 using a pin 194, and first ends 200 of the second links 184 are pinned to the third actuator 170C and elongated slots 202 formed in the offset main beam 162 using a pin 204. The pins 194 and 204 are moveable within the elongated slots 192 and 202. Furthermore, second ends 210 of the first links 182 are pinned to the support plate 164 using the pin 176, and second ends 212 of the second links 184 are pinned to the support plate 164 using a pin 214. To limit interference therebetween, as depicted in FIGS. 13A-13C, the first links 182 are provided on the exterior of the offset main beam 162, and, depending on the position thereof, the second links 184 are positioned on the interior of the offset main beam 162.

Actuation of the actuators 170A, 170B, and 170C facilitates movement of the support plate 164. Furthermore, the amount of actuation of the actuators 170A, 170B, and 170C can be varied to affect different positions of the support plate 164. As such, by varying the amount of actuation of the actuators 170A, 170B, and 170C, the COR 172 thereof can be controlled. As discussed above, the COR 172 can be predetermined, and can be either fixed or varied. Furthermore, the actuation of the actuators 170A, 170B, and 170C can be computer controlled and/or operated by the operator of the surgical frame 10, such that the COR 172 can be programmed by the operator. As such, an algorithm can be used to determine the rates of extension of the actuators 170A, 170B, and 170C to control the COR 172, and the computer controls can handle implementation of the algorithm to provide the predetermined COR. A safety feature can be provided, enabling the operator to read and limit a lifting force applied by the actuators 170A, 170B, and 170C in order to prevent injury to the patient P. Moreover, the torso-lift support 160 can also include safety stops (not shown) to prevent over-extension or compression of the patient P, and sensors (not shown) programmed to send patient position feedback to the safety stops.

FIGS. 16-23 depict portions of the sagittal adjustment assembly 28. The sagittal adjustment assembly 28 can be used to distract or compress the patient's lumbar spine during or after lifting or lowering of the patient's torso by the torso-lift supports. The sagittal adjustment assembly 28 supports and manipulates the lower portion of the patient's body. In doing so, the sagittal adjustment assembly 28 is configured to make adjustments in the sagittal plane of the patient's body, including tilting the pelvis, controlling the position of the upper and lower legs, and lordosing the lumbar spine.

Figure 16:
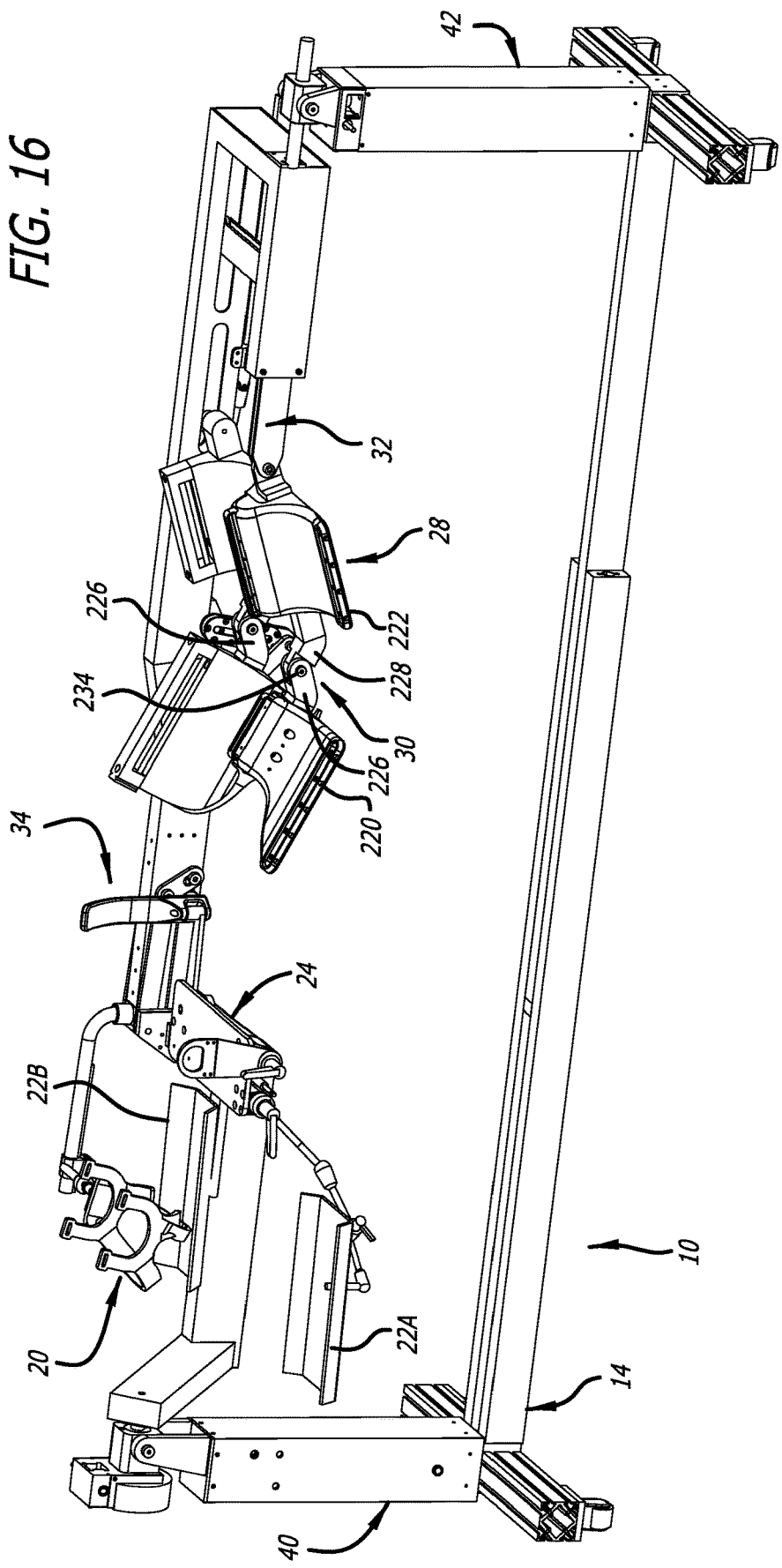
FIG. 16 is a top perspective view of the surgical frame of FIG. 5.
Figure 17:
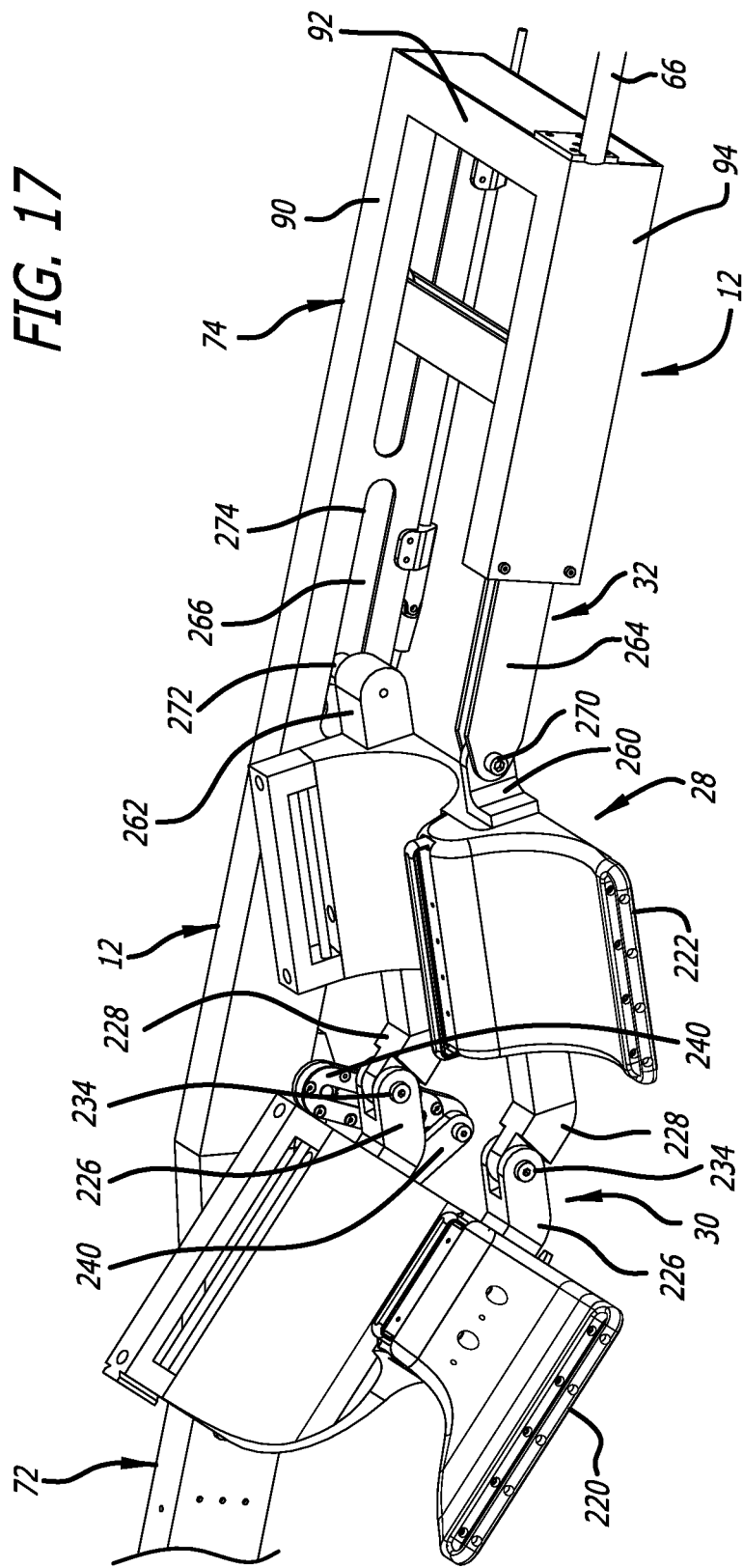
FIG. 17 is an enlarged top perspective view of portions of the surgical frame of FIG. 1 showing a sagittal adjustment assembly including a pelvic-tilt mechanism and leg adjustment mechanism.

As depicted in FIGS. 16 and 17, for example, the sagittal adjustment assembly 28 includes the pelvic-tilt mechanism 30 for supporting the thighs and lower legs of the patient P. The pelvic-tilt mechanism 30 includes a thigh cradle 220 configured to support the patient's thighs, and a lower leg cradle 222 configured to support the patient's shins. Different sizes of thigh and lower leg cradles can be used to accommodate different sizes of patients, i.e., smaller thigh and lower leg cradles can be used with smaller patients, and larger thigh and lower leg cradles can be used with larger patients. Soft straps (not shown) can be used to secure the patient P to the thigh cradle 220 and the lower leg cradle 222. The thigh cradle 220 and the lower leg cradle 222 are moveable and pivotal with respect to one another and to the offset main beam 12. To facilitate rotation of the patient's hips, the thigh cradle 220 and the lower leg cradle 222 can be positioned anterior and inferior to the patient's hips.

Figure 18:
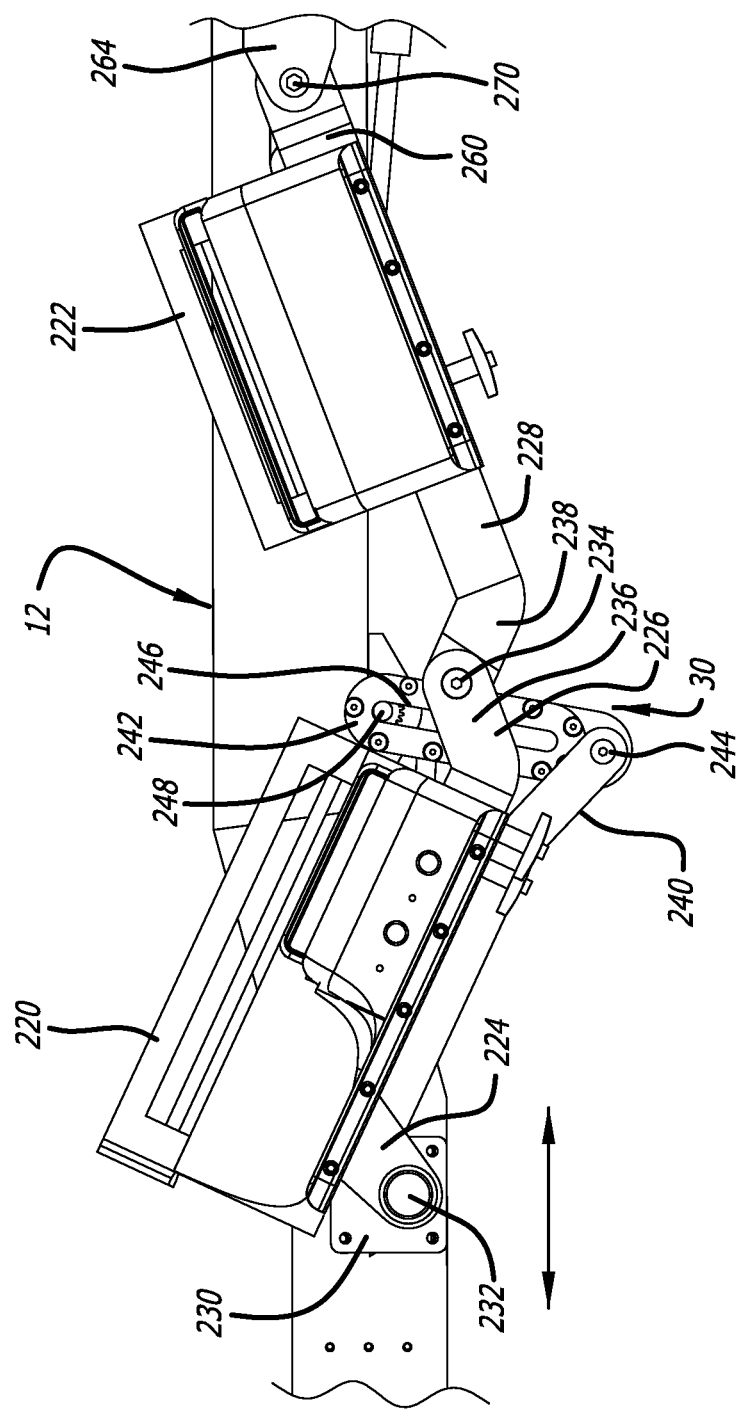
FIG. 18 is an enlarged side elevational view of portions of the surgical frame of FIG. 1 showing the pelvic-tilt mechanism.
Figure 25:
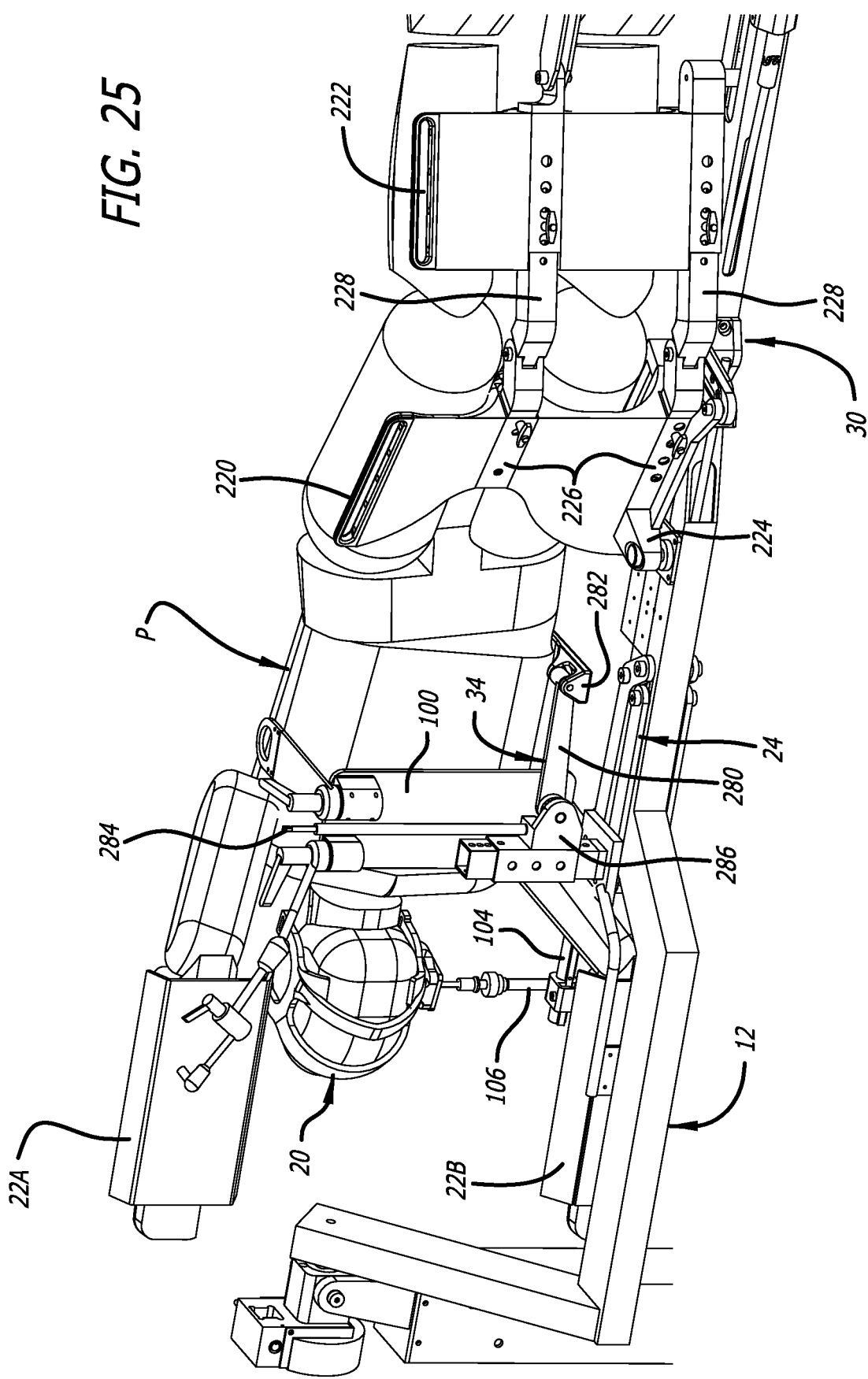
FIG. 25 is a top perspective view of portions of the surgical frame of FIG. 1 showing operation of the coronal adjustment assembly.

As depicted in FIGS. 18 and 25, for example, a first support strut 224 and second support struts 226 are attached to the thigh cradle 220. Furthermore, third support struts 228 are attached to the lower leg cradle 222. The first support strut 224 is pivotally attached to the offset main beam 12 via a support plate 230 and a pin 232, and the second support struts 226 are pivotally attached to the third support struts 228 via pins 234. The pins 234 extend through angled end portions 236 and 238 of the second and third support struts 226 and 228, respectively. Furthermore, the lengths of second and third support struts 226 and 228 are adjustable to facilitate expansion and contraction of the lengths thereof.

To accommodate patients with different torso lengths, the position of the thigh cradle 220 can be adjustable by moving the support plate 230 along the offset main beam 12. Furthermore, to accommodate patients with different thigh and lower leg lengths, the lengths of the second and third support struts 226 and 228 can be adjusted.

Figure 19:
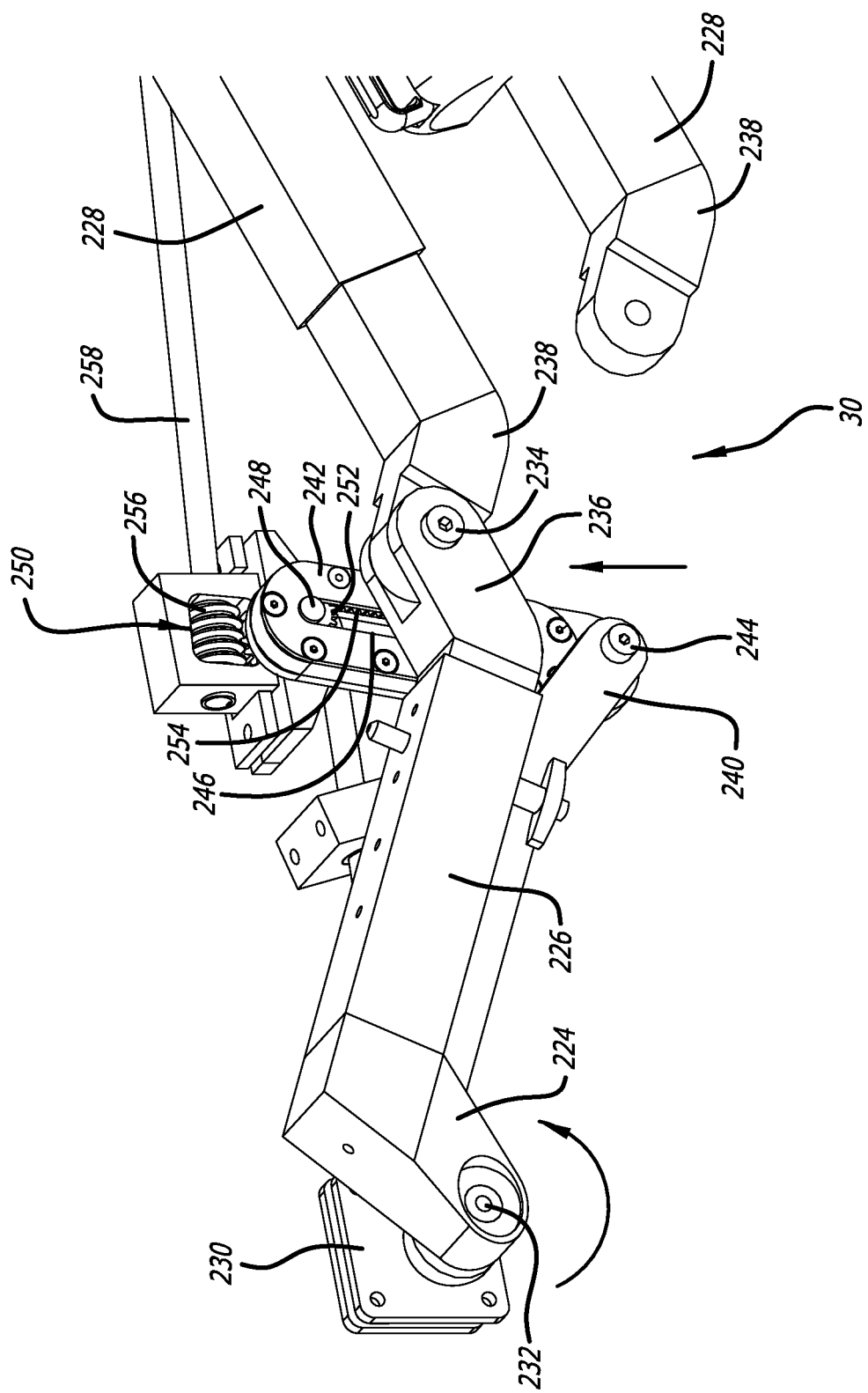
FIG. 19 is an enlarged perspective view of componentry of the pelvic-tilt mechanism.
Figure 20:
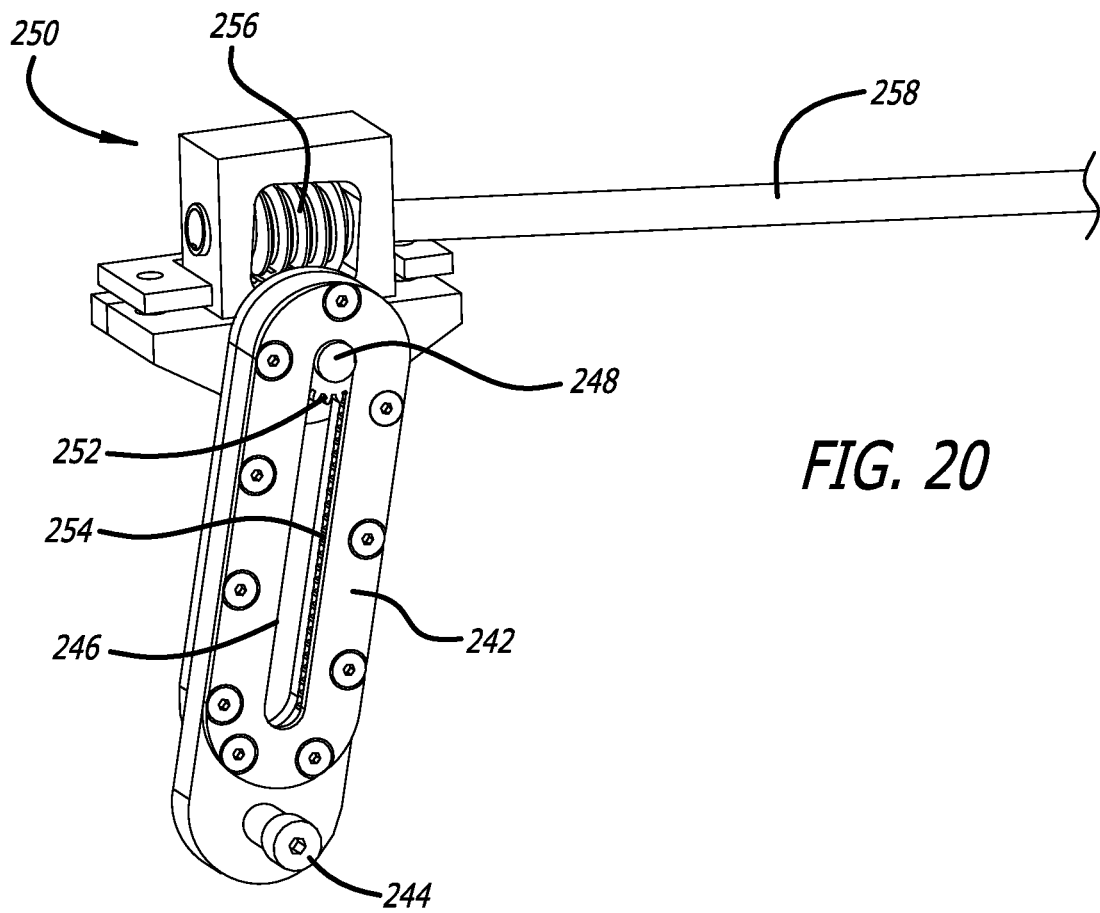
FIG. 20 is an enlarged perspective view of a captured rack and a worm gear assembly of the componentry of the pelvic-tilt mechanism.
Figure 21:
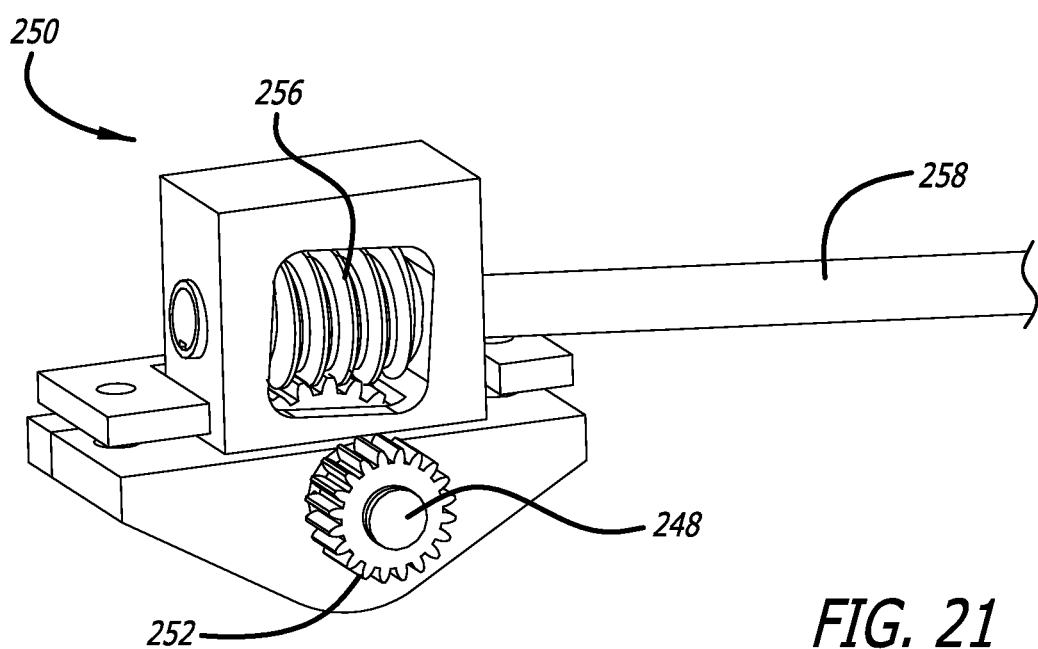
FIG. 21 is an enlarged perspective view of the worm gear assembly of FIG. 20.

To control the pivotal angle between the second and third support struts 226 and 228 (and hence, the pivotal angle between the thigh cradle 220 and lower leg cradle 222), a link 240 is pivotally connected to a captured rack 242 via a pin 244. The captured rack 242 includes an elongated slot 246, through which is inserted a worm gear shaft 248 of a worm gear assembly 250. The worm gear shaft 248 is attached to a gear 252 provided on the interior of the captured rack 242. The gear 252 contacts teeth 254 provided inside the captured rack 242, and rotation of the gear 252 (via contact with the teeth 254) causes motion of the captured rack 242 upwardly and downwardly. The worm gear assembly 250, as depicted in FIGS. 19-21, for example, includes worm gears 256 which engage a drive shaft 258, and which are connected to the worm gear shaft 248.

The worm gear assembly 250 also is configured to function as a brake, which prevents unintentional movement of the sagittal adjustment assembly 28. Rotation of the drive shaft 258 causes rotation of the worm gears 256, thereby causing reciprocal vertical motion of the captured rack 242. The vertical reciprocal motion of the captured rack 242 causes corresponding motion of the link 240, which in turn pivots the second and third support struts 226 and 228 to correspondingly pivot the thigh cradle 220 and lower leg cradle 222. A servomotor (not shown) interconnected with the drive shaft 258 can be computer controlled and/or operated by the operator of the surgical frame 10 to facilitate controlled reciprocal motion of the captured rack 242.

The sagittal adjustment assembly 28 also includes the leg adjustment mechanism 32 facilitating articulation of the thigh cradle 220 and the lower leg cradle 222 with respect to one another. In doing so, the leg adjustment mechanism 32 accommodates the lengthening and shortening of the patient's legs during bending thereof. As depicted in FIG. 17, for example, the leg adjustment mechanism 32 includes a first bracket 260 and a second bracket 262 attached to the lower leg cradle 222. The first bracket 260 is attached to a first carriage portion 264, and the second bracket 262 is attached to a second carriage portion 266 via pins 270 and 272, respectively. The first carriage portion 264 is slidable within third portion 94 of the rear portion 74 of the offset main beam 12, and the second carriage portion 266 is slidable within the first portion 90 of the rear portion 74 of the offset main beam 12. An elongated slot 274 is provided in the first portion 90 to facilitate engagement of the second bracket 262 and the second carriage portion 266 via the pin 272. As the thigh cradle 220 and the lower leg cradle 222 articulate with respect to one another (and the patient's legs bend accordingly), the first carriage 264 and the second carriage 266 can move accordingly to accommodate such movement.

Figure 22:
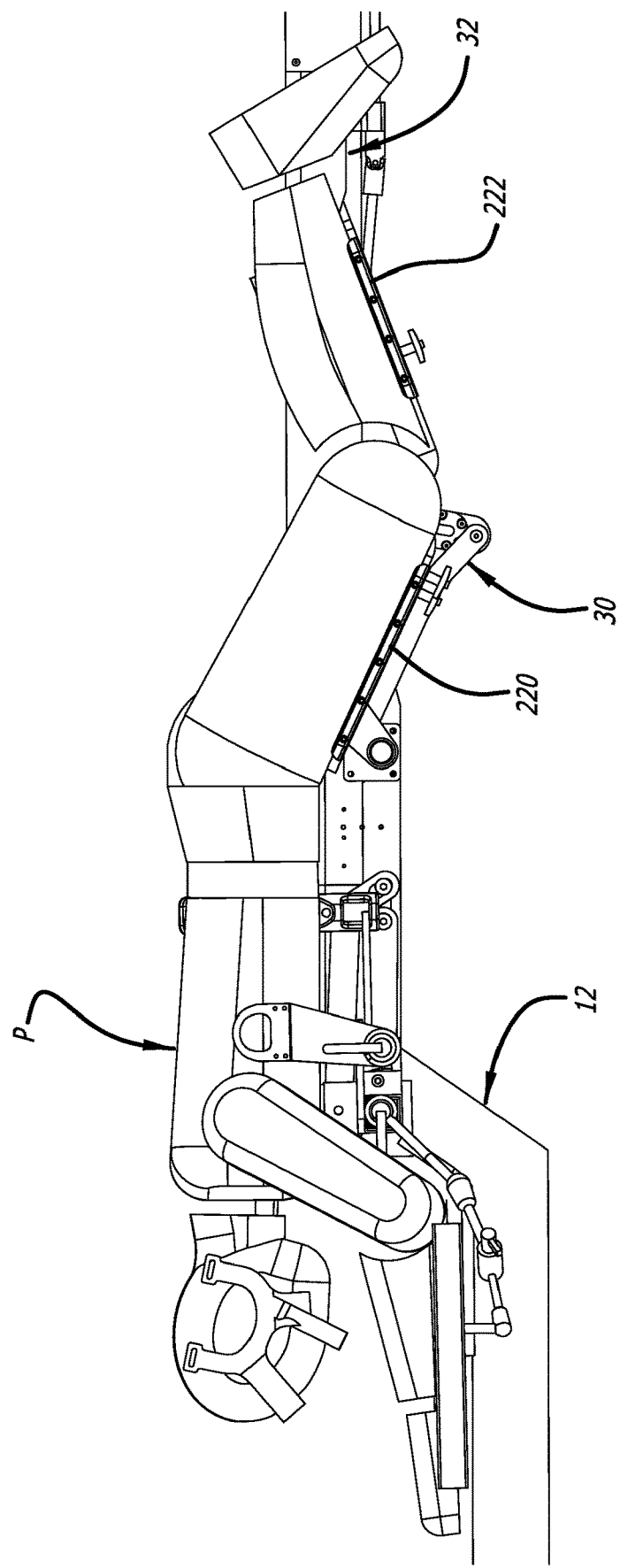
FIG. 22 is a side elevational view of portions of the surgical frame of FIG. 1 showing the patient positioned thereon and the pelvic-tilt mechanism of the sagittal adjustment assembly in the flexed position.

The pelvic-tilt mechanism 30 is movable between a flexed position and a fully extended position. As depicted in FIG. 22, in the flexed position, the lumbar spine is hypo-lordosed.

Figure 23:
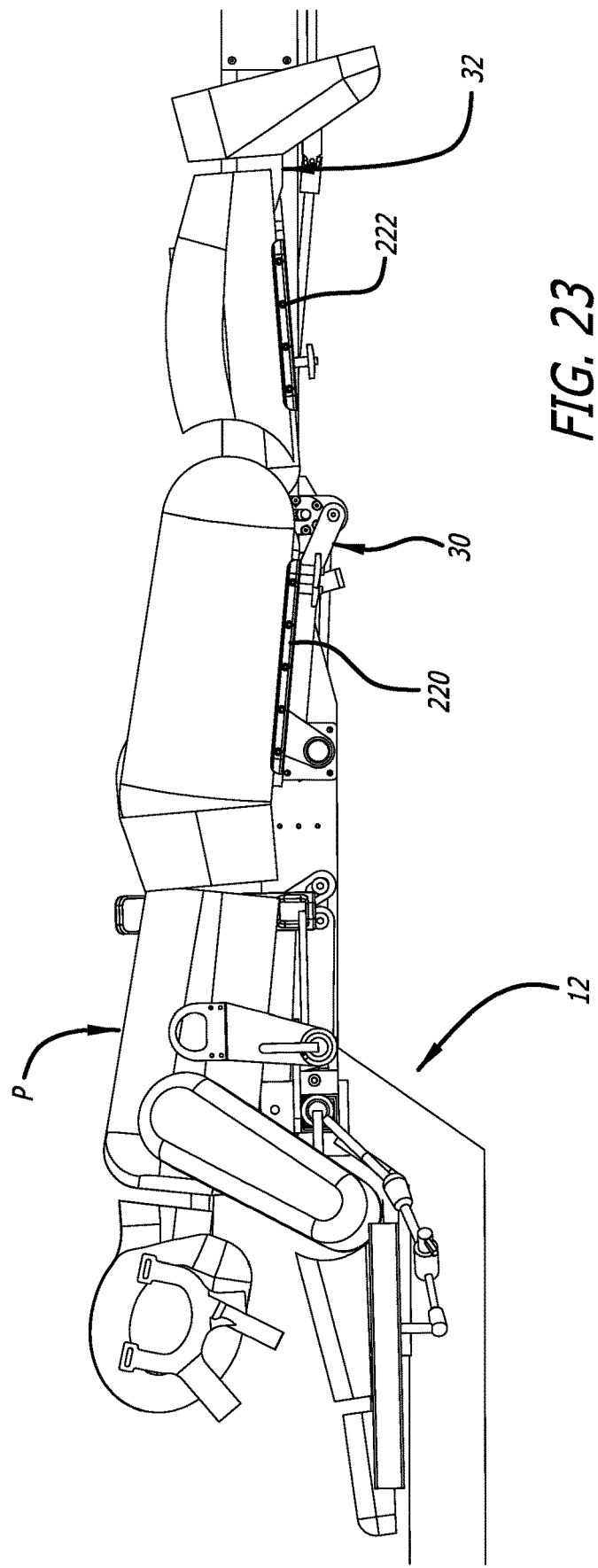
FIG. 23 is another side elevational view of portions of the surgical frame of FIG. 1 showing the patient positioned thereon and the pelvic-tilt mechanism of the sagittal adjustment assembly in the fully extended position.

This opens the posterior boundaries of the lumbar vertebral bodies and allows for easier placement of any interbody devices. The lumbar spine stretches slightly in this position. As depicted in FIG. 23, in the extended position, the lumbar spine is lordosed. This compresses the lumbar spine. When posterior fixation devices, such as rods and screws, are placed, optimal sagittal alignment can be achieved. During sagittal alignment, little to negligible angle change occurs between the thighs and the pelvis. The pelvic-tilt mechanism 30 also can hyper-extend the hips as a means of lordosing the spine, in addition to tilting the pelvis. One of ordinary skill will recognize, however, that straightening the patient's legs does not lordose the spine. Leg straightening is a consequence of rotating the pelvis while maintaining a fixed angle between the pelvis and the thighs.

The sagittal adjustment assembly 28, having the configuration described above, further includes an ability to compress and distract the spine dynamically while in the lordosed or flexed positions. The sagittal adjustment assembly 28 also includes safety stops (not shown) to prevent over-extension or compression of the patient, and sensors (not shown) programmed to send patient position feedback to the safety stops.

Figure 24:
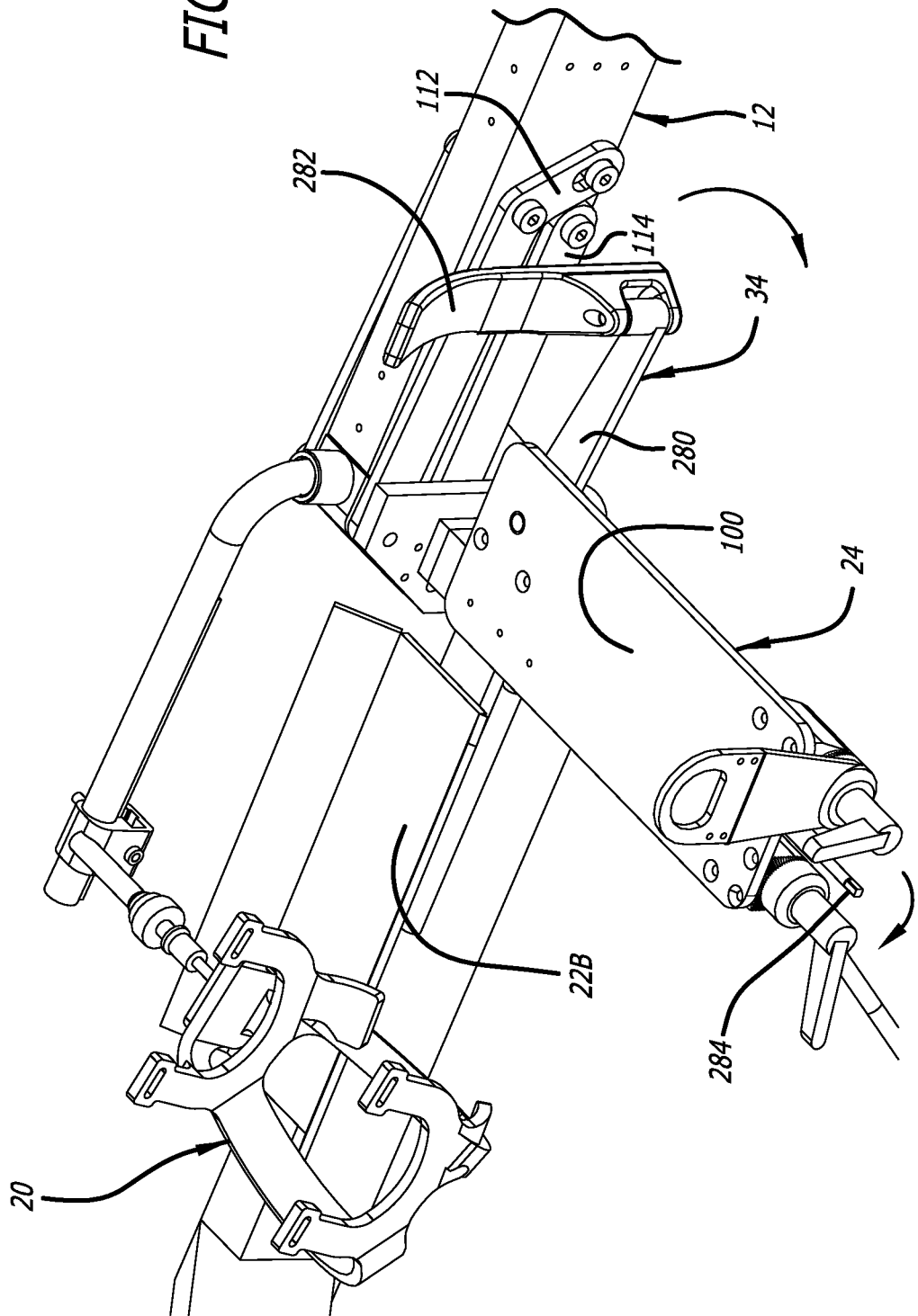
FIG. 24 is an enlarged top perspective view of portions of the surgical frame of FIG. 1 showing a coronal adjustment assembly.
Figure 26:
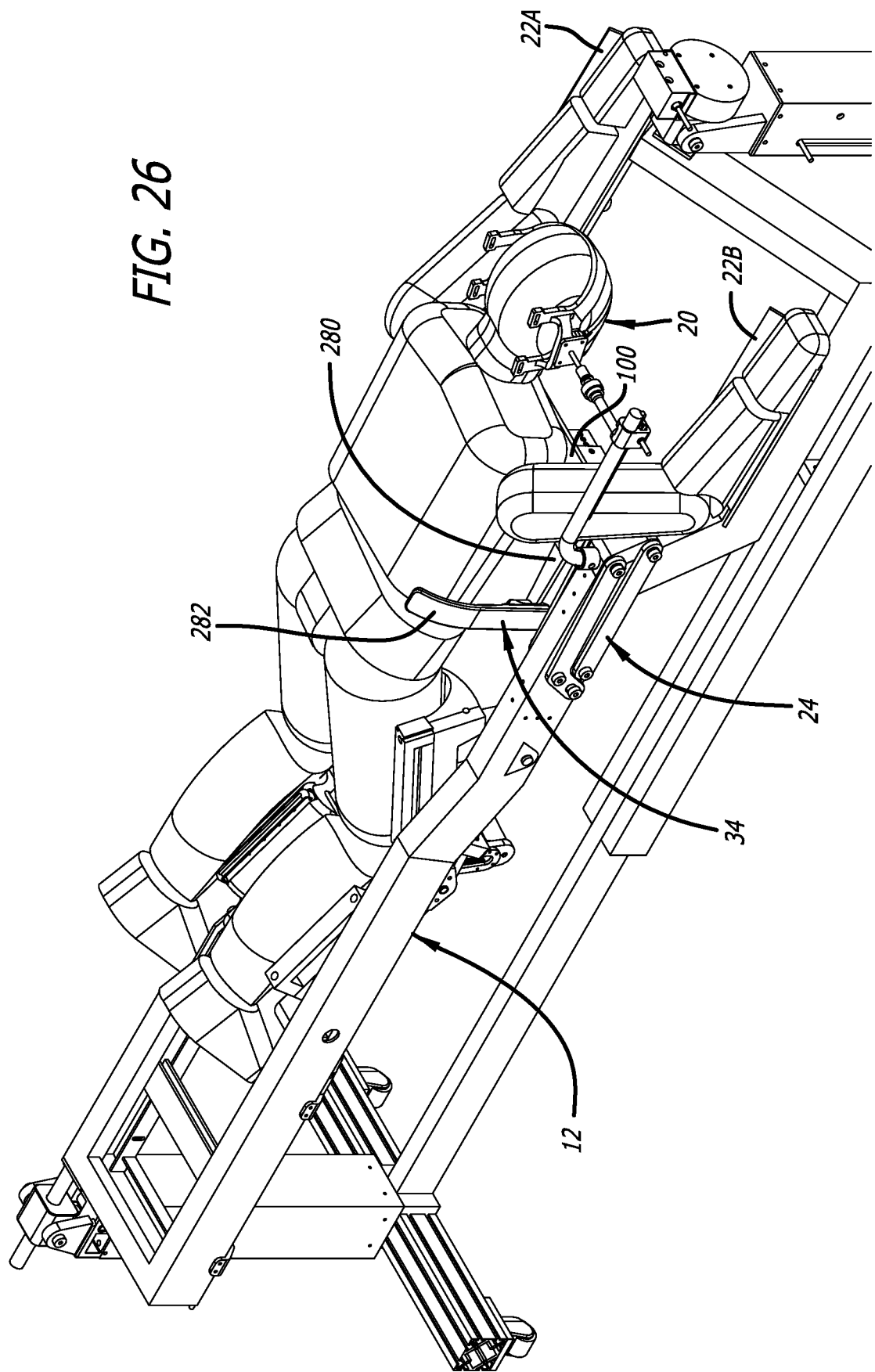
FIG. 26 is a top perspective view of a portion of the surgical frame of FIG. 1 showing operation of the coronal adjustment assembly.
Figure 27:
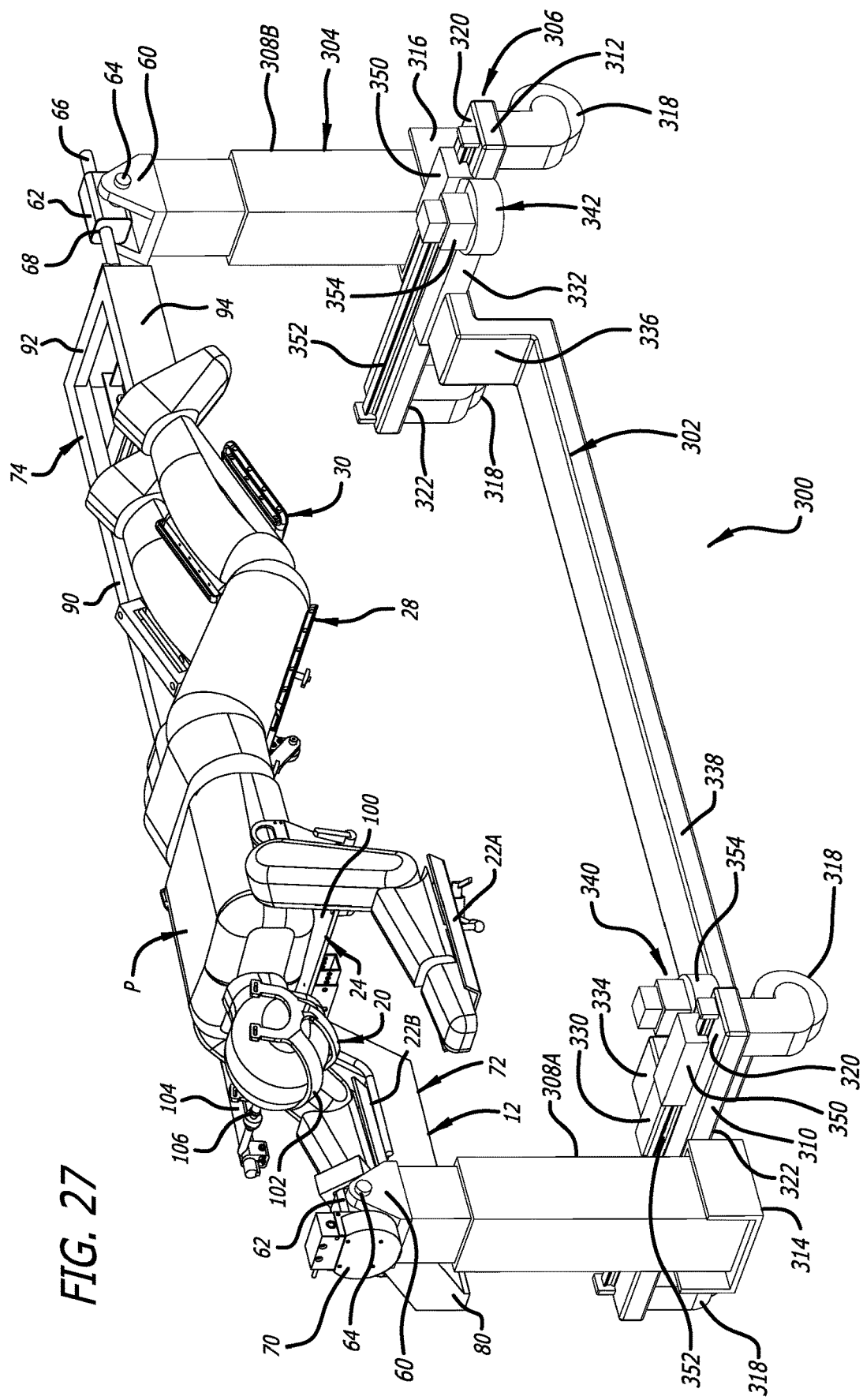
FIG. 27 is a top perspective view of a surgical frame in accordance with an embodiment of the present invention with the patient positioned thereon in a prone position showing a translating beam thereof in a first position.

As depicted in FIGS. 24-26, for example, the coronal adjustment assembly 34 is configured to support and manipulate the patient's torso, and further to correct a spinal deformity, including but not limited to a scoliotic spine. As depicted in FIGS. 24-26, for example, the coronal adjustment assembly 34 includes a lever 280 linked to an arcuate radio-lucent paddle 282. As depicted in FIGS. 24 and 25, for example, a rotatable shaft 284 is linked to the lever 280 via a transmission 286, and the rotatable shaft 284 projects from an end of the chest support plate 100. Rotation of the rotatable shaft 284 is translated by the transmission 286 into rotation of the lever 280, causing the paddle 282, which is linked to the lever 280, to swing in an arc. Furthermore, a servomotor (not shown) interconnected with the rotatable shaft 284 can be computer controlled and/or operated by the operator of the surgical frame 10 to facilitate controlled rotation of the lever 280.

As depicted in FIG. 24, for example, adjustments can be made to the position of the paddle 282 to manipulate the torso and straighten the spine. As depicted in FIG. 25, when the offset main beam 12 is positioned such that the patient P is positioned in a lateral position, the coronal adjustment assembly 34 supports the patient's torso. As further depicted in FIG. 26, when the offset main beam 12 is positioned such that the patient P is positioned in a prone position, the coronal adjustment assembly 34 can move the torso laterally, to correct a deformity, including but not limited to a scoliotic spine. When the patient is strapped in via straps (not shown) at the chest and legs, the torso is relatively free to move and can be manipulated. Initially, the paddle 282 is moved by the lever 280 away from the offset main beam 12. After the paddle 282 has been moved away from the offset main beam 12, the torso can be pulled with a strap towards the offset main beam 12. The coronal adjustment assembly 34 also includes safety stops (not shown) to prevent over-extension or compression of the patient, and sensors (not shown) programmed to send patient position feedback to the safety stops.

A preferred embodiment of a surgical frame incorporating a translating beam is generally indicated by the numeral 300 in FIGS. 27-30. Like the surgical frame 10, the surgical frame 300 serves as an exoskeleton to support the body of the patient P as the patient's body is manipulated thereby. In doing so, the surgical frame 300 serves to support the patient P such that the patient's spine does not experience unnecessary stress/torsion.

The surgical frame 300 includes translating beam 302 that is generally indicated by the numeral 302 in FIGS. 27-30. The translating beam 302 is capable of translating motion affording it to be positioned and repositioned with respect to portions of the remainder of the surgical frame 300. As discussed below, the positioning and repositioning of the translating beam 302, for example, affords greater access to a patient receiving area A defined by the surgical frame 300, and affords greater access to the patient P by a surgeon and/or a surgical assistant (generally indicated by the letter S in FIG. 30) via access to either of the lateral sides $L_1$ and $L_2$ (FIG. 30) of the surgical frame 300.

As discussed below, by affording greater access to the patient receiving area A, the surgical frame 300 affords transfer of the patient P from and to a surgical table/gurney. Using the surgical frame 300, the surgical table/gurney can be conventional, and there is no need to lift the surgical table/gurney over portions of the surgical frame 300 to afford transfer of the patient P thereto.

The surgical frame 300 is configured to provide a relatively minimal amount of structure adjacent the patient's spine to facilitate access thereto and to improve the quality of imaging available before, during, and even after surgery. Thus, the workspace of a surgeon and/or a surgical assistant and imaging access are thereby increased. The workspace, as discussed below, can be further increased by positioning and repositioning the translating beam 302. Furthermore, radio-lucent or low magnetic susceptibility materials can be used in constructing the structural components adjacent the patient's spine in order to further enhance imaging quality.

The surgical frame 300, as depicted in FIGS. 27-30, is similar to the surgical frame 10 except that surgical frame 300 includes a support structure 304 having a support platform 306 incorporating the translating beam 302. The surgical frame 300 incorporates the offset main beam 12 and the features associated therewith from the surgical table 300. As such, the element numbering used to describe the surgical frame 10 is also applicable to portions of the surgical frame 300.

Rather than including the cross member 44, and the horizontal portions 46 and the vertical portions 48 of the first and second support portions 40 and 42, the support structure 304 includes the support platform 306, a first vertical support post 308A, and a second vertical support post 308B. As depicted in FIGS. 27-30, the support platform 306 extends from adjacent one longitudinal end to adjacent the other longitudinal end of the surgical frame 300, and the support platform 306 supports the first vertical support post 308A at the one longitudinal end and supports the second vertical support post 308B at the other longitudinal end.

As depicted in FIGS. 27-30, the support platform 306 (in addition to the translating beam 302) includes a first end member 310, a second end member 312, a first support bracket 314, and a second support bracket 316. Casters 318 are attached to the first and second end members 310 and 312. The first end member 310 and the second end member 312 each include an upper surface 320 and a lower surface 322. The casters 318 can be attached to the lower surface of each of the first and second end members 310 and 312 at each end thereof, and the casters 318 can be spaced apart from one another to afford stable movement of the surgical frame 300. Furthermore, the first support bracket 314 supports the first vertical support post 308A, and the second support bracket 316 supports the vertical second support post 308B.

The translating beam 302 is interconnected with the first and second end members 310 and 312 of the support platform 306, and as depicted in FIGS. 27-30, the translating beam 302 is capable of movement with respect to the first and second end members 310 and 312. The translating beam 302 includes a first end member 330, a second end member 332, a first L-shaped member 334, a second L-shaped member 336, and a cross member 338. The first L-shaped member 334 is attached to the first end member 330 and the cross member 338, and the second L-shaped member 336 is attached to the second end member 332 and the cross member 338. Portions of the first and second L-shaped members 334 and 336 extend downwardly relative to the first and second end members 330 and 332 such that the cross member 338 is positioned vertically below the first and second end member 330 and 332. The vertical position of the cross member 338 relative to the remainder of the surgical frame 300 lowers the center of gravity of the surgical frame 300, and in doing so, serves in adding to the stability of the surgical frame 300.

The translating beam 302, as discussed above, is capable of being positioned and repositioned with respect to portions of the remainder of the surgical frame 300. To that end, the support platform 306 includes a first translation mechanism 340 and a second translation mechanism 342. The first translation mechanism 340 facilitates attachment between the first end members 310 and 330, and the second translation mechanism 342 facilitates attachment between the second end members 312 and 332. The first and second translation mechanism 340 and 342 also facilitate movement of the translating beam 302 relative to the first end member 310 and the second end member 312.

The first and second translation mechanisms 340 and 342 can each include a transmission 350 and a track 352 for facilitating movement of the translating beam 302. The tracks 352 are provided on the upper surface 320 of the first and second end members 310 and 312, and the transmissions 350 are interoperable with the tracks 352. The first and second transmission mechanisms 340 and 342 can each include an electrical motor 354 or a hand crank (not shown) for driving the transmissions 350. Furthermore, the transmissions 350 can include, for example, gears or wheels driven thereby for contacting the tracks 352. The interoperability of the transmissions 350, the tracks 352, and the motors 354 or hand cranks form a drive train for moving the translating beam 302. The movement afforded by the first and second translation mechanism 340 and 342 allows the translating beam 302 to be positioned and repositioned relative to the remainder of the surgical frame 300.

The surgical frame 300 can be configured such that operation of the first and second translation mechanism 340 and 342 can be controlled by an operator such as a surgeon and/or a surgical assistant. As such, movement of the translating beam 302 can be effectuated by controlled automation. Furthermore, the surgical frame 300 can be configured such that movement of the translating beam 302 automatically coincides with the rotation of the offset main beam 12. By tying the position of the translating beam 302 to the rotational position of the offset main beam 12, the center of gravity of the surgical frame 300 can be maintained in positions advantageous to the stability thereof.

During use of the surgical frame 300, access to the patient receiving area A and the patient P can be increased or decreased by moving the translating beam 302 between the lateral sides $L_1$ and $L_2$ of the surgical frame 300. Affording greater access to the patient receiving area A facilitates transfer of the patient P between the surgical table/gurney and the surgical frame 300. Furthermore, affording greater access to the patient P facilitates ease of access by a surgeon and/or a surgical assistant to the surgical site on the patient P.

Figure 28:
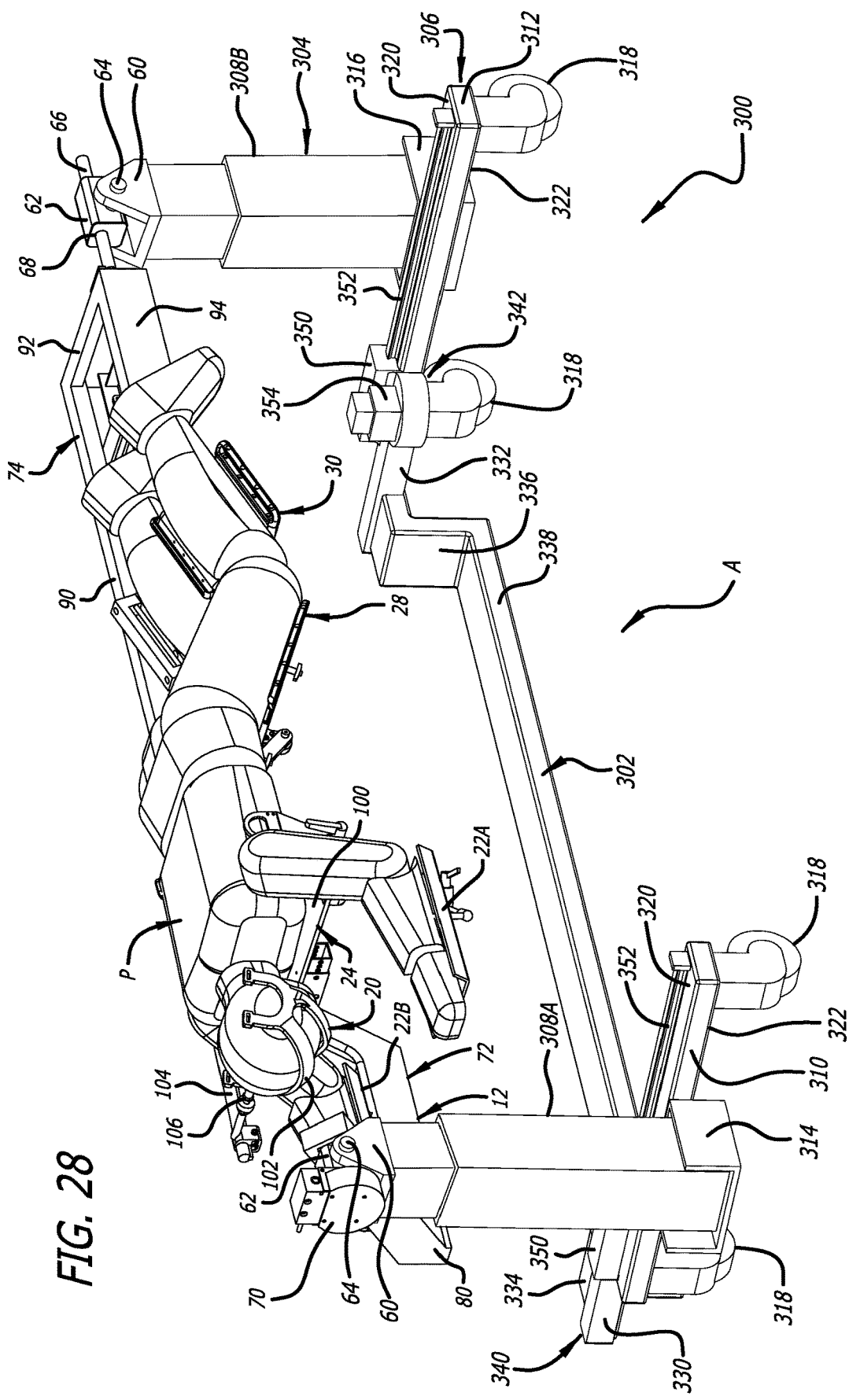
FIG. 28 is another top perspective view of the surgical frame of FIG. 27 with the patient in a prone position showing the translating beam thereof in a second position.
Figure 29:
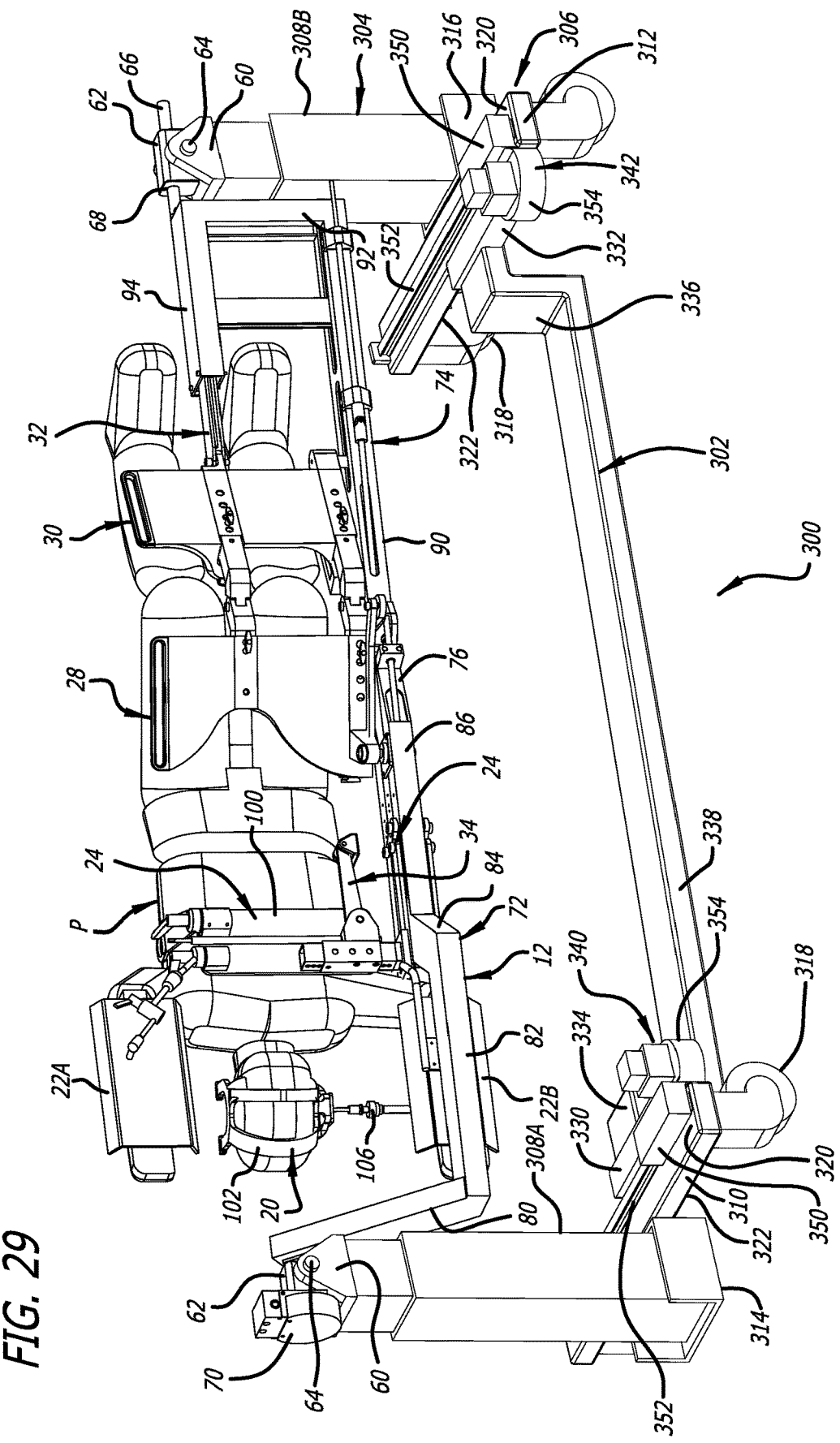
FIG. 29 is yet another top perspective view of the surgical frame of FIG. 27 with the patient in a lateral position showing the translating beam thereof in a third position.
Figure 30:
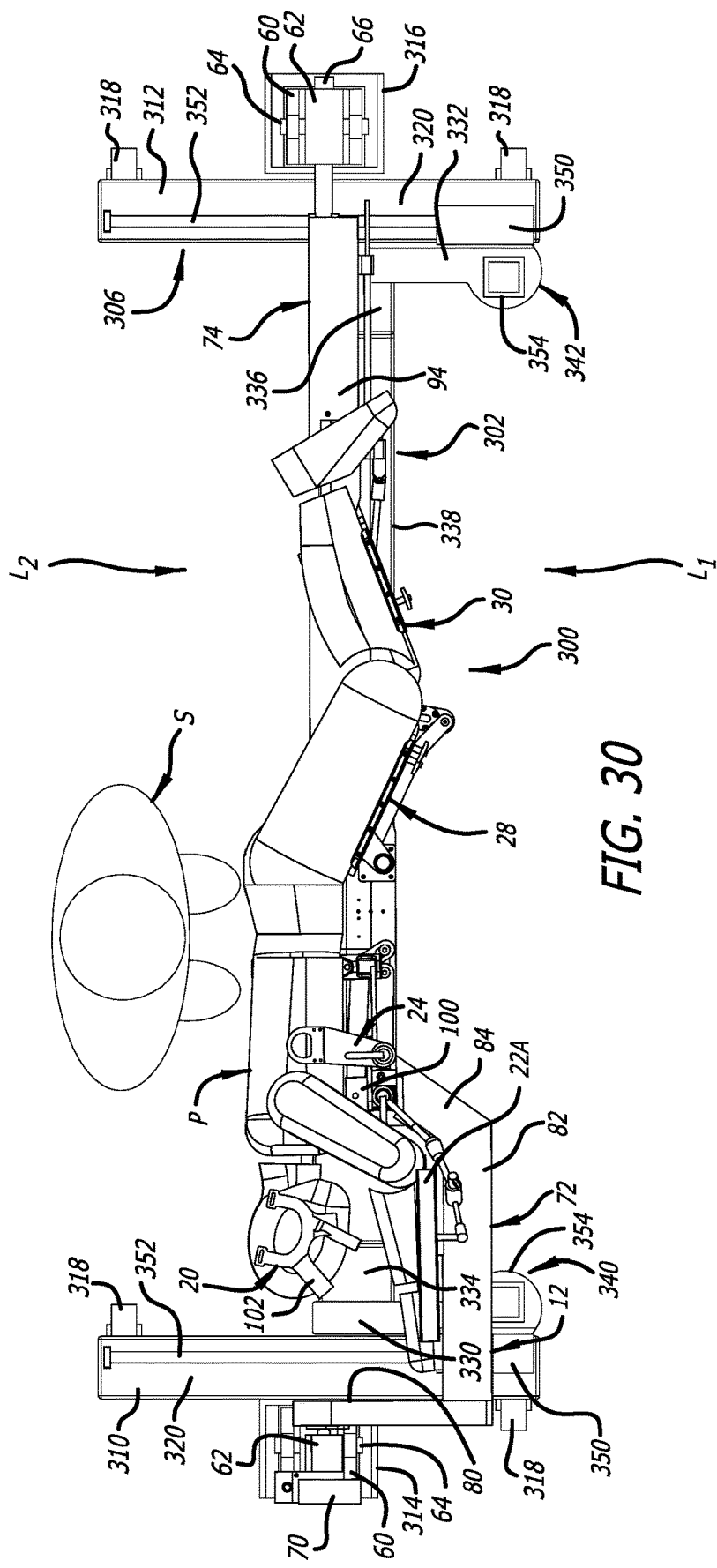
FIG. 30 is top plan view of the surgical frame of FIG. 27 with the patient in a lateral position showing the translating beam thereof in the third position.
Figure 31:
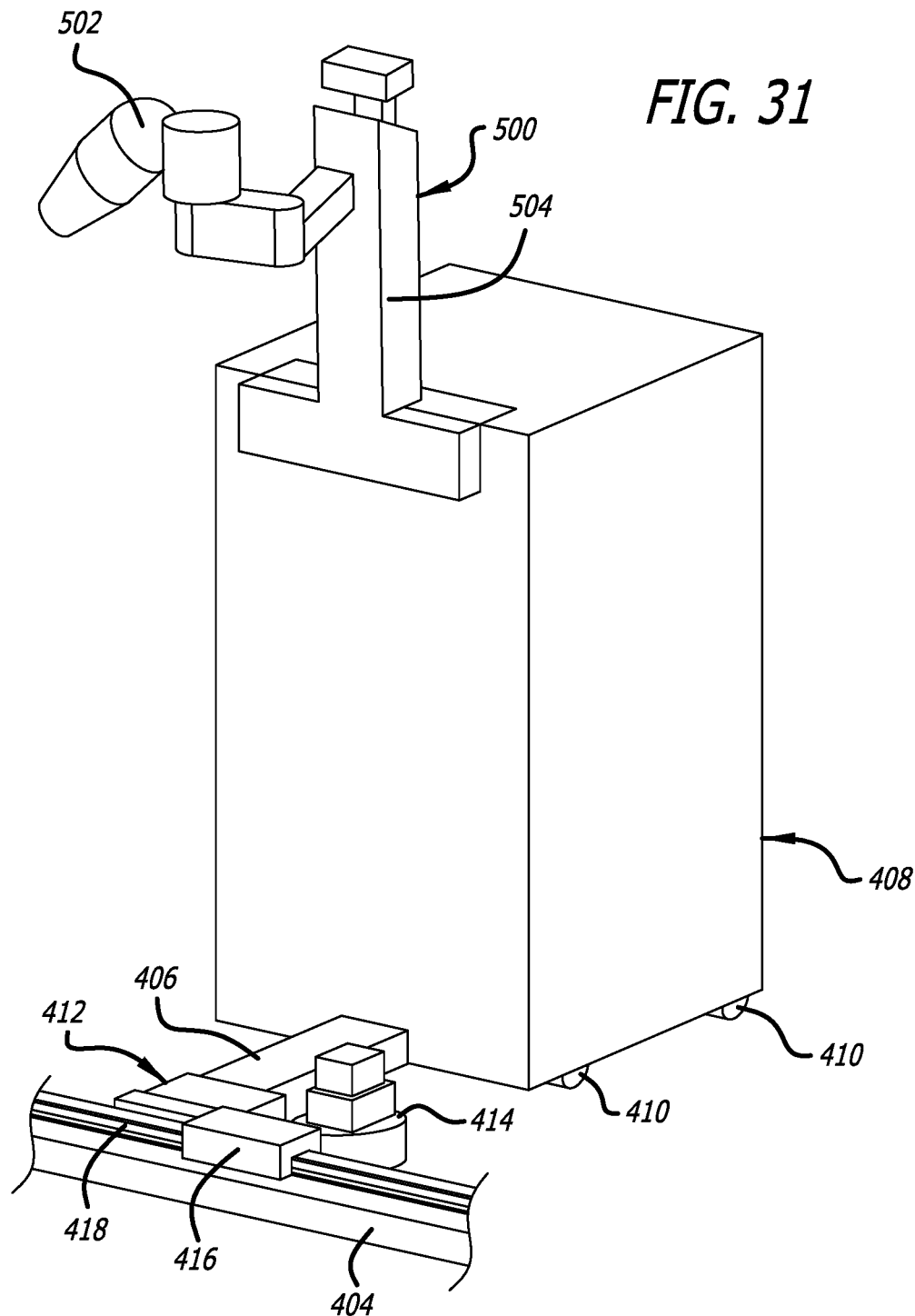
FIG. 31 is a top side perspective view of a surgical cart supporting a surgical robot thereon, a linkage attached to the surgical cart, and a portion of a linear movement mechanism attached to the linkage and to a portion of a translating beam of a surgical frame.

The translating beam 302 is moveable using the first and second translation mechanisms 340 and 342 between a first terminal position (FIG. 28) and a second terminal position (FIGS. 29 and 30). The translating beam 302 is positionable at various positions (FIG. 27) between the first and second terminal positions. When the translating beam 302 is in the first terminal position, as depicted in FIG. 28, the translating beam 302 and its cross member 338 are positioned on the lateral side $L_1$ of the surgical frame 300. Furthermore, when the translating beam 302 is in the second terminal position, as depicted in FIGS. 29 and 30, the translating beam 302 and its cross member 338 are positioned in the middle of the surgical frame 300.

With the translating beam 302 and its cross member 338 moved to be positioned at the lateral side $L_1$, the surgical table/gurney and the patient P positioned thereon can be positioned under the offset main beam 12 in the patient receiving area A to facilitate transfer of the patient P to or from the offset main beam 12. As such, the position of the translating beam 302 at the lateral side $L_1$ enlarges the patient receiving area A so that the surgical table/gurney can be received therein to allow such transfer to or from the offset main beam 12.

Furthermore, with the translating beam 302 and its cross member 338 moved to be in the middle of the surgical frame 300 (FIGS. 29 and 30), a surgeon and/or a surgical assistant can have access to the patient P from either of the lateral sides $L_1$ or $L_2$. As such, the position of the translating beam 302 in the middle of the surgical frame 300 allows a surgeon and/or a surgical assistant to get close to the patient P supported by the surgical frame 300. As depicted in FIG. 30, for example, a surgeon and/or a surgical assistant can get close to the patient P from the lateral side $L_2$ without interference from the translating beam 302 and its cross member 338. The position of the translating beam 302 can be selected to accommodate access by both a surgeon and/or a surgical assistant by avoiding contact thereof with the feet and legs of a surgeon and/or a surgical assistant.

The position of the translating beam 302 and its cross member 338 can also be changed according to the rotational position of the offset main beam 12. To illustrate, the offset main beam 12 can be rotated a full 360° before, during, and even after surgery to facilitate various positions of the patient to afford various surgical pathways to the patient's spine depending on the surgery to be performed. For example, the offset main beam 12 can be positioned by the surgical frame 300 to place the patient P in a prone position (e.g., FIGS. 27 and 28), lateral positions (e.g., FIGS. 29 and 30), and in a position 45° between the prone and lateral positions. The translating beam 302 can be positioned to accommodate the rotational position of the offset main beam 12 to aid in the stability of the surgical frame 300. For example, when the patient P is in the prone position, the translating beam 302 can preferably be moved to the center of the surgical frame 300 underneath the patient P. Furthermore, when the patient P is in one of the lateral positions, the translating beam 302 can be moved toward one of the corresponding lateral sides $L_1$ and $L_2$ of the surgical frame 300 to position underneath the patient P. Such positioning of the translating beam 302 can serve to increase the stability of the surgical frame 300.

A preferred embodiment of a surgical frame incorporating a moveable cart (FIG. 31) interconnected with a translating beam are generally indicated by the numeral 400 in FIGS. 32-38. Like the surgical frames 10 and 300, the surgical frame 400 can serve as an exoskeleton to support the body of the patient P as the patient's body is manipulated thereby. In doing so, the surgical frame 400 serves to support the patient P such that the patient's spine does not experience unnecessary stress/torsion. Furthermore, while only one cart is depicted in FIGS. 31-38, multiple carts can be interconnected with the translating beam 404 in the fashion discussed below.

As depicted in FIGS. 32-38, the surgical frame 400 includes a support platform 402 including a translating beam 404. Like the translating beam 302, the translating beam 404 is capable of translating motion affording it to be positioned and repositioned with respect to portions of the remainder of the surgical frame 400. To illustrate, the translating beam 404 is moveable between a first terminal position (FIGS. 32 and 33), a second terminal position (FIGS. 34 and 35), and positions therebetween (FIGS. 36-38) relative to the remainder of the surgical frame 400. The surgical frame 400 includes similar components to the surgical frame 300 and identical numbering is used in FIGS. 32-38. Furthermore, the servomotor 70 of the surgical frame 400 can incorporate a transmission, and the servomotor 70 can drive rotation of the main beam 12 via use of the transmission.

Additionally, the support platform 402 includes a linkage 406 for interconnecting a surgical cart 408 to the translating beam 404. As discussed below, the cart 408 can be configured to support surgical equipment thereon, and movement of the translating beam 404 also moves the cart 408. The cart 408, for example, can include one or more casters or rollers 410 allowing for movement thereof. As such, the cart 408 can be positioned and repositioned with the translating beam 404 using the linkage 406. Additional carts 408 also can be interconnected with the linkage 406. At the very least, the interconnection of the cart 408 with the translating beam 404 allows the cart 408 and the surgical equipment supported thereby to move in unison with one another.

As discussed above with respect the translating beam 302, the surgical frame 400 and the translating beam 404 can similarly include the components of the of the surgical frame 300 affording movement of the translating beam 404. To illustrate, the surgical frame 400 can be configured such that operation of the first and second translation mechanism 340 and 342 can be controlled by an operator such as a surgeon and/or a surgical assistant. As such, movement of the translating beam 404 can be facilitated by controlled automation. The controlled automation can be either manually or programmably effectuated using various controllers and controls (not shown). To illustrate, the surgical frame 400 can be configured such that movement of the translating beam 404 automatically coincides with the rotation of the main beam 12. By tying the position of the translating beam 404 to the rotational position of the main beam 12, the movement and the position of the translating beam 404 and the cart 408 do not interfere with the rotation of the main beam 12, and the center of gravity of the surgical frame 400 can be maintained in positions advantageous to the stability thereof. Also, by tying the position of the cart 408 with the translating beam 404, the position of the cart 408 does not interfere with movement of the translating beam 404. Moreover, such controlled automation can be used to control the position of such components to position the cart 408 relative to the patient.

As depicted in FIGS. 32-38, the linkage 406 can be moveably attached to the translating beam 404. To illustrate, the linkage 406 can be moveable linearly along the translating beam 404 between a first terminal linear position and a second terminal linear position using a linear-movement mechanism 412 of the support platform 402. The first terminal linear position is where the linkage 406 is at or adjacent one end of the translating beam 404, and the second terminal linear position is where the linkage 406 is at or adjacent the other end of the translating beam 404. The linear-movement mechanism 412 can employ an electrical servomotor 414 or a hand crank (not shown), a transmission 416, and a track 418. The track 418 can be provided on the translating beam 404, and the transmission 416 is interoperable with the track 418. The electrical servomotor 414 or hand crank can drive the transmission 416, and the transmission 416 can include gear(s) or wheel(s) for contacting the track 418. As such, operation of the electrical servomotor 414 or the hand crank can move the linkage 406 between the first terminal linear position and the second terminal linear position by driving the transmission 416. Using the linear movement of the linkage 406, the cart 408 can be moved along the translating beam 404 from at least adjacent one end to at least adjacent the other end thereof.

Using the electrical servomotor 414, the movement of the linkage 406 and the cart 408 relative to the translating beam 404 can be automated. Thus, like movement of the main beam 12 and the translating beam 404, controlled automation can allow the movement of the linkage 406 and the cart 408 to be controlled by an operator such as a surgeon and/or a surgical assistant. The controlled automation can be either manually or programmably effectuated using various controllers and controls (not shown). As such, along with movement via the translating beam 404, the linkage 406 and the cart 408 can be positioned and repositioned relative to the translating beam 404 and the patient P during surgery. In addition to the controlled automation controlling the position of the translating beam 404, controlling the position of the cart 408 relative to the translating beam 404 using the servomotor 414 to move the linkage 406 along the translating beam 404 can be used to prevent interference of the cart 408 with the rotation of the main beam 12 and to maintain an advantageous center of gravity for the stability of the surgical table 400. Moreover, such controlled automation can be used to control the position of such components to position the cart 408 relative to the patient.

Additionally, rather than using the linkage 406, a telescoping linkage for interconnecting the cart 408 to the translating beam 404 can be used. The telescoping linkage can include a first portion (not shown) that can be fixedly or moveably attached to the translating beam 404 and a second portion (not shown) that can be fixedly attached to the cart 408.

The telescoping linkage can be configured for telescoping movement such that the second portion is capable of moving inwardly and outwardly between a first terminal telescoped position and a second terminal telescoped position with respect to the first portion using a telescoping-movement mechanism (not shown). The first terminal telescoped position is where the second portion is fully retracted relative to the first portion, and the second terminal telescoped position where the second is fully extended relative to the first portion. Similar to the linear movement mechanism 412, the telescoping-movement mechanism can employ an electrical servomotor (not shown) or hand crank (not shown) for driving a transmission (not shown) facilitating telescoping of the second portion relative to the first portion. The transmission can include, for example, gears or screws for engaging complimentary structures on the second portion in similar fashion to the linear movement mechanism 412. As such, operation of the electrical servomotor or hand crank can move the telescoping linkage between the first terminal telescoped position and the second terminal telescoped position by driving the transmission. Using the telescoping movement of the telescoping linkage, the cart 408 can be moved inwardly and outwardly relative to the translating beam 404.

Using the electrical servomotor employed with the telescoping linkage, movement of the cart 408 inwardly and outwardly relative to the translating beam 404 can be automated. Thus, like movement of the translating beam 404 and the linkage 406, controlled automation can allow the movement of the telescoping linkage to be controlled by an operator such as a surgeon and/or a surgical assistant. The controlled automation can be either manually or programmably effectuated using various controllers and controls (not shown). In addition to the controlled automation controlling the position of the translating beam 404, and controlling the position of the cart 408 relative to the translating beam 404 using the servomotor 414 to move the telescoping linkage along the translating beam 404, controlling the position of the telescoping linkage inwardly and outwardly can be used to prevent interference of the cart 408 with the rotation of the main beam 12 and to maintain an advantageous center of gravity for the stability of the surgical table 400. Moreover, such controlled automation can be used to control the position of such components to position the cart 408 relative to the patient.

As discussed above, the cart 408 can be configured to support surgical equipment thereon. The surgical equipment can include, for example, a surgical robot 500 thereon. The surgical robot 500 can include a robotic arm 502 and a telescoping shaft 504 supporting the robotic arm 502 that are positionable and repositionable during surgery via controlled automation. The controlled automation can be either manually or programmably effectuated using various controllers and controls (not shown). For example, the telescoping shaft 504 can be moveable upwardly and downwardly with respect to the cart 408 and the patient P, and the robotic arm 502 can be moveable upwardly, downwardly, inwardly, and outwardly with respect to the telescoping shaft 504 and the patient P. Using such movement, the robot arm 502 can be positioned adjacent a surgical site on the patient P. Thus, the movement of the translating beam 404, movement of the linkage 406 and the cart 408, and/or movement of the telescoping linkage can be used to generally position the surgical robot 500 relative to the patient P supported by the surgical frame 400, and the telescoping shaft 504 and the robotic arm 502 can thereafter finely position portions of the surgical robot 500 relative to the patient P.

FIGS. 32-38 illustrate use of the surgical frame 400, the cart 408, and the surgical robot 500. The same illustrated uses of the surgical frame 400 are also applicable to the surgical frame 400 incorporating the telescoping linkage, except that use of the telescoping linkage affords inward and outward movement of the cart 408 relative to the translating beam 404. The illustrated movement of the main beam 12, the translating beam 404, and the first linkage 406 can be effectuated by controlled automation via input from an operator such as a surgeon and/or a surgical assistant.

Figure 32:
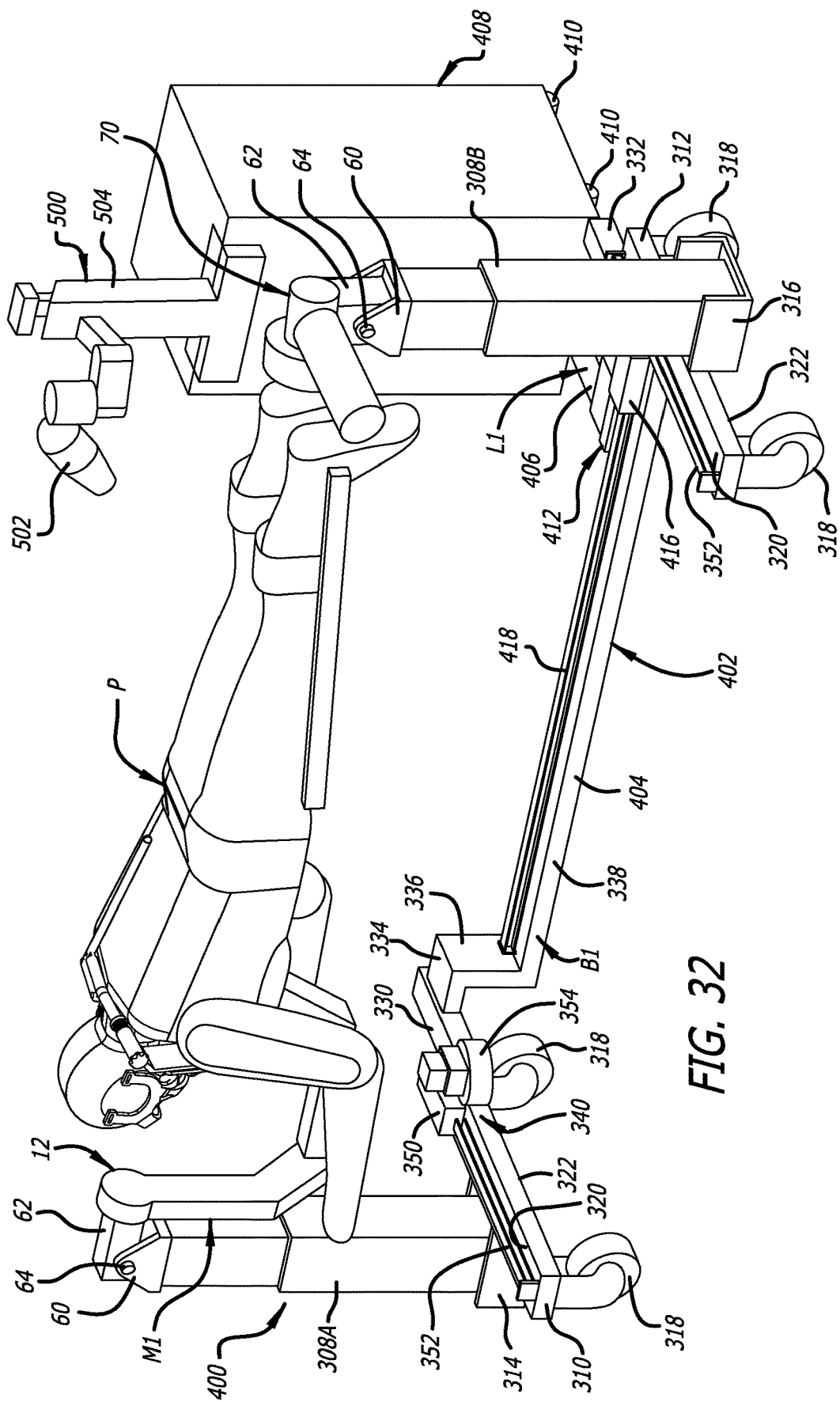
FIG. 32 is a top side perspective view from a first side of a surgical frame with a patient positioned thereon in a prone position, the surgical frame including the translating beam and the linear movement mechanism, the translating beam being located in a first position, and the linear movement mechanism being located in a first linear position.

FIG. 32 depicts the patient P positioned in the prone position on the surgical frame 400, the main beam 12 in a first position M1 supporting the patient P in the prone position, the translating beam 404 positioned in a first position B1 collocated with the first terminal position thereof, and the linkage 406 (and surgical cart 408 attached thereto) positioned in a first linear position L1 collocated with the first terminal linear position thereof. From the first position B1, the translating beam 404 can be moved toward the second terminal position, and from the first linear position L1, the linkage 406 (and the cart 408 attached thereto) can be moved toward the second terminal linear position.

Figure 33:
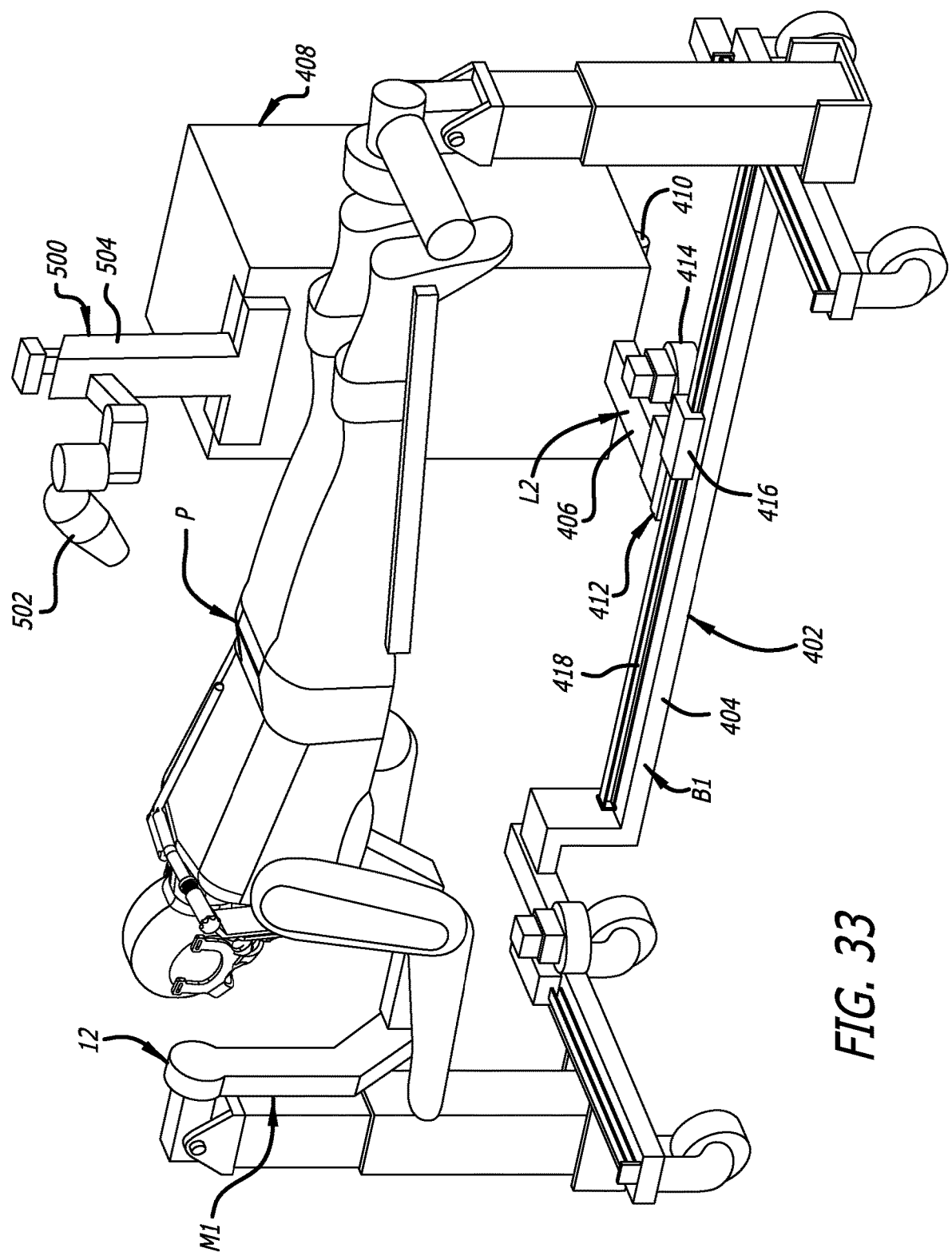
FIG. 33 is a top side perspective view from the first side of the surgical frame of FIG. 32 with the patient positioned thereon in the prone position, the translating beam being located in the first position, and the linear movement mechanism being located in a second linear position.

FIG. 33 depicts the patient P positioned in the prone position on the surgical frame 400, the main beam 12 in the first position M1 supporting the patient in the prone position, the translating beam 404 positioned in the first position B1, and the linkage 406 (and surgical cart 408 attached thereto) positioned in a second linear position L2.

Figure 34:
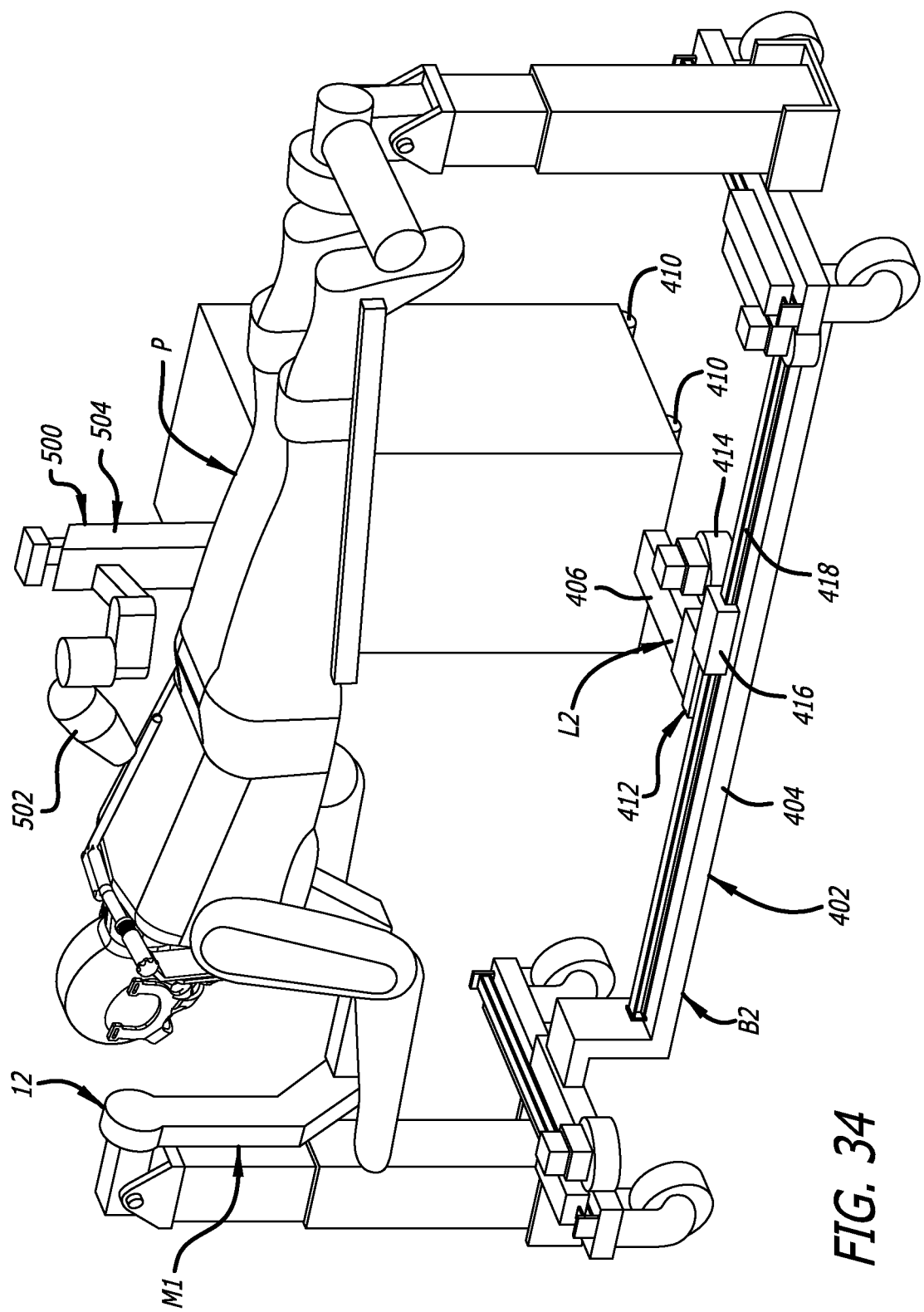
FIG. 34 is a top side perspective view from the second side of the surgical frame of FIG. 32 with the patient positioned thereon in the prone position, the translating beam being located in a second position, and the linear movement mechanism being located in the second linear position, the second position of the translating beam and the second position of the linear movement mechanism locating the surgical robot for surgery on the patient in the prone position.
Figure 35:
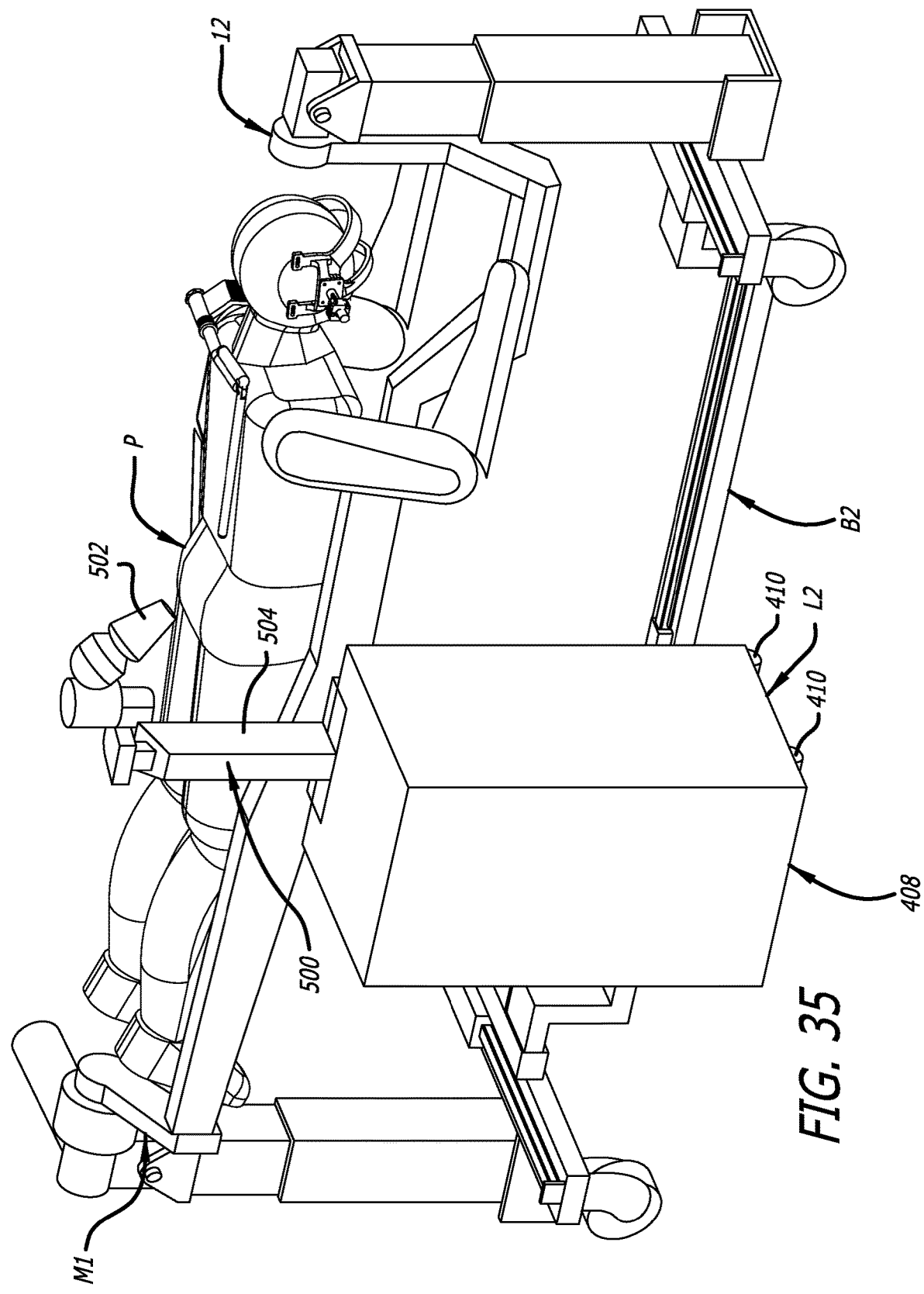
FIG. 35 is a top side perspective view from a second side of the surgical frame of FIG. 32 with the patient positioned thereon in the prone position, the translating beam being located in the second position, the linear movement mechanism being located in the second linear position, and the surgical robot being located to assist with surgery on the patient in the prone position.

FIGS. 34 and 35 depict the patient P positioned in the prone position on the surgical frame 400, the main beam 12 in the first position M1 supporting the patient P in the prone position, the translating beam 404 positioned in a second position B2 collocated with the second terminal position thereof, and the linkage 406 positioned in the second linear position L2. The movement of the translating beam 404 from the first position B1 to the second position B2 brings the surgical robot 500 into close proximity to the patient P.

Figure 36:
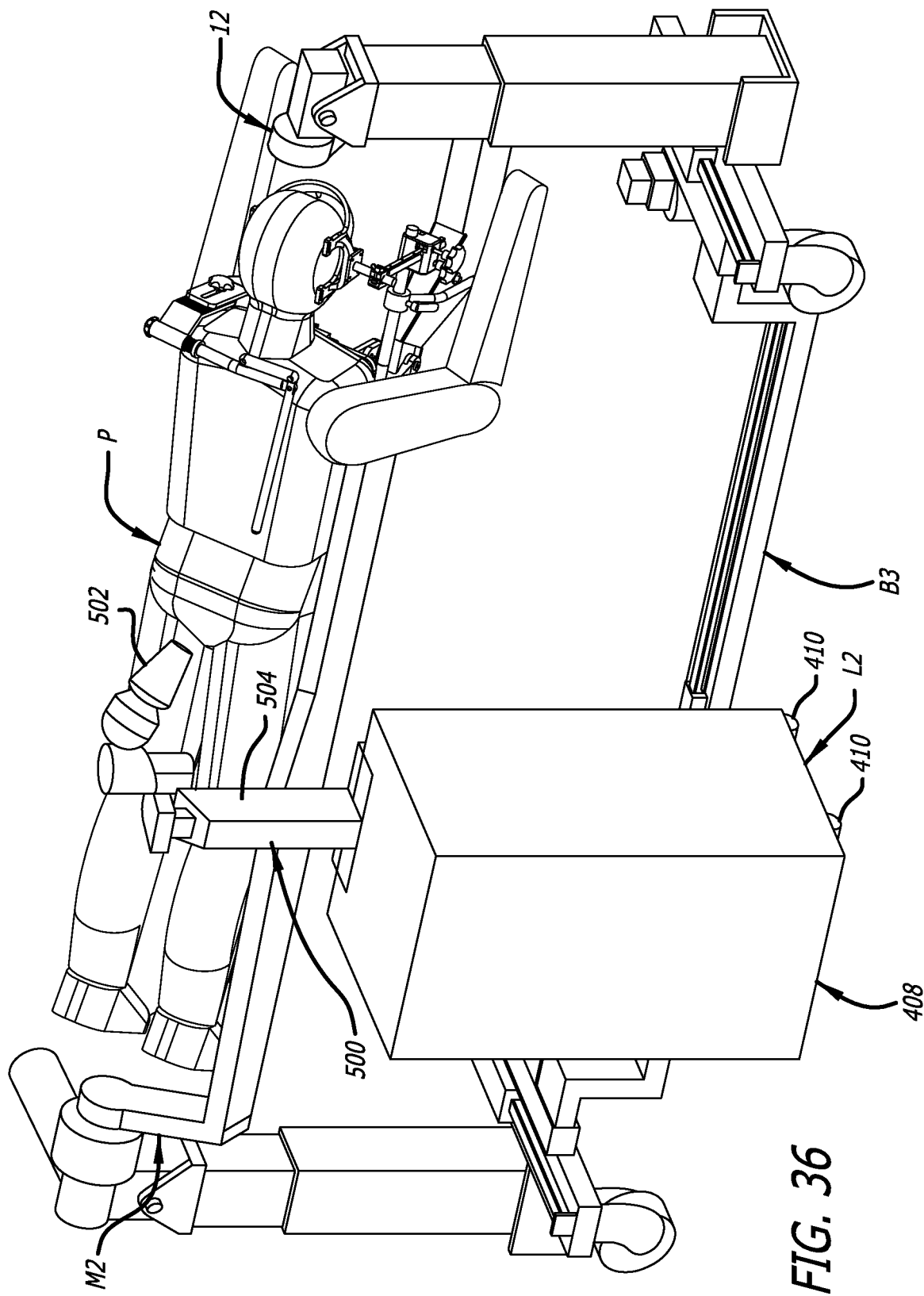
FIG. 36 is a top side perspective view from the second side of the surgical frame of FIG. 32 with the patient positioned thereon in a first angled position, the translating beam being located in a third position between the first and second positions, the linear movement mechanism being located in the second linear position, and the surgical robot being positioned to assist with surgery on the patient in the first angled position.
Figure 37:
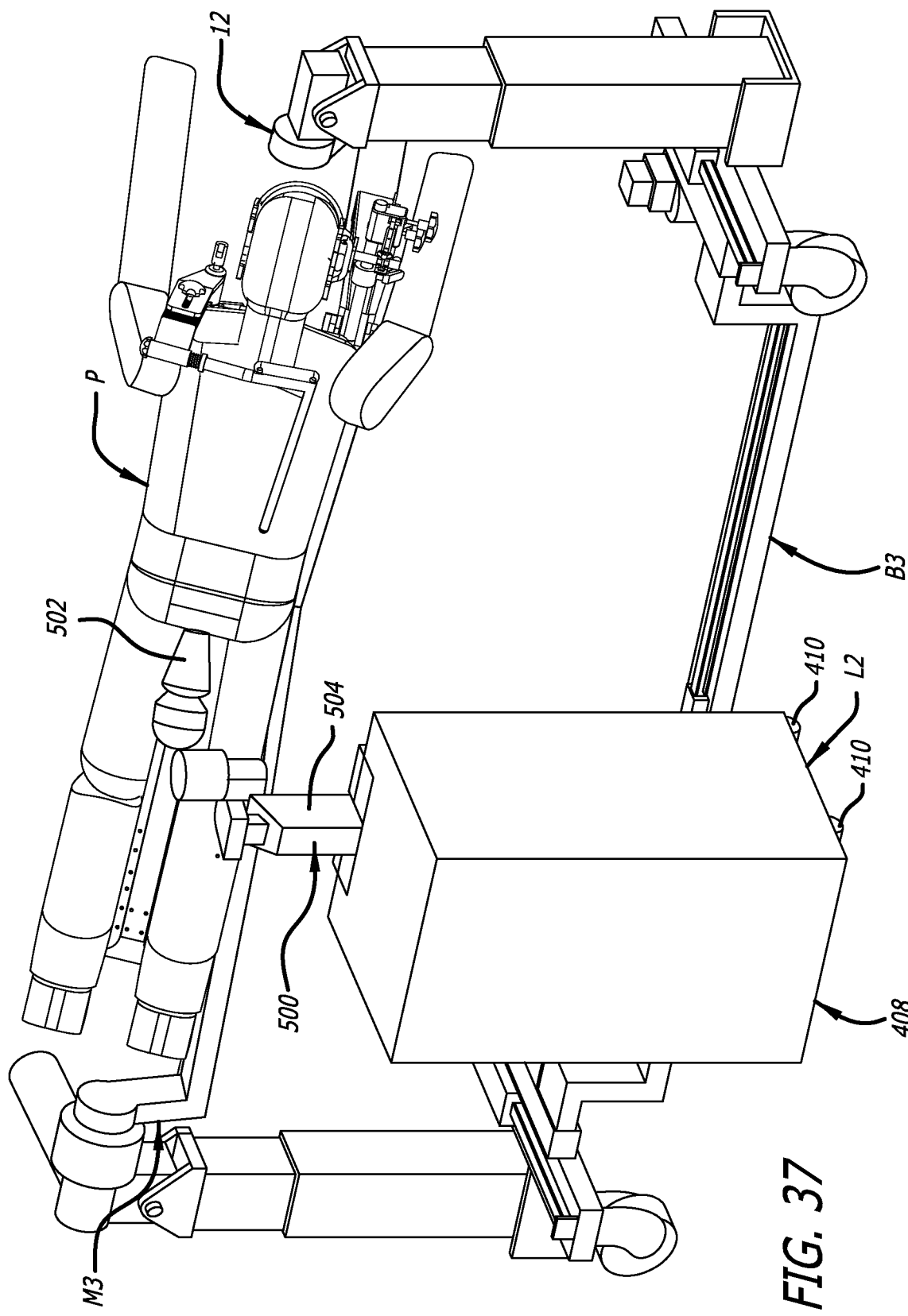
FIG. 37 is a top side perspective view from the second side of the surgical frame of FIG. 32 with the patient positioned thereon in a second angled position, the translating beam being located in the third position, the linear movement mechanism being located in the second linear position, and the surgical robot being positioned to assist with surgery on the patient in the second angled position.

FIGS. 36 and 37 depict the patient P in a first angled position and a second angled position, respectively, the main beam 12 in a second position M2 and a third position M3, respectively, supporting the patient P in the first angled position and the second angled position, the translating beam 404 positioned in a third position B3 and the linkage 406 positioned in the second linear position L2. The movement of the translating beam 404 from the second position B2 (FIGS. 36 and 37) to the third position B3 prevents interference of the cart 408 with the rotation of the main beam 12 from the first position M1 to the second position M2 to the third position M3. The movement of the translating beam 404 from the second position B2 to the third position B3 also serves in maintaining the position of the surgical robot 500 in close proximity to the patient P.

Figure 38:
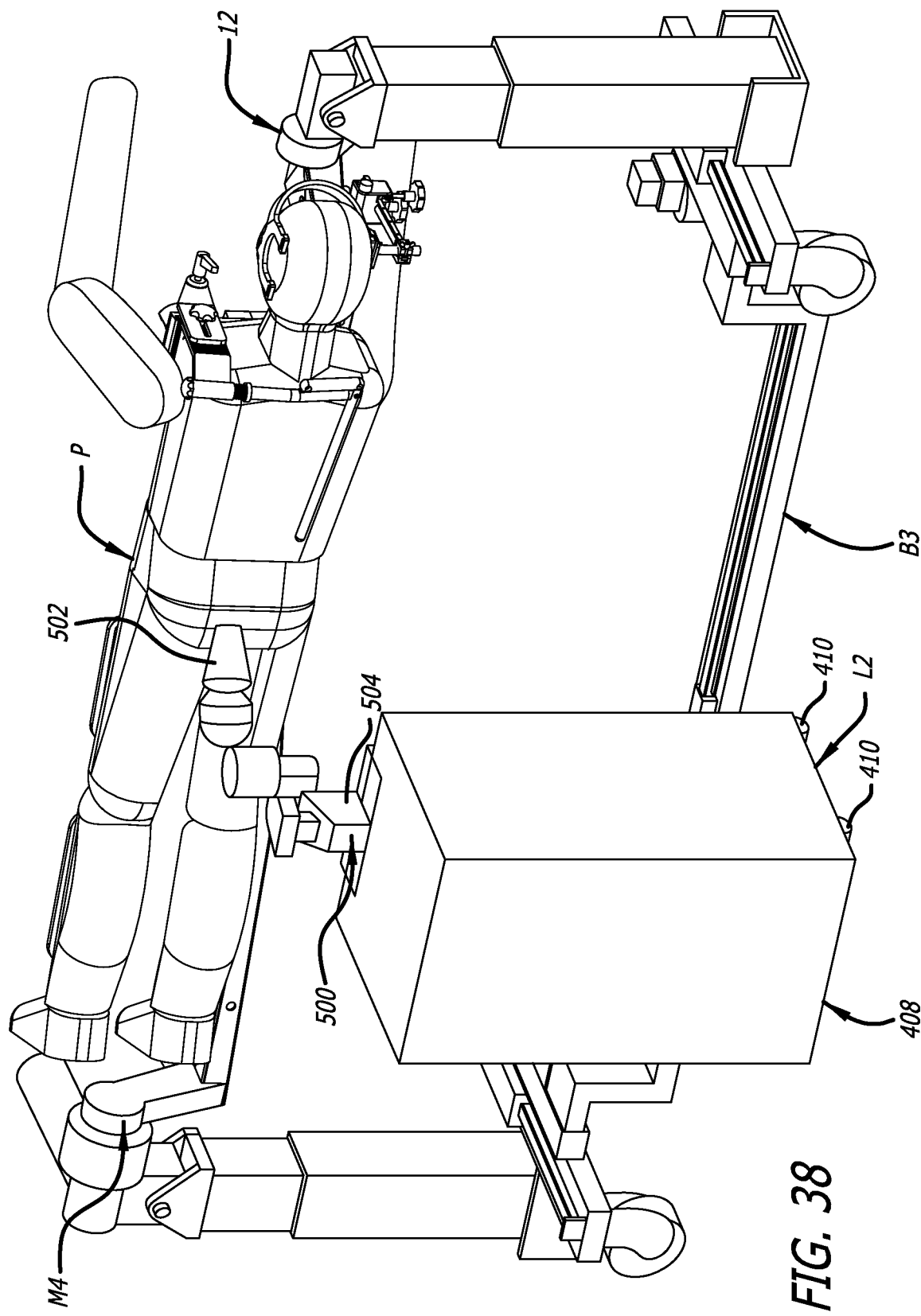
FIG. 38 is a top side perspective view from the second side of the surgical frame of FIG. 32 with the patient positioned thereon in a lateral position, the translating beam being located in the third position, the linear movement mechanism being located in the second linear position, and the surgical robot being positioned to assist with surgery on the patient in the lateral position.

FIG. 38 depicts the patient P in a lateral position, the main beam 12 in a fourth position M4 supporting the patient P in the lateral position, the translating beam 404 positioned in the third position B3, and the linkage 406 positioned in the second linear position L2. The position of the translating beam 404 in the third position B3 again prevents interference of the cart 408 with the rotation of the main beam 12 from the third position M3 to the fourth position M4. The position of the translating beam 404 in the third position B3 also serves in maintaining the position of the surgical robot 500 in close proximity to the patient P.

As discussed above, the controlled automation of the main beam 12, the translating beam 404, the linkage 406, and the telescoping linkage can ensure that the movement of these components do not interfere with one another and with the main beam 12, while simultaneously maintaining an advantageous center of gravity for the stability of the surgical table 400. Such movement, as discussed above, also facilitates positioning of the surgical cart 408 and/or the surgical robot 500 relative to the patient P. Furthermore, during or after movement of the main beam 12, the translating beam 404, the linkage 406, and/or the telescoping linkage, the telescoping shaft 504 can be moveable upwardly and downwardly with respect to the cart 408 and the patient P, and the robotic arm 502 can be moveable upwardly, downwardly, inwardly, and outwardly with respect to the telescoping shaft 504 and the patient P. To illustrate, in FIGS. 35-38, the telescoping shaft 504 is progressively lowered to position the surgical arm 502 adjacent a selected portion of the patient P, and the surgical arm 502 is progressively extended toward the selected portion of the patient P.

While the linkage 406 and the telescoping linkage in preferred embodiments thereof are used in association with the translating beam 404, it is appreciated that the linkage 404 and the telescoping linkage described herein also have applicability with surgical frames without a translating beam. The linkage 406 and the telescoping linkage in other embodiments may be supportively and moveably attached to a lower beam, even if the lower beam does not have translating capabilities. In yet other alternative embodiments, the linkage 406 and the telescoping linkage have applicability with surgical frames with or without a lower beam by being supportively and moveably attached to another portion of the surgical frames permitting the linkage 406 and the telescoping linkage to move the cart 408.

As depicted in FIGS. 39-42, the support platform 402 of the surgical frame 400 can also include a patient support arm 600 or a patient support arm 600A. The patient support arm 600 and the patent support arm 600A can be used in place of or in addition to the linkage 406 and the linear movement mechanism 412. Rather than being interconnected with the translating beam 404 via the linkage 406, surgical equipment such as the patient support arm 600 and the patient support art 600A can be supportively and moveably attached to the translating beam 404.

Figure 39:
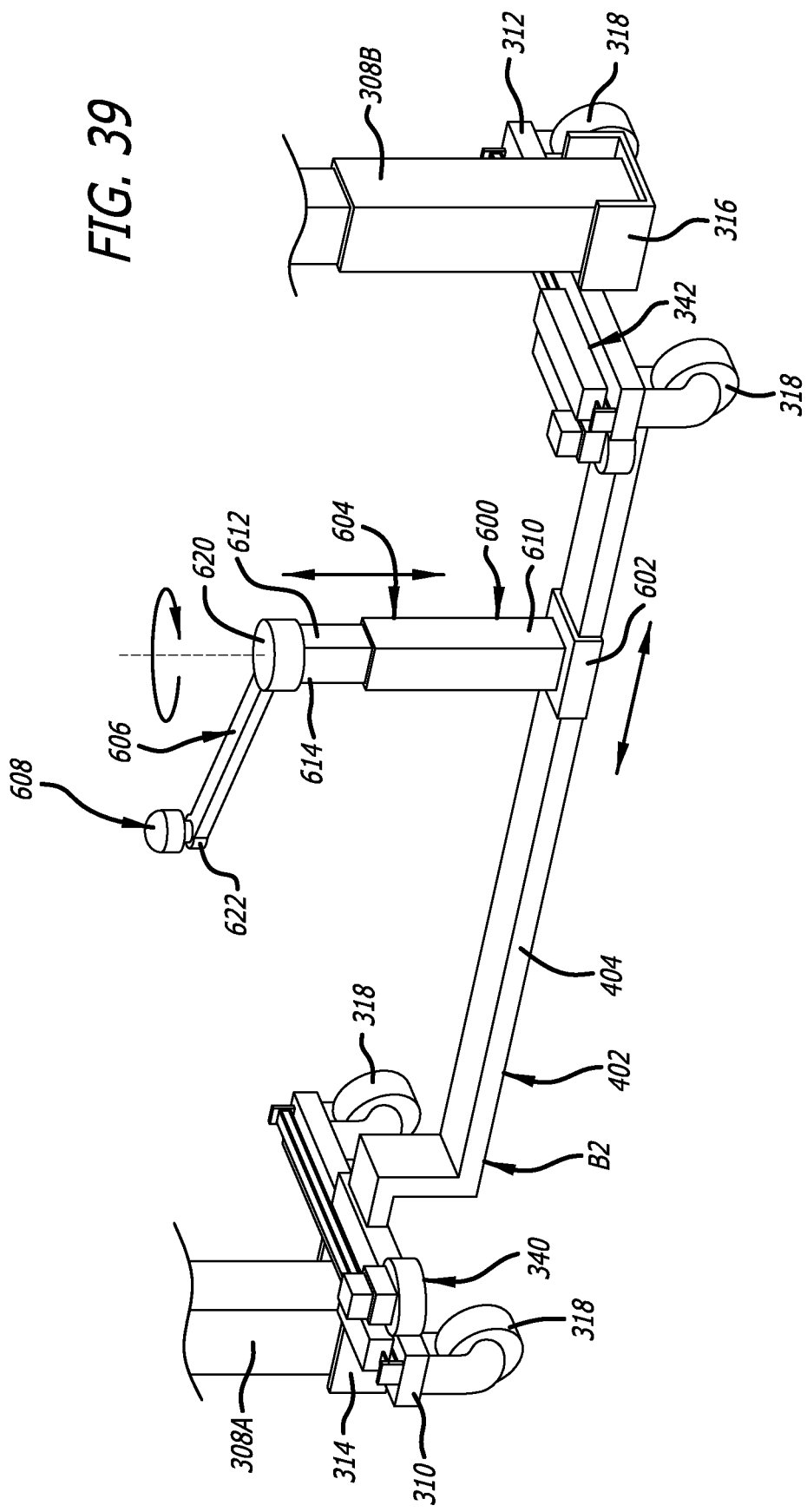
FIG. 39 is a top side perspective view of a portion of the first side of the surgical frame of FIG. 32 depicting a first embodiment of a patient support arm supportively and moveably attached to the translating beam thereof.

As depicted in FIGS. 39 and 40-42, the patient support arm 600 is supported by and manually moveable with respect to the translating beam 404, and as depicted in FIG. 39A, the patient support arm 600A is supported by and moveable with respect to the translating beam using a linear movement mechanism 630. To illustrate with respect to FIGS. 39 and 40-42, the patient support arm 600 is supported by and is moveable linearly along the translating beam 404 via manual adjustment. The patient support arm 600 can be fixedly supported by the translating beam 404 at various increments along the translating beam 404 between a first terminal linear position and a second terminal linear position, and the surgeon and/or surgical assistant can manually adjust the patient support arm 600 to a selected position therealong. Furthermore, to illustrate with respect to FIG. 39A, the patient support arm 600A is supported by and is moveable linearly along the translating beam 404 via actuation of the linear movement mechanism 630 using controlled automation or manual operation. The patient support arm 600A of FIG. 39A can be fixedly supported by a portion of the linear movement mechanism 630, and the portion of the linear movement mechanism 630 can be moved along the translating beam 404 between a first terminal position and a second terminal position via actuation thereof. The first terminal linear positions are where the patient support arm 600 or the patient support arm 600A are at or adjacent one end of the translating beam 404, and the second terminal linear positions are where the patient support arm 600 are at or adjacent the other end of the translating beam 404.

Similarly, additional surgical equipment can be supportively and moveably attached to the translating beam 404 in similar fashion to the patient support arm 600 as depicted in FIGS. 39 and 40-42 and the patient support arm 600A as depicted in FIG. 39A. For example, like the patient support arm 600, a C-arm (not shown) facilitating fluoroscopic imaging at least before and during surgery can be supportively and moveably attached to the translating beam 404.

Figure 41:
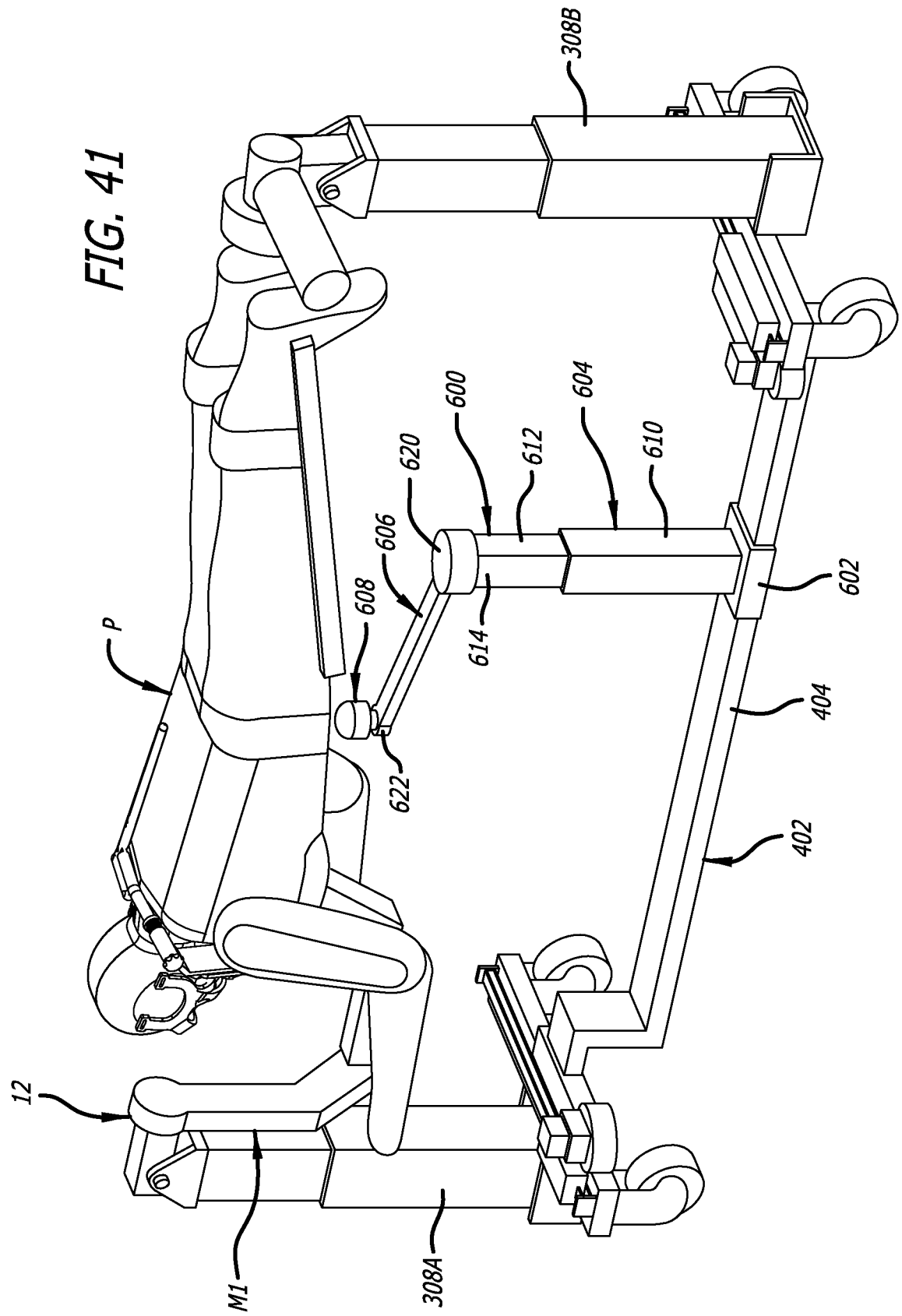
FIG. 41 is top side perspective view from the first side of the surgical frame of FIG. 32 with the patient positioned thereon in the prone position, the main beam being located in a first angled position, and the patient support arm being used to support the pelvis of the patient.

The patient support 600 and the patient support 600A are provided to support portions of the patient P at different rotational positions and heights/angles of the main beam 12. As discussed above, the patient P can be rotated on the main beam 12 between various rotational positions M1, M2, M3, and M4, and the patient support 600 and the patient support 600A can be used to support, for example, the patient P, in these different rotational positions. Furthermore, the height/angle of the main beam 12 can be varied by adjusting the height of the first vertical support post 308A and the second vertical support post 308B, and the patient support arm 600 and the patient support arm 600A can be used to support, for example, the patient P at these different heights/angles as depicted in FIGS. 40-42. To illustrate, the first vertical support post 308A has a greater height than the second vertical support post 308B in FIG. 40; the second vertical support post 308B has a greater height than the first vertical support post 308A in FIG. 41; and the first vertical support post 308A and the second vertical support post 308B have approximately the same height in FIG. 42, which is greater than the heights thereof in either of FIGS. 40 and 41. Although the patient support arm 600 is depicted FIGS. 40-42, the patient support arm 600A can be used similarly.

The patient support arm 600, as depicted in FIGS. 39 and 40-42, includes a base portion 602, a post portion 604, an arm portion 606, and a pad portion 608. The base portion 602 is supported by and moveable along the translating beam 404. The base portion 602 can be fixedly supported by the translating beam 404 at various increments along the translating beam 404 affording adjustment therealong. The post portion 604 includes a first portion 610 attached to the base portion 602, and a second portion 612 capable of telescoping movement inwardly and outwardly with respect to the first portion 610. The base portion 602 can be configured to afford telescoping movement thereof via controlled automation or manual operation. The second portion 612 includes an end portion 614, and the arm portion 606 is rotatably attached to the end portion 614. The arm portion 606 includes a first end portion 620 and a second end portion 622. The first end portion 620 is rotatably attached to the end portion 614, and the second end portion 622 supports the pad portion 608 thereon. The pad portion 608 can be contacted to various portions of the patient P, and such contact facilitates support of these portions of patient P by the patient support arm 600. To position the pad portion 608 into contact with the patient P, the base portion 602 can be moved along the translating beam 404, the second portion 612 can be moved inwardly and outwardly with respect to the first portion 610, and the arm portion 606 can be rotated relative to the end portion 614 of the second portion 612.

Like the patient support arm 600, the patient support art 600A, as depicted in FIG. 39A, includes the post portion 604, the arm portion 606, and the pad portion 608 that can be used similarly. However, rather than including the base portion 602, the components of the patient support arm 600A can be attached to the linear movement mechanism 630. The linear movement mechanism 630 can employ an electrical motor 632 or a hand crank (not shown), a transmission portion 634, a truck portion 636, and a track 638. As depicted in FIG. 39A, the track 638 is provided on the translating beam 404, the truck portion 636 is moveable along the track 638, and the transmission portion 434 can be driven by the electrical servomotor 632 or hand crank to actuate movement of the truck portion 636 along the track 638. The transmission can include gear(s) or wheel(s) for contacting the track 638 to drive movement of the truck portion 636 along the track 638. As such, operation of the electrical servomotor 632 or the hand crank can move the truck portion 636 between the first terminal linear position and the second terminal linear position by driving the transmission portion 634. Furthermore, the truck portion 636 can include an attachment surface 640 for fixedly supporting the base portion 602 of the patient support arm 600A thereon. Thus, using the linear movement of the truck portion 636, the patient support arm 600A can be moved along the translating beam 404 from at least adjacent one end to at least adjacent the other end thereof.

Using the electrical servomotor 632, the movement of the truck portion 636 and hence, the patient support arm 600A can be automated. Thus, like movement of at least the translating beam 404, the linkage 406, and the telescoping linkage, controlled automation can allow the movement of the patient support arm 600A to be controlled by an operator such as a surgeon and/or a surgical assistant. The controlled automation can be either manually or programmably effectuated using various controllers and controls (not shown). As such, the patient support arm 600A can be positioned and repositioned relative to the translating beam 404 and the patient P during surgery.

While the patient support arms 600 and 600A in preferred embodiments thereof are used in association with the translating beam 404, it is appreciated that the patient support arms 600 and 600A described herein also have applicability with surgical frames without a translating beam. The patient support arms 600 and 600A in other embodiments may be supportively and moveably attached to a lower beam, even if the lower beam does not have translating capabilities. In yet other alternative embodiments, the patient support arms 600 and 600A have applicability with surgical frames with or without a lower beam by being supportively and moveably attached to another portion of the surgical frames permitting the patient support arms 600 and 600A to moveably support a patient before, after, and during rotation of the patient.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of reconfiguring a surgical frame and positioning a cart interconnected with the surgical frame before, during, or after surgery, the method comprising:
   supporting a patient on a main beam of the surgical frame, the main beam being spaced from the ground by a first support portion at a first end of the main beam and a second support portion at a second end of the main beam;
   rotating the main beam of the surgical frame from at least a first position supporting the patient in a prone position to a second position supporting the patient in one of an angled position and a lateral position;
   moving a translating beam relative to portions of the first support portion and the second support portion between a first lateral side and a second lateral side of the surgical frame, the translating beam being moveably supported at a first end thereof by the first support portion and moveably supported at a second end thereof by the second support portion;
   moving a cart relative to the translating beam between a first position at least adjacent the first end of the translating beam and a second position at least adjacent the second end of the translating beam, the cart being attached relative to the translating beam by a linkage moveably attached to the translating beam;
   wherein the movement of the translating beam relative to the portions of the first support portion and the second support portion and the movement of the cart relative to the translating beam prevents the cart from interfering with the rotation of the main beam.

2. The method of claim 1, wherein the cart supports surgical equipment thereon.

3. The method of claim 2, further comprising moving the translating beam relative to the portions of the first and second support portions and moving the cart relative to the translating beam to position the cart and the surgical equipment supported by the cart adjacent a surgical site on the patient.

4. The method of claim 3, wherein the surgical equipment is a surgical robot including a robotic arm, and further comprising moving the surgical arm upwardly, downwardly, inwardly, and outwardly with respect to the patient to assist with surgery.

5. The method of claim 1, wherein the second position of the main beam supports the patient in the angled position, and further comprising adjusting the position of a surgical robot supported by the cart into a position adjacent a surgical site on the patient via movement of the translating beam and the cart.

6. The method of claim 5, further comprising moving a distal end of a surgical arm of the surgical robot to a position at or directly adjacent the surgical site to assist with surgery.

7. The method of claim 1, wherein the second position of the main beam supports the patient in the lateral position, and further comprising adjusting the position of a surgical robot supported by the cart into a position adjacent a surgical site on the patient via movement of the translating beam and the cart.

8. The method of claim 7, further comprising moving a distal end of a surgical arm of the surgical robot to a position at or directly adjacent the surgical site to assist with surgery.

9. A method of moving surgical equipment with respect to a surgical frame before, during, or after surgery, the method comprising:
   supporting a patient on a main beam of the surgical frame, the main beam being spaced from the ground by a first support portion at a first end of the main beam and a second support portion at a second end of the main beam;
   moving the translating beam relative to portions of the first support portion and the second support portion between a first lateral side and a second lateral side of the surgical frame, the translating beam being moveably supported at a first end thereof by the first support portion and moveably supported at a second end thereof by the second support portion;
   moving the surgical equipment relative to the translating beam between a first position at least adjacent the first end of the translating beam and a second position at least adjacent the second end of the translating beam, the surgical equipment being attached relative to the translating beam by a linkage moveably attached to the translating beam;
   wherein the movement of the translating beam relative to the portions of the first support portion and the second support portion and the movement of the surgical equipment relative to the translating beam prevents the surgical equipment from interfering with the main beam.

10. The method of claim 9, further comprising moving the translating beam relative to the portions of the first and second support portions and moving the surgical equipment relative to the translating beam to position the surgical equipment supported adjacent a surgical site on the patient.

11. The method of claim 10, wherein the surgical equipment is a surgical robot including a robotic arm, and further comprising moving the surgical arm upwardly, downwardly, inwardly, and outwardly with respect to the patient to assist with surgery.

12. The method of claim 9, wherein the main beam can support the patient in an angled position, wherein the surgical equipment is a surgical robot, and further comprising adjusting the surgical robot into a position adjacent a surgical site on the patient via movement of the translating beam and the surgical robot.

13. The method of claim 12, further comprising moving a distal end of a surgical arm of the surgical robot to a position at or directly adjacent the surgical site to assist with surgery.

14. The method of claim 9, wherein the main beam can support the patient in a lateral position, and the surgical equipment is a surgical robot, and further comprising adjusting of the surgical robot into a position adjacent a surgical site on the patient via movement of the translating beam and the surgical robot.

15. The method of claim 14, further comprising moving a distal end of a surgical arm of the surgical robot to a position at or directly adjacent the surgical site to assist with surgery.

16. A reconfigurable surgical frame and a surgical cart interconnected with the reconfigurable surgical frame comprising:
a first support portion, a second support portion, a main beam, a translating beam, a linkage, and a surgical cart, the main beam being spaced from the ground by at least the first support portion and the second support portion, the translating beam being moveably attached at a first end thereof relative to the first support portion and moveably attached at a second end thereof relative to the second support portion, and being moveable between a first position at or adjacent a first lateral side of the surgical frame and a second position at or adjacent a second lateral side of the surgical frame, the linkage being moveably attached to the translating beam via a linear movement mechanism, and being moveable via actuation of the linear movement mechanism between a first position at or adjacent a first end of the translating beam and a second position at or adjacent a second end of the translating beam, the surgical cart being interconnected to the translating beam via the linkage;
wherein movement of the translating beam and the linkage prevents the cart from interfering with the main beam.

17. The reconfigurable surgical frame and the surgical cart of claim 16, further comprising a surgical robot supported by the cart; wherein the translating beam and the linkage are moveable to position the cart and the surgical robot adjacent a surgical site on the patient.

18. The reconfigurable surgical frame and the surgical cart of claim 17, wherein the surgical robot includes a robotic arm, and the surgical arm is configured to move upwardly, downwardly, inwardly, and outwardly with respect to the patient to assist with surgery.

19. The reconfigurable surgical frame and the surgical cart of claim 16, wherein the linear movement mechanism includes a track provided on the translating beam, a transmission interoperable with the track and interconnected to the linkage, and an electrical motor driving the transmission to facilitate movement of the linkage relative to the translating beam between the first position and the second position thereof.

20. The reconfigurable surgical frame and the surgical cart of claim 19, wherein the first support portion includes a first translation mechanism interconnecting the translating beam with the first support portion, and the second support portion includes a second translation mechanism interconnecting the translating beam with the second support portion, actuation of the first translation mechanism and the second translation mechanism facilitating movement of the translating beam between the first position and the second position thereof.

* * * * *